US012618065B2

(12) United States Patent
Harper

(10) Patent No.: US 12,618,065 B2
(45) Date of Patent: *May 5, 2026

(54) MiRNA DETARGETING SYSTEM FOR TISSUE SPECIFIC INTERFERENCE

(71) Applicant: RESEARCH INSTITUTE AT NATIONWIDE CHILDREN'S HOSPITAL, Columbus, OH (US)

(72) Inventor: Scott Quenton Harper, Powell, OH (US)

(73) Assignee: RESEARCH INSTITUTE AT NATIONWIDE CHILDREN'S HOSPITAL, Columbus, OH (US)

( * ) Notice: Subject to any disclaimer, the term of this patent is extended or adjusted under 35 U.S.C. 154(b) by 1033 days.

This patent is subject to a terminal disclaimer.

(21) Appl. No.: 16/651,814

(22) PCT Filed: Oct. 2, 2018

(86) PCT No.: PCT/US2018/054005
§ 371 (c)(1),
(2) Date: Mar. 27, 2020

(87) PCT Pub. No.: WO2019/070741
PCT Pub. Date: Apr. 11, 2019

(65) Prior Publication Data
US 2020/0248179 A1 Aug. 6, 2020

Related U.S. Application Data

(60) Provisional application No. 62/566,966, filed on Oct. 2, 2017.

(51) Int. Cl.
| | |
|---|---|
| *C12N 15/113* | (2010.01) |
| *A61K 35/76* | (2015.01) |
| *C12N 7/00* | (2006.01) |
| *C12N 15/86* | (2006.01) |
| *A61K 48/00* | (2006.01) |

(52) U.S. Cl.
CPC ............ *C12N 15/113* (2013.01); *A61K 35/76* (2013.01); *C12N 7/00* (2013.01); *C12N 15/86* (2013.01); *A61K 48/00* (2013.01); *C12N 2750/14143* (2013.01)

(58) Field of Classification Search
CPC ................. C12N 15/113; C12N 15/86; C12N 2750/14143; C12N 2310/141; C12N 15/111; C12N 15/63; C12N 7/00; C12N 2330/51; A61K 48/00; A61K 35/76; Y02A 50/30
See application file for complete search history.

(56) References Cited

U.S. PATENT DOCUMENTS

| | | | |
|---|---|---|---|
| 5,173,414 A | 12/1992 | Lebkowski et al. | |
| 5,658,776 A | 8/1997 | Flotte et al. | |
| 5,786,211 A | 7/1998 | Johnson | |
| 5,871,982 A | 2/1999 | Wilson et al. | |
| 6,258,595 B1 | 7/2001 | Gao et al. | |
| 6,566,118 B1 | 5/2003 | Atkinson et al. | |
| 7,250,289 B2 * | 7/2007 | Zhou ..................... | C12Q 1/6837 536/23.1 |
| 7,683,036 B2 * | 3/2010 | Esau ....................... | A61P 37/00 536/23.1 |
| 9,181,544 B2 * | 11/2015 | Davidson ................ | A61P 25/14 |
| 9,597,380 B2 * | 3/2017 | Chakraborty .......... | A61K 39/00 |
| 10,189,888 B2 * | 1/2019 | Falkner .................. | C12N 15/86 |
| 11,162,102 B2 * | 11/2021 | Minshull .............. | C12N 9/1241 |
| 2010/0186103 A1 * | 7/2010 | Gao .................... | A01K 67/0275 800/13 |
| 2012/0225034 A1 | 9/2012 | Belayew et al. | |
| 2013/0195801 A1 | 8/2013 | Gao et al. | |
| 2017/0166925 A1 | 6/2017 | Gao et al. | |
| 2019/0328791 A1 * | 10/2019 | McKinney-Freeman ..................... | C12N 5/0605 |

FOREIGN PATENT DOCUMENTS

| | | | |
|---|---|---|---|
| WO | 1995/13365 A1 | 5/1995 | |
| WO | 1995/13392 A1 | 5/1995 | |
| WO | 1996/17947 A1 | 6/1996 | |
| WO | 1997/06243 A1 | 2/1997 | |
| WO | 1997/08298 A1 | 3/1997 | |
| WO | 1997/09441 A2 | 3/1997 | |
| WO | 1997/21825 A1 | 6/1997 | |
| WO | 1998/09657 A2 | 3/1998 | |
| WO | 1999/11764 A2 | 3/1999 | |
| WO | 2001/83692 A2 | 11/2001 | |
| WO | 2002/53703 A2 | 7/2002 | |
| WO | 2010/138263 A2 | 12/2010 | |
| WO | 2011/133890 A1 | 10/2011 | |
| WO | WO 2013016352 | * | 7/2012 |

(Continued)

OTHER PUBLICATIONS

Suhy et al (Mol Ther Sep. 4, 2012, vol. 20, No. 9, pp. 1737-1749, published online Jun. 26, 2012).*

Ansseau, Eugénie, et al. "Antisense oligonucleotides used to target the DUX4 mRNA as therapeutic approaches in faciosscapulohumeral muscular dystrophy (FSHD)." Genes 8.3 (2017): 93.*

Carter, Adeno-associated virus vectors, Curr. Opin. Biotechnol., 3(5):533-539 (1992).

Choudhury et al., In vivo selection yields AAV-B1 capsid for central nervous system and muscle gene therapy, Mol. Ther., 24(7):1247-1257 (2016).

Clark et al., A stable cell line carrying adenovirus-inducible rep and cap genes allows for infectivity titration of adeno-associated virus vectors, Gene. Ther., 3:1124-1132 (1996).

(Continued)

*Primary Examiner* — Kimberly Chong
(74) *Attorney, Agent, or Firm* — MARSHALL, GERSTEIN & BORUN LLP

(57) ABSTRACT

The present disclosure relates to a tissue-specific promoter system for expressing microRNA (miRNA) for RNA interference-based methods of gene therapy. In these systems, the miRNA will inhibit gene expression or replace natural miRNA expression using microRNA.

20 Claims, 4 Drawing Sheets

Specification includes a Sequence Listing.

(56) References Cited

FOREIGN PATENT DOCUMENTS

WO      2013/016352 A1     1/2013
WO      2017/173411 A1     10/2017

OTHER PUBLICATIONS

Clark et al., Highly purified recombinant adeno-associated virus vectors are biologically active and free of detectable helper and wild-type viruses, Hum. Gene. Ther., 10(6):1031-1039 (1999).

Cserjesi et al., Myogenin induces the myocyte-specific enhancer binding factor MEF-2 independently of other muscle-specific gene products, Mol. Cell. Biol., 11:4854-4862 (1991).

De et al., High levels of persistent expression of alpha1-antitrypsin mediated by the nonhuman primate serotype rh.10 adeno-associated virus despite preexisting immunity to common human adeno-associated viruses, Mol. Ther., 13(1):67-76 (2006).

Fechner et al., Cardiac-targeted RNA interference mediated by an AAV9 vector improves cardiac function in coxsackievirus B3 cardiomyopathy, J. Mol. Med., 86:987-997 (2008).

Flotte et al., Gene expression from adeno-associated vrrus vectors in airway epithelial cells, Am. J. Respir. Cell Mol. Biol., 7:349-356 (1992).

Gao et al., Clades of adeno-associated viruses are widely disseminated in human tissues, J. Virol., 78:6381-6388 (2004).

Hermonat et al., Use of adeno-associated virus as a mammalian DNA cloning vector: transduction of neomycin resistance into mammalian tissue culture cells, Proc. Natl. Acad. Sci. USA, 81:6466-6470 (1984).

International Application No. PCT/US2018/054005, International Preliminary Report on Patentability, mailed Apr. 16, 2020.

International Application No. PCT/US2018/054005, International Search Report and Written Opinion, mailed Dec. 26, 2018.

Johnson et al., Muscle creatine kinase sequence elements regulating skeletal and cardiac muscle expression in transgenic mice, Mol. Cell. Biol., 9:3393-3399 (1989).

Laughlin et al., Cloning of infectious adeno-associated virus genomes in bacterial plasmids, Gene., 23:65-73 (1983).

Lebkowski et al., Adeno-associated virus: a vector system for efficient introduction and integration of DNA into a variety of mammalian cell types, Mol. Cell. Biol., 8:3988-3996 (1988).

Lemmers et al., Supporting Online Material for, A Unifying Genetic Model for Facioscapulohumeral Muscular Dystrophy, Aug. 19, 2010 highlight DUX4.

Mader et al., A steroid-inducible promoter for the controlled overexpression of cloned genes in eukaryotic cells, Proc. Natl. Acad. Sci. USA, 90:5603-5607 (1993).

Marsic et al., Vector design Tour de Force: integrating combinatorial and rational approaches to derive novel adeno-associated virus variants, Mol. Ther., 22(11):1900-1909 (2014).

Mccarty, Self-complementary AAV vectors; advances and applications, Mol. Ther., 16(10):1648-1656 (2008).

Mclaughlin et al., Adeno-associated virus general transduction vectors: analysis of proviral structures, J. Virol., 62:1963-1973 (1988).

Mcmanus et al., Gene silencing using micro-RNA designed hairpins, RNA, 8(6):842-850 (2002).

Mori et al., Two novel adeno-associated viruses from cynomolgus monkey: pseudotyping characterization of capsid protein, Virology, 330(2):375-383 (2004).

Muscat et al., Multiple 5'-flanking regions of the human alpha-skeletal actin gene synergistically modulate muscle-specific expression, Mol. Cell. Biol., 7:4089-4099 (1987).

Muzyczka, Use of adeno-associated virus as a general transduction vector for mammalian cells, Curr. Top. Microbiol. Immunol., 158:97-129 (1992).

Neguembor et al., In junk we trust: repetitive DNA, epigenetics and facioscapulohumeral muscular dystrophy, Epigenomics, 2(2):271-287 (2010).

Paul et al., Increased viral titer through concentration of viral harvests from retroviral packaging lines, Hum. Gene Ther., 4:609-615 (1993).

Perrin et al., An experimental rabies vaccine produced with a new BHK-21 suspension cell culture process: use of serum-free medium and perfusion-reactor system, Vaccine, 13:1244-1250 (1995).

Rodino-Klapac et al., A translational approach for limb vascular delivery of the micro-dystrophin gene without high vol. or high pressure for treatment of Duchenne muscular dystrophy, J. Transl. Med., 5:45 (2007).

Samulski et al., Cloning of adeno-associated virus into pBR322: rescue of intact virus from the recombinant plasmid in human cells, Proc. Natl. Acad. Sci. USA, 79:2077-2081 (1982).

Samulski et al., Helper-free stocks of recombinant adeno-associated viruses: normal integration does not require viral gene expression, J. Virol., 63:3822-3828 (1989).

Schnepp et al., Highly purified recombinant adeno-associated virus vectors. Preparation and quantitation, Methods Mol. Med., 69:427-443 (2002).

Semenza et al., Hypoxia-inducible nuclear factors bind to an enhancer element located 3' to the human erythropoietin gene, Proc. Natl. Acad. Sci. USA, 88:5680-5684 (1991).

Senapathy et al., Molecular cloning of adeno-associated virus variant genomes and generation of infectious virus by recombination in mammalian cells, J. Biol. Chem., 259:4661-4666 (1984).

Srivastava et al., Nucleotide sequence and organization of the adeno-associated virus 2 genome, J. Virol., 45:555-564 (1983).

Tratschin et al., A human parvovirus, adeno-associated virus, as a eucaryotic vector: transient expression and encapsidation of the procaryotic gene for chloramphenicol acetyltransferase, Mol. Cell. Biol., 4:2072-2081 (1984).

Tratschin et al., Adeno-associated virus vector for high-frequency integration, expression, and rescue of genes in mammalian cells, Mol. Cell. Biol., 5:3251-3260 (1985).

Wallace et al., Developing RNAi therapy for FSHD, Mol. Ther., 17(Suppl. 1):S151 (2009).

Wei et al., Therapeutic RNAi for dominant muscle disease, Mol. Ther., 17(Suppl 1):S200 (2009).

Weintraub et al., The myoD gene family: nodal point during specification of the muscle cell lineage, Science, 251:(4995)761-766 (1991).

Wuebbles et al., Testing the effects of FSHD candidate gene expression in vertebrate muscle development, Int. J. Clin. Exp. Pathol., 3(4):386-400 (2010).

Xiao et al., Production of high-titer recombinant adeno-associated virus vectors in the absence of helper adenovirus, J. Virol., 72:2224-2232 (1998).

Danda et al., Targeted Expression of Suicide Gene by Tissue-Specific Promoter and MicroRNA Regulation for Cancer Gene Therapy, Plos One., 8(12):e83398 (2013).

European Application No. 18863924.9, European Search Report and Opinion, mailed Apr. 15, 2021.

Geisler et al., microRNA122-regulated transgene expression increases specificity of cardiac gene transfer upon intravenous delivery of AAV9 vectors, Gen. Ther., 18(2):199-209 (2010).

Wolff et al., Effect of tissue-specific promoters and microRNA recognition elements on stability of transgene expression after hydrodynamic naked plasmid DNA delivery, Hum. Gen. Ther., 20(4):374-388 (2009).

Zhou et al., A tightly regulated Pol Ill promoter for synthesis of miRNA genes in tandem, Bio. et Biop. Acta., 1779(11):773-779 (2008).

* cited by examiner

SEQ ID NO: 3 – Wild type U6-1 Promoter

ACGTGACGGAGCGTGACCGCGCGCCGAGCGCGCGCCAAGGTCGGGCAGGAAGAGG
GCCTATTTCCCATGATTCCTTCATATTTGCATATACGATACAAGGCTGTTAGAGAGAT
AATTAGAATTAATTTGACTGTAAACACAAAGATATTAGTACAAAATACGTGACGTA
GAAAGTAATAATTTCTTGGGTAGTTTGCAGTTTTAAAATTATGTTTTAAAATGGACT
ATCATATGCTTACCGTAACTTGAAAGTATTTCGATTTCTTGGCTTTATATATCTTGTG
GAAAGGACGAAACACCCTCGAG

SEQ ID NO: 7

MiRNA DETARGETING SYSTEM FOR TISSUE SPECIFIC INTERFERENCE

This application claims priority benefit of U.S. Provisional Patent Application No. 62/566,966, filed Oct. 2, 2017, which is incorporated by reference herein in its entirety.

FIELD OF THE INVENTION

The present disclosure relates to a tissue-specific promoter system for expressing microRNA (miRNA) for RNA interference-based methods of gene therapy. In these systems, the miRNA will inhibit gene expression or replace natural miRNA expression using microRNA.

INCORPORATION BY REFERENCE OF THE SEQUENCE LISTING

This application contains, as a separate part of disclosure, a Sequence Listing in computer-readable form (Filename: 52375A_SeqListing.txt; 1,684,382 bytes—ASCII text file, created Oct. 1, 2018) which is incorporated by reference herein in its entirety.

BACKGROUND

RNA interference (RNAi) is a mechanism of gene regulation in eukaryotic cells that has been considered for the treatment of various diseases. RNAi refers to post-transcriptional control of gene expression mediated by microRNAs (miRNAs). Natural miRNAs are small (21-25 nucleotides), noncoding RNAs that share sequence homology and base-pair with 3' untranslated regions of cognate messenger RNAs (mRNAs), although regulation in coding regions may also occur. The interaction between the miRNAs and mRNAs directs cellular gene silencing machinery to degrade target mRNA and/or prevent the translation of the mRNAs. The RNAi pathway is summarized in Duan (Ed.), Section 7.3 of Chapter 7 in *Muscle Gene Therapy*, Springer Science+Business Media, LLC (2010).

As an understanding of natural RNAi pathways has developed, researchers have designed artificial miRNAs for use in regulating expression of target genes for treating disease. As described in Section 7.4 of Duan, supra, artificial miRNAs can be transcribed from DNA expression cassettes. The miRNA sequence specific for a target gene is transcribed along with sequences required to direct processing of the miRNA in a cell. Viral vectors such as adeno-associated virus have been used to deliver miRNAs to muscle [Fechner et al., *J. Mol. Med.*, 86: 987-997 (2008)].

Adeno-associated virus (AAV) is a replication-deficient parvovirus, the single-stranded DNA genome of which is about 4.7 kb in length including two 145 nucleotide inverted terminal repeat (ITRs). There are multiple serotypes of AAV. The nucleotide sequences of the genomes of the AAV serotypes are known. For example, the complete genome of AAV-1 is provided in GenBank Accession No. NC_002077; the complete genome of AAV-2 is provided in GenBank Accession No. NC_001401 and Srivastava et al., *J. Virol.*, 45: 555-564 {1983); the complete genome of AAV-3 is provided in GenBank Accession No. NC_1829; the complete genome of AAV-4 is provided in GenBank Accession No. NC_001829; the AAV-5 genome is provided in GenBank Accession No. AF085716; the complete genome of AAV-6 is provided in GenBank Accession No. NC_00 1862; at least portions of AAV-7 and AAV-8 genomes are provided in GenBank Accession Nos. AX753246 and AX753249, respectively; the AAV -9 genome is provided in Gao et al., *J. Virol.*, 78: 6381-6388 (2004); the AAV-10 genome is provided in *Mol. Ther.*, 13(1): 67-76 (2006); and the AAV-11 genome is provided in *Virology*, 330(2): 375-383 (2004). Cloning of the AAVrh.74 serotype is described in Rodino-Klapac., et al. *Journal of Translational Medicine* 5, 45 (2007). Isolation of the AAV-B 1 serotype is described in Choudhury et al., *Mol. Therap.* 24(7): 1247-57, 2016. Cis-acting sequences directing viral DNA replication (rep), encapsidation/packaging and host cell chromosome integration are contained within the AAV ITRs. Three AAV promoters (named p5, p19, and p40 for their relative map locations) drive the expression of the two AAV internal open reading frames encoding rep and cap genes. The two rep promoters (p5 and p19), coupled with the differential splicing of the single AAV intron (at nucleotides 2107 and 2227), result in the production of four rep proteins (rep 78, rep 68, rep 52, and rep 40) from the rep gene. Rep proteins possess multiple enzymatic properties that are ultimately responsible for replicating the viral genome. The cap gene is expressed from the p40 promoter and it encodes the three capsid proteins VP1, VP2, and VP3. Alternative splicing and non-consensus translational start sites are responsible for the production of the three related capsid proteins. A single consensus polyadenylation site is located at map position 95 of the AAV genome. The life cycle and genetics of AAV are reviewed in Muzyczka, *Current Topics in Microbiology and Immunology*, 158: 97-129 (1992).

AAV possesses unique features that make it attractive as a vector for delivering foreign DNA to cells, for example, in gene therapy. AAV infection of cells in culture is noncytopathic, and natural infection of humans and other animals is silent and asymptomatic. Moreover, AAV infects many mammalian cells allowing the possibility of targeting many different tissues in vivo. Moreover, AAV transduces slowly dividing and non-dividing cells, and can persist essentially for the lifetime of those cells as a transcriptionally active nuclear episome (extrachromosomal element). The AAV proviral genome is inserted as cloned DNA in plasmids, which makes construction of recombinant genomes feasible. Furthermore, because the signals directing AAV replication and genome encapsidation are contained within the ITRs of the AAV genome, some or all of the internal approximately 4.3 kb of the genome (encoding replication and structural capsid proteins, rep-cap) may be replaced with foreign DNA. To generate AAV vectors, the rep and cap proteins may be provided in trans. Another significant feature of AAV is that it is an extremely stable and hearty virus. It easily withstands the conditions used to inactivate adenovirus (56° to 65° C. for several hours), making cold preservation of AAV less critical. AAV may even be lyophilized. Finally, AAV-infected cells are not resistant to superinfection.

miRNA-based therapies, including miRNA inhibition and miRNA replacement, may be used to treat many diseases such as hepatitis C viral infection, muscular dystrophies, neurodegenerative diseases, peripheral neuropathies, chronic heart failure and post-myocardial infarction remodeling and cancers. In addition, miRNA directed regulation of gene expression may improve traditional gene therapy approaches in which the vector payload is a protein coding gene. Systemically delivered AAV vectors preferentially transduce the liver, resulting in high-level transgene expression in that organ if a liver-active promoter is used. As described in detail herein, the insertion of liver-specific miR-122 binding sites reduce transgene expression in the liver when a liver-specific promoter is used.

SUMMARY

The present disclosure provides for a system for tissue-specific expression of miRNA in vectors comprising detargeting miRNA binding sequences placed at various locations within the miRNA mature guide strand. The nucleic acid molecules of the disclosure comprise a tissue specific promoter and a miRNA mature guide strand comprising the corresponding binding site to detarget expression of the miRNA in a specific tissue. In particular, the disclosure provides for nucleic acid molecules comprising a tissue specific promoter sequence, mature guide strand of a miRNA comprising at least one detargeting sequence and 5-6 thymidines at the 5' end. In one example, the nucleic acid molecules have U6 promoter and a miRNA mature guide strand containing the miR-122 and miR-208 binding site to detarget expression of the miRNA in the liver and heart, respectively. In a proof-of-concept study, liver-specific miR-122 target sequences were inserted into AAV vectors carrying luciferase or LacZ reporter genes. In these vectors, ubiquitously active U6 promoters were used to drive transcription of both genes. AAV vectors lacking miR-122 sites resulted in extremely high levels of luciferase or LacZ expression in mouse livers, while transcription of the same genes was reduced 50- and 70-fold, respectively, when delivered by vectors carrying miR-122 binding sites in each respective coding gene. Such systems have not been employed for microRNA expression vectors (Reference PMID: 21150938).

The nucleic acid molecules of the disclosure comprise any tissue specific promoter. Exemplary tissue specific promoters include U6 promoter sequence, MHCK7 promoter sequence, CK6 promoter sequence, tMCK promoter sequence, CK5 promoter sequence, MCK promoter sequence, HAS promoter sequence, MPZ promoter sequence, desmin promoter sequence, APOA2 promoter sequence, hAAT promoter sequence, INS promoter sequence, IRS2 promoter sequence, MYH6 promoter sequence, MYL2 promoter sequence, TNNI3 promoter sequence, SYN1 promoter sequence, GFAP promoter sequence, NES promoter sequence, MBP promoter sequence, or TH promoter sequence.

The disclosure provides for nucleic acid molecules comprising an U6 promoter sequence and miRNA mature guide strand sequence comprising at least one detargeting sequence and 5-6 thymidines at the 5' end. The nucleic acid molecules of the disclosure comprise at least two detargeting sequences, at least three detargeting sequences, at least four detargeting sequences, at least five detargeting sequences or more. In addition to the tissue specific miRNA binding sites, the DNA nucleic acid sequence comprises a transcription termination signal for RNA polymerase III, which comprises five thymidines at the 5' end or comprises six thymidines at the 5' end. When transcribed into RNA, these thymidines are added to the transcript as uracils.

The "detargeting sequence" is the binding site for any tissue-specific miRNA that is desired to be inhibited in a tissue. For example, the disclosure provides nucleic acid sequences wherein the detargeting sequence is the binding site for any natural miRNA, for example miR-122, miR-208, miR-1, miR-206, miR-133, miR-29a, miR-29b or miR-29c. Exemplary miRNA sequences are provided in Table 2.

The nucleic acid molecules of the disclosure comprise any miRNA mature guide strand that will inhibit expression of a gene of interest. For example, the nucleic acid molecules comprise the miRNA mature guide strand of miDUX4, miRNA-92, miRNA-17, miRNA-18a, miRNA-19a, miRNA-20a, miRNA-19b-1, mi-RNA-26a, miRNA-122, miRNA-126, miRNA-335, let-7a and let-7b, miRNA-34 (miR-34a), miRNA-10b, miRNA-208, miRNA-499, miRNA-195, miRNA-29a, miRNA-29b, or miRNA-29c. The nucleic acid molecules comprise any of the miRNA mature guide strands set out as SEQ ID NOS: 10-10912. The nucleic acid molecules of the disclosure comprise the mature guide strand of miDUX4 having the nucleic acid sequence of SEQ ID NO: 1 (miDUX4-1; mi405) or SEQ ID NO: 2 (miDUX-4-2; mi1155).

The nucleic acid molecule of the disclosure comprise the mature guide stand of a miRNA comprising a nucleotide sequence of any human miRNA such as those set out in the miRBase: the microRNA database websites (miRBase.org) or Table 2. The sequences provided in the miRBase: the microRNA database are incorporated by references herein. Exemplary miRNA include but are not limited to mir450 (SEQ ID NO: 10973), mi1155mi70 (SEQ ID NO: 8482), mi180 (SEQ ID NO: 8372), mi181(SEQ ID NO: 8371), mi182 (SEQ ID NO: 8370), mi185 (SEQ ID NO: 8367), mi186 (SEQ ID NO: 8366), mi187 (SEQ ID NO: 8365), mi333 (SEQ ID NO: 8219), mi334 (SEQ ID NO: 8218), mi400 (SEQ ID NO: 8152), mi405 (SEQ ID NO: 8147), mi407 (SEQ ID NO: 8145), mi1155 (SEQ ID NO: 7397), mi1156 (SEQ ID NO: 7396), mi1157 (SEQ ID NO: 7395), mi1308 (SEQ ID NO: 7108), mi1309 (SEQ ID NO: 7107), mi1310 (SEQ ID NO: 7106), mi1420 (SEQ ID NO: 6633), mi1422 (SEQ ID NO: 6631), mi1431 (SEQ ID NO: 6622), mi1434 (SEQ ID NO: 6619), mi1444 (SEQ ID NO: 6609), mi1445 (SEQ ID NO: 6608), mi1485 (SEQ ID NO: 6568), mi1492 (SEQ ID NO: 6561), mi1493 (SEQ ID NO: 6560), mi1519 ((SEQ ID NO: 10971) or mi1520 (SEQ ID NO: 10972). These sequences fold similarly to mature guide stands of mi405 and mi1155. Therefore, the disclosure provides for nucleic acid molecules in which the mir-208 bind site sequence (SEQ ID NO: 5 or SEQ ID NO: 66) and/or the mir-122 binding site sequence (SEQ ID NO: 6 or SEQ ID NO: 67) may be inserted into the loop of any of the foregoing mature guide strand at locations similar to those set out in the sequences in Table 1.

In an exemplary embodiment, the nucleic acid molecules of the disclosure comprise a U6 promoter having the nucleic acid sequence of SEQ ID NO: 3, the mature guide strand of miDUX4 with the miR-122 and/or miR-208 binding site within the loop of the mature guide strand or at 5' or 3' end of the mature guide strand and 5-6 thymidines. Exemplary nucleic acid molecules comprise the miRNA mature guide strand of miDUX4 and at least one detargeting sequence, e.g. miR-122 (SEQ ID NO: 5) or miR-208 (SEQ ID NO: 6) binding sites inserted within the loop of the mature guide strand, at the 5' end of the mature guide strand or at the 3' end of the mature guide strand, such as the nucleic acid sequence set out as any one of SEQ ID NOS: 10913-10968.

The disclosure provides for nucleic acid molecule comprising the nucleic acid sequence of any one of SEQ ID NOS: 1, 2 or 10913-10968.

In another embodiment, the disclosure provides for recombinant adeno-associated virus (AAV) comprising any of the nucleic acid molecules of the disclosure . The AAV can be any serotype, for example AAV-B1, AAVrh.74, AAV1, AAV2, AAV3, AAV4, AAVS, AAV6, AAV7, AAV8, AAV9, AAV-10, AAV-11, AAV-12 and AAV-13. Production of pseudotyped rAAV is disclosed in, for example, WO 01/83692. Other types of rAAV variants, for example rAAV with capsid mutations, are also contemplated. See, for example, Marsic et al., Molecular Therapy, 22(11): 1900-1909 (2014). The disclosure also provides for compositions comprising any of the disclosed AAV . In addition, the disclosure provides for recombinant AAV vectors that are self-complementary AAV vectors.

In another embodiment, the disclosure provides for methods of inhibiting expression of a gene in a cell comprising contacting the cell with a vector comprising the any of the nucleic acid molecules of the. For example, the disclosure provide for methods of inhibiting expression of a gene in a cell comprising contacting the cell with a recombinant AAV comprising any of the nucleic acid molecules of the disclosure. Other embodiments of the disclosure utilize other vectors or plasmids to deliver the disclosed nucleic acid molecules, e.g. other viral vectors such as adenovirus, retrovirus, lentivirus, equine-associated virus, alphavirus, pox viruses, herpes virus, polio virus, sindbis virus and vaccinia viruses, to deliver the nucleic acid molecules of the disclosure.

The disclosure also provides for methods of inhibiting expression of the DUX4 gene in a cell comprising contacting the cell with a recombinant AAV comprising any of the disclosed nucleic acid molecules or any of the disclosed compositions. For example, the method is carried out with a nucleic acid molecule of the disclosure comprising the U6 promoter, the mature guide strand of miDUX4 with the miR-122 and/or miR-208 binding site inserted within the loop of the mature guide strand or at 5' or 3' end of the mature guide strand and 5-6 thymidines or the nucleic acid molecule of the disclosure comprises the nucleic acid sequence of any one of SEQ ID NOS: 10913-10968.

The disclosure provides for a use of a recombinant AAV comprising any of the disclosed nucleic acid molecules or a disclosed composition for the preparation of a medicament for inhibiting expression of the DUX4 gene in a cell. The AAV or compositions utilized to prepare the medicament comprise a nucleic acid molecule comprising the U6 promoter, the mature guide strand of miDUX4 with the miR-122 and/or miR-208 binding site inserted within the loop of the mature guide strand or at 5' or 3' end of the mature guide strand and 5-6 thymidines or the nucleic acid molecule comprises the nucleic acid sequence of any one of SEQ ID NOS: 10913-10968.

The disclosure also provides for a composition for the use of a recombinant AAV comprising any of the disclosed nucleic acid molecules or a disclosed composition for inhibiting expression of the DUX4 gene in a cell. The AAV or compositions utilized to prepare the medicament comprise a nucleic acid molecule comprising the U6 promoter, the mature guide strand of miDUX4 with the miR-122 and/or miR-208 binding site inserted within the loop of the mature guide strand or at 5' or 3' end of the mature guide strand and 5-6 thymidines or the nucleic acid molecule comprises the nucleic acid sequence of any one of SEQ ID NOS: 10913-10968.

The disclosure further provides for methods of delivering DUX4 miRNA-encoding DNA to the skeletal muscle of an animal in need thereof, comprising administering to the animal a recombinant AAV comprising the nucleic acid sequence of any one of SEQ ID NOS: 10913-10968.

The disclosure also provides for use of a recombinant AAV comprising a disclosed nucleic acid sequence for delivering DUX4 miDNA-encoding nucleic acid molecule to the skeletal muscle of an animal in need thereof. The disclosure provides for compositions comprising the nucleic acid sequence of any one of SEQ ID NOS: 10913-10968 for delivering DUX4 miDNA-encoding nucleic acid molecule to the skeletal muscle of an animal in need thereof.

In another embodiment, the disclosure provides for methods of treating facioscapulohumeral muscular dystrophy comprising administering a recombinant adeno-associated virus comprising any of the nucleic acid molecules or any of the compositions of the disclosure. For example, the method is carried out with a disclosed nucleic acid molecule comprising the U6 promoter, the mature guide strand of miDUX4 with the miR-122 and/or miR-208 binding site inserted within the loop of the mature guide strand or at 5' or 3' end of the mature guide strand and 5-6 thymidines or the nucleic acid molecule having the nucleic acid sequence of any one of SEQ ID NOS: 10913-10968.

In any of the methods of the disclosure, the recombinant AAV is administered by intramuscular injection, transdermal transport or injection into the blood stream The disclosure provides for a use of a recombinant AAV comprising any disclosed nucleic acid molecule or a disclosed composition for the preparation of a medicament for treating facioscapulohumeral muscular dystrophy. The AAV or compositions utilized to prepare the medicament comprise a nucleic acid molecule of the comprising the U6 promoter, the mature guide strand of miDUX4 with the miR-122 and/or miR-208 binding site inserted within the loop of the mature guide strand or at 5' or 3' end of the mature guide strand and 5-6 thymidines or the nucleic acid molecule having the nucleic acid sequence of any one of SEQ ID NOS: 10913-10968.

In any of the uses of the disclosure, the medicament is formulated for administration by intramuscular injection, transdermal transport or injection into the blood stream.

The disclosure also provides for a composition for the use of a recombinant AAV comprising any disclosed nucleic acid molecules or a disclosed composition for treating facioscapulohumeral muscular dystrophy. The AAV or compositions utilized to prepare the medicament comprise a nucleic acid molecule comprising the U6 promoter, the mature guide strand of miDUX4 with the miR-122 and/or miR-208 binding site inserted within the loop of the mature guide strand or at 5' or 3' end of the mature guide strand and 5-6 thymidines or the nucleic acid molecule having the nucleic acid sequence of any one of SEQ ID NOS: 10913-10968 The compositions of the disclosure are formulated for administration by intramuscular injection, transdermal transport or injection into the blood stream.

DETAILED DESCRIPTION

The present disclosure provides for a system for tissue-specific specific expression of miRNA that results in tissue-specific inhibition of a gene of interest. The system comprises a promoter for tissue specific expression of a mature guide strand of a miRNA comprising detargeting sequences inserted within the mature guide strand to detarget expression of the that miRNA or gene of interest.

One example of the detargeting systems of the disclosure is the U6 promoter system for tissue-specific specific expression of miRNA. The U6 promoter system is a nucleic acid molecule comprising the U6 promoter sequence, the mature guide strand of a miRNA with detargeting sequences inserted within the mature guide strand sequence. For example, the binding site for the liver specific miR-122 and/or the binding site for the heart specific miR-208 inserted within the loop of mature guide strand of a miRNA or at the 5' or 3' end of the mature guide strand of a miRNA to detarget expression of the miRNA in the liver and heart, respectively.

The U6 promoter system provides, miRNA-guided inhibition of a target gene or replacement of a miRNA which may result in inhibition of a target gene or replacement of an under-transcribed miRNA. The wild type U6 promoter (U6-1) is set out as SEQ ID NO: 3.

Detargeting miRNA Sequence Expression

The promoter system of the disclosure is a nucleic acid molecule comprising a mature guide strand of a miRNA in which binding sites for detargeting miRNAs are inserted within the loop of the mature guide strand of the miRNA or at the 5' or 3' end of the mature guide stand of the miRNA. This system may be used with any tissue specific promoter or gene expression control element and any miRNA sequences. For example, in order to promote expression of miRNA sequence in skeletal muscle and to detarget expression of the miRNA in liver and heart tissue, the nucleic acid molecule comprises the mature guide stand of the miRNA in which the binding sites for liver specific miR-122 and/or the binding site for heart specific miR-208 are inserted within the loop of the mature guide strand or at the 5' or 3' end of the mature guide strand of the miRNA . The nucleotide sequence of the binding site for miRNA-122 is set out as SEQ ID NO: 5, and the nucleotide sequence of the binding site for miRNA-208 is set out as SEQ ID NO: 6.

Examples of muscle-specific promoters or muscle-specific control elements include a human skeletal actin gene element, cardiac actin gene element, myocyte-specific enhancer binding factor mef, muscle creatine kinase (MCK), truncated MCK (tMCK), myosin heavy chain (MHC), hybrid α-myosin heavy chain enhancer-/MCK enhancer-promoter (MHCK7), creatine kinase 5 (CK5) promoter, creatine kinase 6 (CK6) promoter, C5-12, murine creatine kinase enhancer element, skeletal fast-twitch troponin c gene element, desmin promoter sequence, myosin heavy chain 6 (MYH6) promoter, myosin light chain 2 (MYL2) promoter, slow-twitch cardiac troponin c gene element, the slow-twitch troponin i gene element, hypoxia-inducible nuclear factors, steroid-inducible element and glucocorticoid response element (gre).

Examples of cardiac-specific promoters include myosin heavy chain 6, cardiac muscle, alpha promoter (Myh6 or αMHC), myosin light chain 2, regulatory cardiac, slow promoter ($MYL_2$ or MLC-2v), troponin I type 3 promoter ($TNNI_3$ or cTnI), natriuretic peptide precursor A promoter or atrial natriuretic factor promoter (NPPA or ANF) and solute carrier family 8 (sodium/calcium exchanger) member 1 promoter ($Slc8_{a1}$ or Ncx1).

Examples of liver-specific promoters include apolipoprotein A-II promoter ($APOA_2$), Serpin peptidase inhibitor promoter, clade A (alpha-1 antiproteinase, antitrypsin), member 1 promoter, human α1 anti-trypsin promoter (hAAT), apolipoprotein A-I (APO-A1), and cytochrome P450 promoter.

Examples of pancreas-specific promoters include insulin promoter (INS), insulin receptor substrate 2 promoter ($IRS_2$), pancreatic and duodenal homeobox 1 promoter (Pdx1), aristaless-like homoeobox 3 promoter (Alx3), and pancreatic polypeptide promoter (Ppy).

Examples of central nervous system specific promoters include synapsin I promoter (SYN1 or hSYN), glial fibrillary acidic protein promoter (GFAP), internexin neuronal intermediate filament protein, alpha promoter or α-internexin promoter (INA), nestin promoter (NES), myelin-associated oligodendrocyte basic protein promoter (MOBP), myelin basic protein promoter (MBP), myelin protein zero (MPZ) promoter, tyrosine hydroxylase promoter (TH) and forkhead box A2 promoter ($FOXA_2$).

Examples of skin cell specific promoters include filaggrin promoter (FLG), kerarin 14 promoter ($K_{14}$), and transglataminase 3 promoter ($TGM_3$).

Examples of immune system cell specific promoters include integrin, alpha M promoter (ITGAM) and complement component 3 receptor 3 subunit promoter ($CD_{11}B$)

Examples of urogenital cell specific promoters include probasin promoter (Pbsn), uroplakin 2 promoter (Upk2), spermine binding protein promoter (Sbp) and Fer-1-like 4 promoter (Fer114). An example of an endothelial cell specific promoter is endoglin promoter (ENG)

If detargeting expression of a miRNA in skeletal muscle is desired, binding sites for miR-1, miR-206 or miR-133 are inserted within the loop of the mature guide strand of the miRNA or at the 5' or 3' end of the mature guide strand of the miRNA.

If detargeting expression in tissues other than skeletal muscle, liver and/or heart is desired, binding sites for different miRNA transcripts may be inserted within the mature guide strand of the miRNA. For example, the miR-142 binding site may be used to detarget transcript expression in hematopoietic cells. Binding sites for miR-29a, miR-29b, and/or miR-29c may be used to detarget miRNA expression in normal tissues and to target miRNA expression in tumor tissue.

The miRNA binding sequences that may be used for detargeting miRNA expression in a tissue are collectively denoted herein as "detargeting sequences." The nucleic acid sequence of the disclosure comprises at least one copy of a detargeting sequence, or at least two copies of a detargeting sequence, or at least three copies of a detargeting sequence, or at least four copies of the detargeting sequence or at least five copies of a detargeting sequence. The nucleic acid molecule of the disclosure comprises 1-5 copies of a detargeting sequence, or 1-4 copies of a detargeting sequence, or 1-3 copies of the detargeting sequence or 1-2 copies of the detargeting sequence, or 2-5 copies of the detargeting sequence, 2-4 copies of a detargeting sequence, or 2-3 copies of a detargeting sequence, or 3-5 copies of a detargeting sequence, or 3-4 copies of a detargeting sequence, or 4-5 copies of a detargeting sequence.

The detargeting sequences may be inserted within the loop of the mature guide strand of the miRNA or at the 5' or 3' end of the mature guide strand of the miRNA. Exemplary locations for insertion of the detargeting sequences are set out in FIG. 4, and exemplary nucleic acids comprising the mature guide strand of miDUX4 (mi405 (SEQ ID NO: 10973) or mi1155 (SEQ ID NO: 10974) and the miR-122 binding site (SEQ ID NO: 5 or SEQ ID NO: 66) or the miR-208 binding site (SEQ ID NO: 6 or SEQ ID NO: 67) are provided in Table 1 below.

There are two miR-208 sequences in the human and mouse genome (miR-208a and miR-208b). To avoid a run of 5 U's (pol III promoter termination sequence), in the following exemplary sequences, a single base in the binding site was mutated to a "c" (lower-case bolded "c"). This change was included because it creates a perfect binding site for mir-208b, but will have a mismatch with mir-208a.

TABLE 1

| SEQ ID NO: | miDUX4 | miR binding site (underlined) | Location of binding site | Nucleotide Sequence (lower case letter - spacers to facilitate proper folding of the pre-miRNA stem) |
|---|---|---|---|---|
| 10913 | mi405 | miR-122 | Loop | CTCGAGTGAGCGATCCAGGATTCAGATCTGGTTTCTATT TAGTGTGATAATGGTGTTTAAACCAGATCTGAATCCTGG ACTGCCTACTAGT |
| 10914 | mi1155 | miR-122 | Loop | CTCGAGTGAGCGACAGGCGCAACCTCTCCTAGAATATTT AGTGTGATAATGGTGTTTCTAGGAGAGGTTGCGCCTGC TGCCTACTAGT |
| 10915 | mi405 | miR-122 | 5' end | CTCGAGTATTTAGTGTGATAATGGTGTTTctcggcTGAGC GATCCAGGATTCAGATCTGGTTTCTGAAAGCCACAGATG GGAAACCAGATCTGAATCCTGGACTGCCTACTAGT |
| 10916 | mi1155 | miR-122 | 5' end | CTCGAGTATTTAGTGTGATAATGGTGTTTctcggcTGAGC GACAGGCGCAACCTCTCCTAGAACTGTAAAGCCACAGAT GGGTTCTAGGAGAGGTTGCGCCTGCTGCCTACTAGT |
| 10917 | mi405 | miR-122 | 3' end | CTCGAGTGAGCGATCCAGGATTCAGATCTGGTTTCTGAA AGCCACAGATGGGAAACCAGATCTGAATCCTGGACTGC CTactagaTATTTAGTGTGATAATGGTGTTTACTAGT |
| 10918 | mi1155 | miR-122 | 3' end | CTCGAGTGAGCGACAGGCGCAACCTCTCCTAGAACTGTA AAGCCACAGATGGGTTCTAGGAGAGGTTGCGCCTGCTG CCTactagaTATTTAGTGTGATAATGGTGTTTACTAGT |
| 10919 | mi405 | miR-208 | Loop | CTCGAGTGAGCGATCCAGGATTCAGATCTGGTTTCTACG AGCcTTTTGCTCGTCTTATGGAAACCAGATCTGAATCCT GG ACTGCCTACTAGT |
| 10920 | mi1155 | miR-208 | Loop | CTCGAGTGAGCGACAGGCGCAACCTCTCCTAGAACTAC GAGCcTTTTGCTCGTCTTATGGTTCTAGGAGAGGTTGCG CCTGCTGCCTACTAGT |
| 10921 | mi405 | miR-208 | 5' end | CTCGAGACGAGCcTTTTGCTCGTCTTATctcggcTGAGCG ATCCAGGATTCAGATCTGGTTTCTGTAAAGCCACAGATG GGAAACCAGATCTGAATCCTGGACTGCCTACTAGT |
| 10922 | mi1155 | miR-208 | 5' end | CTCGAGACGAGCTTTTTGCTCGTCTTATctcggcTGAGCG ACAGGCGCAACCTCTCCTAGAACTGTAAAGCCACAGATG GGTTCTAGGAGAGGTTGCGCCTGCTGCCTACTAGT |
| 10923 | mi405 | miR-208 | 3' end | CTCGAGTGAGCGATCCAGGATTCAGATCTGGTTTCTGTA AAGCCACAGATGGGAAACCAGATCTGAATCCTGGACTG CCTactagaACGAGCcTTTTGCTCGTCTTATACTAGT |
| 10924 | mi1155 | miR-208 | 3' end | CTCGAGTGAGCGACAGGCGCAACCTCTCCTAGAACTGTA AAGCCACAGATGGGTTCTAGGAGAGGTTGCGCCTGCTG CCTactagaACGAGCcTTTTGCTCGTCTTATACTAGT |
| 10925 | mi405 | 5' miR-122, 3' miR-208 | | CTCGAGTATTTAGTGTGATAATGGTGTTTctcggcTGAGC GATCCAGGATTCAGATCTGGTTTCTGTAAAGCCACAGAT GGGAAACCAGATCTGAATCCTGGACTGCCTactagaACG AGCcTTTTGCTCGTCTTATACTAGT |
| 10926 | mi1155 | 5' miR-122, 3' miR-208 | | CTCGAGTATTTAGTGTGATAATGGTGTTTctcggcGAGC GACAGGCGCAACCTCTCCTAGAACTGTAAAGCCACAGAT GGGTTCTAGGAGAGGTTGCGCCTGCTGCCTactagaACG AGCcTTTTGCTCGTCTTATACTAGT |
| 10927 | mi405 | miR-122, miR-208 | 5' (both) | CTCGAGTATTTAGTGTGATAATGGTGTTTACGAGCcTTT TGCTCGTCTTATctcggcTGAGCGATCCAGGATTCAGATCT GGTTTCTGTAAAGCCACAGATGGGAAACCAGATCTGAA TCCTGGACTGCCTACTAGT |
| 10928 | mi1155 | miR-122, miR-208 | 5' (both) | CTCGAGTATTTAGTGTGATAATGGTGTTTACGAGCcTTT TGCTCGTCTTATctcggcTGAGCGACAGGCGCAACCTCTC CTAGAACTGTAAAGCCACAGATGGGTTCTAGGAGAGGT TGCGCCTGCTGCCTACTAGT |
| 10929 | mi405 | miR-122, miR-208 | 3' (both) | CTCGAGTGAGCGATCCAGGATTCAGATCTGGTTTCTGTA AAGCCACAGATGGGAAACCAGATCTGAATCCTGGACTG CCTactagaTATTTAGTGTGATAATGGTGTTTACGAGCcT TTTGCTCGTCTTATACTAGT |
| 10930 | mi1155 | miR-122, miR-208 | 3' (both) | CTCGAGTGAGCGACAGGCGCAACCTCTCCTAGAACTGTA AAGCCACAGATGGGTTCTAGGAGAGGTTGCGCCTGCTG |

TABLE 1-continued

| SEQ ID NO: | miDUX4 | miR binding site (underlined) | Location of binding site | Nucleotide Sequence (lower case letter - spacers to facilitate proper folding of the pre-miRNA stem) |
|---|---|---|---|---|
| | | | | CCTactagaTATTTAGTGTGATAAATGGTGTTTACGAGCcTTTTGCTCGTCTTATACTAGT |
| 10931 | mi405 | miR-122 loop, 5' miR-208 | | CTCGAGACGAGCcTTTTGCTCGTCTTATctcgggTGAGCGATCCAGGATTCAGATCTGGTTTCTTATTTAGTGTGATAATGGTGTTTGGAAACCAGATCTGAATCCTGGACTGCCTACTAGT |
| 10932 | mi1155 | miR-122 loop, 5' miR-208 | | CTCGAGACGAGCcTTTTGCTCGTCTTATctcgggTGAGCGACAGGCGCAACCTCTCCTAGAACTTATTTAGTGTGATAATGGTGTTTGGTTCTAGGAGAGGTTGCGCCTGCTGCCTACTAGT |
| 10933 | mi405 | miR-122 Loop, 3' miR-208 | | CTCGAGTGAGCGATCCAGGATTCAGATCTGGTTTCTTATTTAGTGTGATAATGGTGTTTGGAAACCAGATCTGAATCCTGGACTGCCTactagaACGAGCcTTTTGCTCGTCTTATACTAGT |
| 10934 | mi1155 | miR-122 Loop, 3' miR-208 | | CTCGAGTGAGCGACAGGCGCAACCTCTCCTAGAACTTATTTAGTGTGATAATGGTGTTTGGTTCTAGGAGAGGTTGCCTGCTGCCTactagaACGAGCcTTTTGCTCGTCTTATACTAGT |
| 10935 | mi405 | miR-208 loop, 5' miR-122 | | CTCGAGTATTTAGTGTGATAATGGTGTTctcgggTGAGCGATCCAGGATTCAGATCTGGTTTCTACGAGCcTTTTGCTCGTCTTATGGAAACCAGATCTGAATCCTGGACTGCCTACTAGT |
| 10936 | mi1155 | miR-208 loop, 5' miR-122 | | CTCGAGTATTTAGTGTGATAATGGTGTTTctcgggTGAGCGACAGGCGCAACCTCTCCTAGAACTACGAGCcTTTTGCTCGTCTTATGGTTCTAGGAGAGGTTGCGCCTGCTGCCTACTAGT |
| 10937 | mi405 | miR-208 loop, 3' miR-122 | | CTCGAGTGAGCGATCCAGGATTCAGATCTGGTTTCTACGAGCcTTTTGCTCGTCTTATGGAAACCAGATCTGAATCCTGGACTGCCTactagaTATTTAGTGTGATAATGGTGTTTACTAGT |
| 10938 | mi1155 | miR-208 loop, 3' miR-122 | | CTCGAGTGAGCGACAGGCGCAACCTCTCCTAGAACTACGAGCcTTTTGCTCGTCTTATGGTTCTAGGAGAGGTTGCGCCTGCTGCCTactagaTATTTAGTGTGATAATGGTGTTTACTAGT |
| 10939 | mi405 | miR-122 / miR-122 | Loop (both) | CTCGAGTGAGCGATCCAGGATTCAGATCTGGTTTCTTTTAGTGTGATAATGGTGTTTGACGAGCTTTTTGCTCGTCTTATGGAAACCAGATCTGAATCCTGGACTGCCTACTAGT |
| 10940 | mi1155 | miR-122 / miR-122 | Loop (both) | CTCGAGTGAGCGACAGGCGCAACCTCTCCTAGAACTTTTAGTGTGATAATGGTGTTTGACGAGCTTTTTGCTCGTCTTATGGTTCTAGGAGAGGTTGCGCCTGCTGCCTACTAGT |
| 10941 | mi405 | miR-122 | Loop | CUCGAGUGAGCGAUCCAGGAUUCAGAUCUGGUUUCUUAUUUAGUGUGAUAAUGGUGUUUAAACCAGAUCUGAAUCCUGGACUGCCUACUAGU |
| 10942 | mi1155 | miR-122 | Loop | CUCGAGUGAGCGACAGGCGCAACCUCUCCUAGAAUAUUUAGUGUGAUAAUGGUGUUUCUAGGAGAGGUUGCGCCUGCUGCCUACUAGU |
| 10943 | mi405 | miR-122 | 5' end | CUCGAGUAUUUAGUGUGAUAAUGGUGUUUcUcgggUGAGCGAUCCAGGAUUCAGAUCUGGUUUCUGAAAGCCACAGAUGGGAAACCAGAUCUGAAUCCUGGACUGCCUACUAGU |
| 10944 | mi1155 | miR-122 | 5' end | CUCGAGUAUUUAGUGUGAUAAUGGUGUUUcUcgggUGAGCGACAGGCGCAACCUCUCCUAGAACUGUAAAGCCACAGAUGGGUUCUAGGAGAGGUUGCGCCUGCUGCCUACUAGU |
| 10945 | mi405 | miR-122 | 3' end | CUCGAGUGAGCGAUCCAGGAUUCAGAUCUGGUUUCUGAAAGCCACAGAUGGGAAACCAGAUCUGAAUCCUGGACUGCCUacUagaUAUUUAGUGUGAUAAUGGUGUUUACUAGU |

TABLE 1-continued

| SEQ ID NO: | miDUX4 | miR binding site (underlined) | Location of binding site | Nucleotide Sequence (lower case letter - spacers to facilitate proper folding of the pre-miRNA stem) |
|---|---|---|---|---|
| 10946 | mi1155 | miR-122 | 3' end | CUCGAGUGAGCGACAGGCGCAACCUCUCCUAGAACUG UAAAGCCACAGAUGGGUUCUAGGAGAGGUUGCGCCU GCUGCCUacUagaUAUUUAGUGUGAUAAUGGGUGUUU ACUAGU |
| 10947 | mi405 | miR-208 | Loop | CUCGAGUGAGCGAUCCAGGAUUCAGAUCUGGUUUCU ACGAGCcUUUUGCUCGUCUUAUGGAAACCAGAUCUG AAUCCUGGACUGCCUACUAGU |
| 10948 | mi1155 | miR-208 | Loop | CUCGAGUGAGCGACAGGCGCAACCUCUCCUAGAACUA CGAGCcUUUUGCUCGUCUUAUGGUUCUAGGAGAGG UUGCGCCUGCUGCCUACUAGU |
| 10949 | mi405 | m i R-208 | 5' end | CUCGAGACGAGCcUUUUGCUCGUCUUAUcUcgggUGA GCGAUCCAGGAUUCAGAUCUGGUUUCUGUAAAGCCA CAGAUGGGAAACCAGAUCUGAAUCCUGGACUGCCUAC UAGU |
| 10950 | mi405 | miR-208 | 5' end | CUCGAGACGAGCUUUUUGCUCGUCUUAUcUcgggUGA GCGACAGGCGCAACCUCUCCUAGAACUGUAAAGCCAC AGAUGGGUUCUAGGAGAGGUUGCGCCUGCUGCCUAC UAGU |
| 10951 | mi405 | miR-208 | 3' end | CUCGAGUGAGCGAUCCAGGAUUCAGAUCUGGUUUCU GUAAAGCCACAGAUGGGAAACCAGAUCUGAAUCCUG GACUGCCUacUagaACGAGCcUUUUGCUCGUCUUAUA CUAGU |
| 10952 | mi1155 | miR-208 | 3' end | CUCGAGUGAGCGACAGGCGCAACCUCUCCUAGAACUG UAAAGCCACAGAUGGGUUCUAGGAGAGGUUGCGCCU GCUGCCUacUagaACGAGCcUUUUGCUCGUCUUAUAC UAGU |
| 10953 | mi405 | 5' miR-122, 3' miR-208 | | CUCGAGUAUUUAGUGUGAUAAUGGGUGUUUcUcgggU GAGCGAUCCAGGAUUCAGAUCUGGUUUCUGUAAAGC CACAGAUGGGAAACCAGAUCUGAAUCCUGGACUGCCU acUagaACGAGCcUUUUGCUCGUCUUAUACUAGU |
| 10954 | mi1155 | 5' miR-122, 3' miR-208 | | CUCGAGUAUUUAGUGUGAUAAUGGGUGUUUcUcgggU GAGCGACAGGCGCAACCUCUCCUAGAACUGUAAAGCC ACAGAUGGGUUCUAGGAGAGGUUGCGCCUGCUGCCU acUagaACGAGCcUUUUGCUCGUCUUAUACUAGU |
| 10955 | mi405 | miR-122, miR-208 | 5' (both) | CUCGAGUAUUUAGUGUGAUAAUGGGUGUUUACGAGC cUUUUGCUCGUCUUAUcUcgggUGAGCGAUCCAGGAU UCAGAUCUGGUUUCUGUAAAGCCACAGAUGGGAAAC CAGAUCUGAAUCCUGGACUGCCUACUAGU |
| 10956 | mi1155 | miR-122, miR-208 | 5' (both) | CUCGAGUAUUUAGUGUGAUAAUGGGUGUUUACGAGC cUUUUGCUCGUCUUAUcUcgggUGAGCGACAGGCGCA ACCUCUCCUAGAACUGUAAAGCCACAGAUGGGUUCUA GGAGAGGUUGCGCCUGCUGCCUACUAGU |
| 10957 | mi405 | miR-122, miR-208 | 3' (both) | CUCGAGUGAGCGAUCCAGGAUUCAGAUCUGGUUUCU GUAAAGCCACAGAUGGGAAACCAGAUCUGAAUCCUG GACUGCCUacUagaUAUUUAGUGUGAUAAUGGGUGUU UACGAGCcUUUUGCUCGUCUUAUACUAGU |
| 10958 | mi1155 | miR-122, miR-208 | 3' (both) | CUCGAGUGAGCGACAGGCGCAACCUCUCCUAGAACUG UAAAGCCACAGAUGGGUUCUAGGAGAGGUUGCGCCU GCUGCCUacUagaUAUUUAGUGUGAUAAUGGGUGUUU ACGAGCcUUUUGCUCGUCUUAUACUAGU |
| 10959 | mi405 | miR-122 Loop, 5' miR-208 | | CUCGAGACGAGCcUUUUGCUCGUCUUAUcUcgggUGA GCGAUCCAGGAUUCAGAUCUGGUUUCUUAUUUAGU GUGAUAAUGGGUGUUUGGAAACCAGAUCUGAAUCCU GGACUGCCUACUAGU |
| 10960 | mi1155 | miR-122 Loop, 5' miR-208 | | CUCGAGACGAGCcUUUUGCUCGUCUUAUcUcgggUGA GCGACAGGCGCAACCUCUCCUAGAACUUAUUUAGUG UGAUAAUGGGUGUUUGGUUCUAGGAGAGGUUGCGCC UGCUGCCUACUAGU |

TABLE 1-continued

| SEQ ID NO: | miDUX4 | miR binding site (underlined) | Location of binding site | Nucleotide Sequence (lower case letter - spacers to facilitate proper folding of the pre-miRNA stem) |
|---|---|---|---|---|
| 10961 | mi405 | miR-122 Loop, 3' miR-208 | | CUCGAGUGAGCGAUCCAGGAUUCAGAUCUGGUUUCU UAUUUAGUGUGAUAAUGGUGUUUGGAAACCAGAUC UGAAUCCUGGACUGCCUacUagaACGAGCcUUUUGCU CGUCUUAUACUAGU |
| 10962 | mi1155 | miR-122 Loop, 3' miR-208 | | CUCGAGUGAGCGACAGGCGCAACCUCUCCUAGAACUU AUUUAGUGUGAUAAUGGUGUUUGGUUCUAGGAGA GGUUGCGCCUGCUGCCUacUagaACGAGCcUUUUGCU CGUCUUAUACUAGU |
| 10963 | mi405 | miR-208 Loop, 5' miR-122 | | CUCGAGUAUUUAGUGUGAUAAUGGUGUUUcUcgggU GAGCGAUCCAGGAUUCAGAUCUGGUUUCUACGAGCc UUUUGCUCGUCUUAUGGAAACCAGAUCUGAAUCCUG GACUGCCUACUAGU |
| 10964 | mi1155 | miR-208 loop, 5' miR-122 | | CUCGAGUAUUUAGUGUGAUAAUGGUGUUUcUcgggU GAGCGACAGGCGCAACCUCUCCUAGAACUACGAGCcU UUUGCUCGUCUUAUGGUUCUAGGAGAGGUUGCGCC UGCUGCCUACUAGU |
| 10965 | mi405 | miR-208 loop, 3' miR-122 | | CUCGAGUGAGCGAUCCAGGAUUCAGAUCUGGUUUCU ACGAGCcUUUUGCUCGUCUUAUGGAAACCAGAUCUG AAUCCUGGACUGCCUacUagaUAUUUAGUGUGAUAA UGGUGUUUACUAGU |
| 10966 | mi1155 | miR-208 loop, 3' miR-122 | | CUCGAGUGAGCGACAGGCGCAACCUCUCCUAGAACUA CGAGCcUUUUGCUCGUCUUAUGGUUCUAGGAGAGG UUGCGCCUGCUGCCUacUagaUAUUUAGUGUGAUAA UGGUGUUUACUAGU |
| 10967 | mi405 | miR-122 miR-122 | Loop (both) | CUCGAGUGAGCGAUCCAGGAUUCAGAUCUGGUUUCU UUUAGUGUGAUAAUGGUGUUUGACGAGCUUUUUG CUCGUCUUAUGGAAACCAGAUCUGAAUCCUGGACUG CCUACUAGU |
| 10968 | mi1155 | miR-122 miR-122 | Loop (both) | CUCGAGUGAGCGACAGGCGCAACCUCUCCUAGAACUU UUAGUGUGAUAAUGGUGUUUGACGAGCUUUUUGC UCGUCUUAUGGUUCUAGGAGAGGUUGCGCCUGCUG CCUACUAGU |

The mature guide stand of a miRNA comprising a nucleotide sequence of mi70 (SEQ ID NO: 8482), mi180 (SEQ ID NO: 8372), mi181(SEQ ID NO: 8371), mi182 (SEQ ID NO: 8370), mi185 (SEQ ID NO: 8367), mi186 (SEQ ID NO: 8366), mi187 (SEQ ID NO: 8365), mi333 (SEQ ID NO: 8219), mi334 (SEQ ID NO: 8218), mi400 (SEQ ID NO: 8152), mi405 (SEQ ID NO: 8147), mi407 (SEQ ID NO: 8145), mi1155 (SEQ ID NO: 7397), mi1156 (SEQ ID NO: 7396), mi1157 (SEQ ID NO: 7395), mi1308 (SEQ ID NO: 7108), mi1309 (SEQ ID NO: 7107), mi1310 (SEQ ID NO: 7106), mi1420 (SEQ ID NO: 6633), mi1422 (SEQ ID NO: 6631), mi1431 (SEQ ID NO: 6622), mi1434 (SEQ ID NO: 6619), mi1444 (SEQ ID NO: 6609), mi1445 (SEQ ID NO: 6608), mi1485 (SEQ ID NO: 6568), mi1492 (SEQ ID NO: 6561), mi1493 (SEQ ID NO: 6560), mi1519 ((SEQ ID NO: 10971) or mi1520 (SEQ ID NO: 10972) may be used. These sequences fold similarly to mature guide stands of mi405 and mi1155 fold similarly to the mature guide strands of mir405 and mir1155. Therefore, the disclosure provides for nucleic acid molecules in which the mir-208 bind site sequence (SEQ ID NO: 5 or SEQ ID NO: 66) and/or the mir-122 binding site sequence (SEQ ID NO: 6 or SEQ ID NO: 67) may be inserted into the loop of any of the foregoing mature guide strands at locations similar to those set out in the sequences in Table 1.

miRNA of Interest

The nucleic acid molecules of the disclosure may comprise the sequence of the mature guide strand of any miRNA transcript sequence desired to have tissue-specific expression. For example, in one embodiment, skeletal expression of DUX4 miRNA is contemplated. Exemplary DUX4 miRNA sequences are provided in International Patent Application No. PCT/US2012/047999 (WO 2013/016352) and US patent publication no. US 201220225034 incorporated by reference herein in their entirety.

Two examples of miDUX4 are miDUX4-1 (miDux405; SEQ ID NO: 1): and miDUX4-2 (miDux1155; SEQ ID NO: 2). Exemplary nucleotide sequences comprising the DUX4 miRNA and the binding site for either miR-122 or miR-208 are provided in Table 1 and SEQ ID NOS: 10913-10968.

Any human miRNA may be expressed using the nucleic acid molecules of the disclosure , including those set out in the miRBase: the microRNA database websites (miRBase-.org), which are incorporated by reference herein in its entirety. Examples include but not limited to the following: miR-122, miR-124, miR-142, miR-155, miR-21, miR-17-92, miR-17, miR-18a, miR-19a, miR-20a, miR-19b-1, miR-26a, miR-126, miR-335, let-7 family: let-7a and let-7b, miR-34 (miR-34a), miR-10b, miR-208, miR-499, miR-195, miR-29a, miR-29b, and miR-29c. Additional exemplary miRNA are set out below in Table 2. Any of these miRNA may be used with different detargeting sequences, depending of the desired tissue specificity and desired detargeting.

TABLE 2

| miRNA ID | Accession | RPM | Chromosome | Start | End | Strand | Confidence |
|---|---|---|---|---|---|---|---|
| hsa-mir-99b | MI0000746 | 1742 | chr19 | 51692612 | 51692681 | + | ✓ |
| hsa-mir-99a | MI0000101 | 26393 | chr21 | 16539089 | 16539169 | + | ✓ |
| hsa-mir-9986 | MI0032316 | — | chr2 | 132433711 | 132433820 | + | — |
| hsa-mir-9985 | MI0032313 | 1873 | chrY | 4606120 | 4606228 | + | ✓ |
| hsa-mir-9983 | MI0033670 | 3 | chr6 | 39074314 | 39074381 | + | — |
| hsa-mir-9903 | MI0031831 | 1 | chr8 | 98393645 | 98393738 | − | ✓ |
| hsa-mir-9902-2 | MI0041071 | 406 | chr12 | 122709332 | 122709424 | − | — |
| hsa-mir-9902-1 | MI0031830 | 406 | chr12 | 122695907 | 122695999 | − | — |
| hsa-mir-9901 | MI0031829 | 13 | chr16 | 34163578 | 34163673 | + | — |
| hsa-mir-9900 | MI0031828 | — | chr3 | 112737089 | 112737181 | + | — |
| hsa-mir-9899 | MI0031827 | — | chr2 | 149330278 | 149330373 | − | — |
| hsa-mir-9898 | MI0031826 | 3 | chr12 | 52898889 | 52898984 | − | — |
| hsa-mir-9851 | MI0039502 | — | chr10 | 116827488 | 116827568 | − | — |
| hsa-mir-98 | MI0000100 | 45139 | chrX | 53556223 | 53556341 | − | ✓ |
| hsa-mir-9718 | MI0030983 | — | chr14 | 60648648 | 60648711 | + | — |
| hsa-mir-96 | MI0000098 | 483 | chr7 | 129774692 | 129774769 | − | ✓ |
| hsa-mir-9500 | MI0029185 | — | chr2 | 218823090 | 218823154 | + | — |
| hsa-mir-95 | MI0000097 | 164 | chr4 | 8005301 | 8005381 | − | — |
| hsa-mir-944 | MI0005769 | 80 | chr3 | 189829922 | 189830009 | + | — |
| hsa-mir-943 | MI0005768 | — | chr4 | 1986384 | 1986477 | − | — |
| sa-mir-942 | MI0005767 | 2 | chr1 | 117094643 | 117094728 | + | ✓ |
| hsa-mir-941-5 | MI0031520 | 57 | chr20 | 63919868 | 63919939 | + | ✓ |
| hsa-mir-941-4 | MI0005766 | 57 | chr20 | 63919756 | 63919827 | + | ✓ |
| hsa-mir-941-3 | MI0005765 | 57 | chr20 | 63919561 | 63919632 | + | ✓ |
| hsa-mir-941-2 | MI0005764 | 57 | chr20 | 63919505 | 63919576 | + | ✓ |
| hsa-mir-941-1 | MI0005763 | 57 | chr20 | 63919449 | 63919520 | + | ✓ |
| hsa-mir-940 | MI0005762 | — | chr16 | 2271747 | 2271840 | + | — |
| hsa-mir-939 | MI0005761 | — | chr8 | 144394149 | 144394230 | − | — |
| hsa-mir-938 | MI0005760 | 53 | chr10 | 29602264 | 29602346 | − | — |
| hsa-mir-937 | MI0005759 | 18 | chr8 | 143812957 | 143813042 | − | — |
| hsa-mir-936 | MI0005758 | — | chr10 | 104048089 | 104048186 | − | — |
| hsa-mir-935 | MI0005757 | 11 | chr19 | 53982307 | 53982397 | + | — |
| hsa-mir-934 | MI0005756 | 5 | chrX | 136550878 | 136550960 | + | — |
| hsa-mir-933 | MI0005755 | — | chr2 | 175167633 | 175167709 | − | — |
| hsa-mir-93 | MI0000095 | 2001 | chr7 | 100093768 | 100093847 | − | ✓ |
| hsa-mir-92b | MI0003560 | 4600 | chr1 | 155195177 | 155195272 | + | ✓ |
| hsa-mir-92a-2 | MI0000094 | 7185 | chrX | 134169538 | 134169612 | − | ✓ |
| hsa-mir-92a-1 | MI0000093 | 8600 | chr13 | 91351314 | 91351391 | + | ✓ |
| hsa-mir-924 | MI0005716 | 100 | chr18 | 39622123 | 39622175 | − | — |

TABLE 2-continued

| miRNA ID | Accession | RPM | Chromosome | Start | End | Strand | Confidence |
|----------|-----------|-----|------------|-------|-----|--------|------------|
| hsa-mir-922 | MI0005714 | 17 | chr3 | 197674496 | 197674576 | − | − |
| hsa-mir-921 | MI0005713 | − | chr1 | 166154743 | 166154798 | − | − |
| hsa-mir-920 | MI0005712 | − | chr12 | 24212421 | 24212495 | + | − |
| hsa-mir-9-3 | MI0000468 | 1073 | chr15 | 89368017 | 89368106 | + | ✓ |
| hsa-mir-9-2 | MI0000467 | 1073 | chr5 | 88666853 | 88666939 | − | ✓ |
| hsa-mir-9-1 | MI0000466 | 1073 | chr1 | 156420341 | 156420429 | − | ✓ |
| hsa-mir-892c | MI0022560 | 2 | chrX | 145992750 | 145992826 | − | − |
| hsa-mir-892b | MI0005538 | − | chrX | 145997198 | 145997274 | − | − |
| hsa-mir-892a | MI0005528 | − | chrX | 145996669 | 145996743 | − | − |
| hsa-mir-891b | MI0005534 | − | chrX | 146001053 | 146001131 | − | − |
| hsa-mir-891a | MI0005524 | − | chrX | 146027794 | 146027872 | − | − |
| hsa-mir-890 | MI0005533 | 2 | chrX | 145994275 | 145994351 | − | − |
| hsa-mir-889 | MI0005540 | 26 | chr14 | 101047901 | 101047979 | + | ✓ |
| hsa-mir-888 | MI0005537 | 784 | chrX | 145994784 | 145994860 | − | ✓ |
| hsa-mir-887 | MI0005562 | 6 | chr5 | 15935182 | 15935260 | + | ✓ |
| hsa-mir-885 | MI0005560 | 4 | chr3 | 10394489 | 10394562 | − | ✓ |
| hsa-mir-877 | MI0005561 | 70 | chr6 | 30584332 | 30584417 | + | − |
| hsa-mir-876 | MI0005542 | 28 | chr9 | 28863626 | 28863706 | − | ✓ |
| hsa-mir-875 | MI0005541 | − | chr8 | 99536786 | 99536861 | − | − |
| hsa-mir-874 | MI0005532 | 23 | chr5 | 137647572 | 137647649 | − | ✓ |
| hsa-mir-873 | MI0005564 | 8 | chr9 | 28888879 | 28888955 | − | ✓ |
| hsa-mir-8485 | MI0027288 | 1000 | chr2 | 50696172 | 50696262 | − | − |
| hsa-mir-8089 | MI0025925 | 28 | chr5 | 181043403 | 181043484 | − | − |
| hsa-mir-8088 | MI0025924 | − | chrX | 52336557 | 52336642 | − | − |
| hsa-mir-8087 | MI0025923 | 65 | chr11 | 27514970 | 27515047 | − | − |
| hsa-mir-8086 | MI0025922 | 209 | chr10 | 28289258 | 28289350 | − | − |
| hsa-mir-8085 | MI0025921 | − | chr19 | 44758657 | 44758721 | + | − |
| hsa-mir-8084 | MI0025920 | − | chr8 | 93029751 | 93029839 | + | − |
| hsa-mir-8083 | MI0025919 | − | chr1 | 153689705 | 153689793 | − | − |
| hsa-mir-8082 | MI0025918 | − | chr4 | 113152282 | 113152362 | + | − |
| hsa-mir-8081 | MI0025917 | 472 | chr9 | 106600928 | 106601022 | + | − |
| hsa-mir-8080 | MI0025916 | 15 | chr2 | 79866495 | 79866583 | − | − |
| hsa-mir-8079 | MI0025915 | − | chr13 | 44196129 | 44196200 | − | − |
| hsa-mir-8078 | MI0025914 | − | chr18 | 112256 | 112339 | − | − |
| hsa-mir-8077 | MI0025913 | − | chr19 | 42351131 | 42351205 | + | − |
| hsa-mir-8076 | MI0025912 | − | chr3 | 113432118 | 113432200 | − | − |
| hsa-mir-8075 | MI0025911 | − | chr13 | 113262920 | 113262999 | + | − |
| hsa-mir-8074 | MI0025910 | − | chr19 | 51206929 | 51207009 | − | − |
| hsa-mir-8073 | MI0025909 | − | chr13 | 110340958 | 110341029 | + | − |

TABLE 2-continued

| miRNA ID | Accession | RPM | Chromosome | Start | End | Strand | Confidence |
|---|---|---|---|---|---|---|---|
| hsa-mir-8072 | MI0025908 | 5 | chr12 | 123364764 | 123364843 | − | − |
| hsa-mir-8071-2 | MI0026417 | − | chr14 | 105640168 | 105640232 | + | − |
| hsa-mir-8071-1 | MI0025907 | − | chr14 | 105621116 | 105621180 | + | − |
| hsa-mir-8070 | MI0025906 | − | chr11 | 11783135 | 11783222 | − | − |
| hsa-mir-8069-2 | MI0031519 | 12 | chr21 | 13724189 | 13724274 | + | − |
| hsa-mir-8069-1 | MI0025905 | 12 | chr21 | 6859171 | 6859256 | + | − |
| hsa-mir-8068 | MI0025904 | − | chr11 | 28477481 | 28477548 | − | − |
| hsa-mir-8067 | MI0025903 | − | chr15 | 62304658 | 62304734 | − | − |
| hsa-mir-8066 | MI0025902 | − | chr4 | 101240795 | 101240872 | − | − |
| hsa-mir-8065 | MI0025901 | 180 | chr16 | 5632467 | 5632566 | + | − |
| hsa-mir-8064 | MI0025900 | 3 | chr3 | 52846463 | 52846552 | − | − |
| hsa-mir-8063 | MI0025899 | − | chr15 | 36972821 | 36972901 | − | − |
| hsa-mir-8062 | MI0025898 | − | chr20 | 7371608 | 7371692 | + | − |
| hsa-mir-8061 | MI0025897 | − | chr19 | 54645309 | 54645383 | + | − |
| hsa-mir-8060 | MI0025896 | − | chr3 | 96359964 | 96360039 | + | − |
| hsa-mir-8059 | MI0025895 | − | chr17 | 50768650 | 50768730 | + | − |
| hsa-mir-8058 | MI0025894 | 8 | chr16 | 82688931 | 82689019 | + | − |
| hsa-mir-8057 | MI0025893 | 5 | chr18 | 26591467 | 26591535 | − | − |
| hsa-mir-8056 | MI0025892 | − | chr5 | 173347455 | 173347536 | + | − |
| hsa-mir-8055 | MI0025891 | − | chr8 | 6622124 | 6622220 | − | − |
| hsa-mir-8054 | MI0025890 | − | chr11 | 23419105 | 23419190 | − | − |
| hsa-mir-8053 | MI0025889 | − | chr4 | 47652669 | 47652743 | + | − |
| hsa-mir-8052 | MI0025888 | − | chr11 | 130666735 | 130666803 | + | − |
| hsa-mir-802 | MI0003906 | 266 | chr21 | 35720715 | 35720808 | + | − |
| hsa-mir-7978 | MI0025754 | − | chr4 | 21464700 | 21464758 | − | − |
| hsa-mir-7977 | MI0025753 | 58 | chr3 | 176515103 | 176515151 | + | − |
| hsa-mir-7976 | MI0025752 | − | chr3 | 127587111 | 127587176 | − | ✓ |
| hsa-mir-7975 | MI0025751 | 121 | chr19 | 55123225 | 55123292 | − | − |
| hsa-mir-7974 | MI0025750 | 21 | chr19 | 11495544 | 11495622 | − | − |
| hsa-mir-7973-2 | MI0025749 | − | chr15 | 51314032 | 51314107 | − | − |
| hsa-mir-7973-1 | MI0025748 | − | chr15 | 51314034 | 51314109 | + | − |
| hsa-mir-7856 | MI0025526 | − | chr1 | 86357632 | 86357687 | − | − |
| hsa-mir-7855 | MI0025525 | 35 | chr14 | 64785626 | 64785686 | − | − |
| hsa-mir-7854 | MI0025524 | − | chr16 | 81533902 | 81533966 | + | − |
| hsa-mir-7853 | MI0025523 | 11 | chr6 | 6169304 | 6169435 | − | − |
| hsa-mir-7852 | MI0025522 | − | chr1 | 107897223 | 107897304 | + | − |
| hsa-mir-7851 | MI0025521 | 837 | chr12 | 42323700 | 42323859 | − | − |
| hsa-mir-7850 | MI0025520 | 64 | chr19 | 2630715 | 2630793 | + | − |
| hsa-mir-7849 | MI0025519 | − | chr4 | 146408583 | 146408688 | + | − |

TABLE 2-continued

| miRNA ID | Accession | RPM | Chromosome | Start | End | Strand | Confidence |
|---|---|---|---|---|---|---|---|
| hsa-mir-7848 | MI0025518 | — | chr8 | 133046481 | 133046581 | − | — |
| hsa-mir-7847 | MI0025517 | 24 | chr11 | 1880045 | 1880147 | + | — |
| hsa-mir-7846 | MI0025516 | 4 | chr1 | 12166943 | 12167038 | + | — |
| hsa-mir-7845 | MI0025515 | 4 | chr2 | 207166400 | 207166498 | + | — |
| hsa-mir-7844 | MI0025514 | — | chr12 | 94571231 | 94571352 | − | — |
| hsa-mir-7843 | MI0025510 | — | chr14 | 72516820 | 72516898 | + | — |
| hsa-mir-7706 | MI0025242 | 1 | chr15 | 85380596 | 85380662 | + | — |
| hsa-mir-7705 | MI0025241 | — | chr8 | 100702968 | 100703024 | − | — |
| hsa-mir-7704 | MI0025240 | 29 | chr2 | 176188843 | 176188901 | + | — |
| hsa-mir-7703 | MI0025239 | 4 | chr14 | 24143489 | 24143565 | − | — |
| hsa-mir-7702 | MI0025238 | — | chr9 | 111271156 | 111271214 | − | — |
| hsa-mir-770 | MI0005118 | — | chr14 | 100852390 | 100852487 | + | ✓ |
| hsa-mir-769 | MI0003834 | 120 | chr19 | 46018932 | 46019049 | + | ✓ |
| hsa-mir-767 | MI0003763 | 30 | chrX | 152393421 | 152393529 | − | ✓ |
| hsa-mir-766 | MI0003836 | 10 | chrX | 119646738 | 119646848 | − | ✓ |
| hsa-mir-765 | MI0005116 | 8 | chr1 | 156936131 | 156936244 | − | — |
| hsa-mir-764 | MI0003944 | — | chrX | 114639435 | 114639519 | + | — |
| hsa-mir-762 | MI0003892 | — | chr16 | 30893903 | 30893985 | + | — |
| hsa-mir-761 | MI0003941 | 40 | chr1 | 51836344 | 51836402 | − | — |
| hsa-mir-760 | MI0005567 | 9 | chr1 | 93846832 | 93846911 | + | — |
| hsa-mir-759 | MI0004065 | — | chr13 | 52810050 | 52810140 | + | — |
| hsa-mir-758 | MI0003757 | 2 | chr14 | 101026020 | 101026107 | + | ✓ |
| hsa-mir-7515 | MI0024354 | 20 | chr2 | 6650373 | 6650439 | + | — |
| hsa-mir-744 | MI0005559 | 324 | chr17 | 12081899 | 12081996 | + | ✓ |
| hsa-mir-718 | MI0012489 | 2 | chrX | 154019920 | 154019989 | − | — |
| hsa-mir-7162 | MI0023623 | — | chr10 | 30368597 | 30368665 | − | — |
| hsa-mir-7161 | MI0023619 | 107 | chr6 | 158609707 | 158609790 | + | — |
| hsa-mir-7160 | MI0023621 | — | chr8 | 2076589 | 2076640 | + | — |
| hsa-mir-7159 | MI0023620 | 50 | chr6 | 33899135 | 33899200 | + | — |
| hsa-mir-7158 | MI0023618 | — | chr2 | 5974662 | 5974732 | + | — |
| hsa-mir-7157 | MI0023617 | — | chr2 | 140586626 | 140586685 | − | — |
| hsa-mir-7156 | MI0023616 | — | chr1 | 77060143 | 77060202 | + | — |
| hsa-mir-7155 | MI0023615 | — | chr11 | 64341849 | 64341904 | − | — |
| hsa-mir-7154 | MI0023614 | — | chr11 | 45691704 | 45691776 | − | ✓ |
| hsa-mir-7153 | MI0023613 | — | chr18 | 11654885 | 11654941 | − | — |
| hsa-mir-7152 | MI0023612 | — | chr10 | 71790747 | 71790800 | + | — |
| hsa-mir-7151 | MI0023611 | — | chr10 | 67403351 | 67403410 | − | — |
| hsa-mir-7150 | MI0023610 | — | chr9 | 123485529 | 123485622 | − | — |
| hsa-mir-7114 | MI0022965 | — | chr9 | 137450026 | 137450086 | − | — |

TABLE 2-continued

| miRNA ID | Accession | RPM | Chromosome | Start | End | Strand | Confidence |
|---|---|---|---|---|---|---|---|
| hsa-mir-7113 | MI0022964 | — | chr11 | 68032864 | 68032922 | + | — |
| hsa-mir-7112 | MI0022963 | — | chr8 | 144262673 | 144262737 | − | — |
| hsa-mir-7111 | MI0022962 | — | chr6 | 35470508 | 35470579 | + | — |
| hsa-mir-7110 | MI0022961 | 578 | chr3 | 123161794 | 123161879 | + | — |
| hsa-mir-711 | MI0012488 | — | chr3 | 48578902 | 48578977 | − | — |
| hsa-mir-7109 | MI0022960 | 2 | chr22 | 31621467 | 31621531 | − | — |
| hsa-mir-7108 | MI0022959 | 100 | chr19 | 2434914 | 2435000 | − | — |
| hsa-mir-7107 | MI0022958 | 13 | chr12 | 121444273 | 121444352 | − | — |
| hsa-mir-7106 | MI0022957 | — | chr12 | 113159113 | 113159177 | − | — |
| hsa-mir-708 | MI0005543 | 184 | chr11 | 79402022 | 79402109 | − | ✓ |
| hsa-mir-7-3 | MI0000265 | 3279 | chr19 | 4770670 | 4770779 | + | — |
| hsa-mir-7-2 | MI0000264 | 3265 | chr15 | 88611825 | 88611934 | + | ✓ |
| hsa-mir-7-1 | MI0000263 | 3664 | chr9 | 83969748 | 83969857 | − | ✓ |
| hsa-mir-6895 | MI0022742 | 4 | chrX | 53195411 | 53195488 | − | — |
| hsa-mir-6894 | MI0022741 | 1 | chrX | 53198889 | 53198945 | − | — |
| hsa-mir-6893 | MI0022740 | — | chr8 | 144435551 | 144435619 | − | — |
| hsa-mir-6892 | MI0022739 | 35 | chr7 | 143382686 | 143382800 | + | — |
| hsa-mir-6891 | MI0022738 | 12 | chr6 | 31355224 | 31355316 | − | — |
| hsa-mir-6890 | MI0022737 | — | chr3 | 49099854 | 49099914 | − | — |
| hsa-mir-6889 | MI0022736 | — | chr22 | 41252992 | 41253050 | − | — |
| hsa-mir-6888 | MI0022735 | 2 | chr2 | 159186835 | 159186901 | + | — |
| hsa-mir-6887 | MI0022734 | — | chr19 | 35122700 | 35122764 | + | — |
| hsa-mir-6886 | MI0022733 | — | chr19 | 11113474 | 11113534 | + | — |
| hsa-mir-6885 | MI0022732 | — | chr19 | 6389638 | 6389703 | − | — |
| hsa-mir-6884 | MI0022731 | — | chr17 | 40026332 | 40026409 | − | — |
| hsa-mir-6883 | MI0022730 | — | chr17 | 8144994 | 8145071 | − | — |
| hsa-mir-6882 | MI0022729 | 29 | chr15 | 74840642 | 74840707 | − | — |
| hsa-mir-6881 | MI0022728 | — | chr15 | 74411357 | 74411432 | − | — |
| hsa-mir-6880 | MI0022727 | 2 | chr12 | 124337181 | 124337242 | − | — |
| hsa-mir-6879 | MI0022726 | 162 | chr11 | 65018505 | 65018570 | + | — |
| hsa-mir-6878 | MI0022725 | 69 | chr1 | 150492345 | 150492410 | + | — |
| hsa-mir-6877 | MI0022724 | — | chr9 | 133051996 | 133052059 | + | — |
| hsa-mir-6876 | MI0022723 | 12 | chr8 | 25345402 | 25345474 | + | — |
| hsa-mir-6875 | MI0022722 | 49 | chr7 | 100868036 | 100868107 | + | — |
| hsa-mir-6874 | MI0022721 | 18 | chr7 | 5711840 | 5711910 | − | — |
| hsa-mir-6873 | MI0022720 | 72 | chr6 | 33287227 | 33287289 | − | — |
| hsa-mir-6872 | MI0022719 | — | chr3 | 50273236 | 50273297 | + | — |
| hsa-mir-6871 | MI0022718 | — | chr20 | 41169023 | 41169078 | + | — |
| hsa-mir-6870 | MI0022717 | 2 | chr20 | 10649636 | 10649695 | − | — |

TABLE 2-continued

| miRNA ID | Accession | RPM | Chromosome | Start | End | Strand | Confidence |
|---|---|---|---|---|---|---|---|
| hsa-mir-6869 | MI0022716 | — | chr20 | 1392900 | 1392961 | − | — |
| hsa-mir-6868 | MI0022715 | — | chr17 | 76098019 | 76098076 | − | — |
| hsa-mir-6867 | MI0022714 | 4 | chr17 | 40193597 | 40193663 | + | — |
| hsa-mir-6866 | MI0022713 | — | chr17 | 40161933 | 40162001 | + | — |
| hsa-mir-6865 | MI0022712 | — | chr17 | 4970086 | 4970150 | − | — |
| hsa-mir-6864 | MI0022711 | — | chr17 | 4969702 | 4969771 | − | — |
| hsa-mir-6863 | MI0022710 | — | chr16 | 56904264 | 56904353 | + | — |
| hsa-mir-6862-2 | MI0026415 | — | chr16 | 28724252 | 28724321 | + | — |
| hsa-mir-6862-1 | MI0022709 | — | chr16 | 28390982 | 28391051 | − | — |
| hsa-mir-6861 | MI0022708 | 6 | chr12 | 112163258 | 112163321 | − | — |
| hsa-mir-6860 | MI0022707 | — | chr11 | 67045643 | 67045708 | + | — |
| hsa-mir-6859-4 | MI0031521 | — | chr16 | 17052 | 17119 | − | — |
| hsa-mir-6859-3 | MI0026421 | — | chr15 | 101973524 | 101973591 | + | — |
| hsa-mir-6859-2 | MI0026420 | — | chr1 | 187891 | 187958 | − | — |
| hsa-mir-6859-1 | MI0022705 | — | chr1 | 17369 | 17436 | − | — |
| hsa-mir-6858 | MI0022704 | 19 | chrX | 154450320 | 154450386 | + | — |
| hsa-mir-6857 | MI0022703 | — | chrX | 53405673 | 53405765 | − | — |
| hsa-mir-6856 | MI0022702 | 47 | chr9 | 130626297 | 130626363 | + | — |
| hsa-mir-6855 | MI0022701 | — | chr9 | 129869605 | 129869671 | + | ✓ |
| hsa-mir-6854 | MI0022700 | — | chr9 | 98229149 | 98229217 | − | — |
| hsa-mir-6853 | MI0022699 | — | chr9 | 35732922 | 35732995 | + | — |
| hsa-mir-6852 | MI0022698 | — | chr9 | 35710676 | 35710741 | − | — |
| hsa-mir-6851 | MI0022697 | 2 | chr9 | 33467869 | 33467935 | − | — |
| hsa-mir-6850 | MI0022696 | — | chr8 | 144791931 | 144791991 | − | — |
| hsa-mir-6849 | MI0022695 | — | chr8 | 144400277 | 144400345 | − | — |
| hsa-mir-6848 | MI0022694 | — | chr8 | 144317246 | 144317315 | − | — |
| hsa-mir-6847 | MI0022693 | — | chr8 | 144079874 | 144079942 | + | — |
| hsa-mir-6846 | MI0022692 | 20 | chr8 | 144057321 | 144057380 | − | — |
| hsa-mir-6845 | MI0022691 | — | chr8 | 143837756 | 143837816 | − | — |
| hsa-mir-6844 | MI0022690 | — | chr8 | 124508515 | 124508576 | − | — |
| hsa-mir-6843 | MI0022689 | — | chr8 | 27610601 | 27610751 | − | — |
| hsa-mir-6842 | MI0022688 | 34 | chr8 | 27433370 | 27433434 | + | — |
| hsa-mir-6841 | MI0022687 | — | chr8 | 24953796 | 24953867 | − | — |
| hsa-mir-6840 | MI0022686 | — | chr7 | 100356651 | 100356721 | + | — |
| hsa-mir-6839 | MI0022685 | — | chr7 | 64679064 | 64679176 | + | — |
| hsa-mir-6838 | MI0022684 | — | chr7 | 44073378 | 44073433 | − | — |
| hsa-mir-6837 | MI0022683 | — | chr7 | 44051766 | 44051829 | + | — |
| hsa-mir-6836 | MI0022682 | 10 | chr7 | 2257515 | 2257577 | − | — |
| hsa-mir-6835 | MI0022680 | — | chr6 | 34240673 | 34240736 | + | — |

TABLE 2-continued

| miRNA ID | Accession | RPM | Chromosome | Start | End | Strand | Confidence |
|---|---|---|---|---|---|---|---|
| hsa-mir-6834 | MI0022679 | — | chr6 | 33290245 | 33290325 | + | — |
| hsa-mir-6833 | MI0022678 | 1 | chr6 | 32179816 | 32179876 | + | — |
| hsa-mir-6832 | MI0022677 | 12 | chr6 | 31633787 | 31633858 | + | — |
| hsa-mir-6831 | MI0022676 | — | chr5 | 140563671 | 140563751 | − | — |
| hsa-mir-6830 | MI0022675 | — | chr5 | 132217849 | 132217918 | − | — |
| hsa-mir-6829 | MI0022674 | — | chr3 | 195882329 | 195882395 | − | — |
| hsa-mir-6828 | MI0022673 | — | chr3 | 170423103 | 170423162 | + | — |
| hsa-mir-6827 | MI0022672 | — | chr3 | 134367804 | 134367862 | − | — |
| hsa-mir-6826 | MI0022671 | 3 | chr3 | 129272146 | 129272243 | + | — |
| hsa-mir-6825 | MI0022670 | — | chr3 | 127575266 | 127575331 | − | — |
| hsa-mir-6824 | MI0022669 | — | chr3 | 48633636 | 48633698 | − | — |
| hsa-mir-6823 | MI0022668 | — | chr3 | 48549961 | 48550021 | − | — |
| hsa-mir-6822 | MI0022667 | 3 | chr3 | 39138206 | 39138266 | + | — |
| hsa-mir-6821 | MI0022666 | 5 | chr22 | 49962866 | 49962939 | + | — |
| hsa-mir-6820 | MI0022665 | — | chr22 | 37967563 | 37967624 | + | ✓ |
| hsa-mir-6819 | MI0022664 | — | chr22 | 36286847 | 36286907 | − | — |
| hsa-mir-6818 | MI0022663 | 5 | chr22 | 30007049 | 30007113 | + | — |
| hsa-mir-6817 | MI0022662 | — | chr22 | 25455646 | 25455711 | + | — |
| hsa-mir-6816 | MI0022661 | — | chr22 | 20114686 | 20114751 | − | — |
| hsa-mir-6815 | MI0022660 | — | chr21 | 45478266 | 45478326 | + | — |
| hsa-mir-6814 | MI0022659 | — | chr21 | 41746772 | 41746841 | − | — |
| hsa-mir-6813 | MI0022658 | — | chr20 | 64076955 | 64077010 | − | — |
| hsa-mir-6812 | MI0022657 | 90 | chr20 | 45425510 | 45425573 | + | — |
| hsa-mir-6811 | MI0022656 | — | chr2 | 237510931 | 237510988 | + | — |
| hsa-mir-6810 | MI0022655 | — | chr2 | 218341911 | 218341980 | + | — |
| hsa-mir-6809 | MI0022654 | 2 | chr2 | 217900513 | 217900628 | − | — |
| hsa-mir-6808 | MI0022653 | — | chr1 | 1339650 | 1339708 | − | — |
| hsa-mir-6807 | MI0022652 | 8 | chr19 | 58550285 | 58550376 | + | — |
| hsa-mir-6806 | MI0022651 | — | chr19 | 58334688 | 58334751 | + | — |
| hsa-mir-6805 | MI0022650 | 28 | chr19 | 55388181 | 55388242 | + | — |
| hsa-mir-6804 | MI0022649 | — | chr19 | 55230885 | 55230952 | − | — |
| hsa-mir-6803 | MI0022648 | 9 | chr19 | 55245186 | 55245250 | − | — |
| hsa-mir-6802 | MI0022647 | — | chr19 | 55239912 | 55239976 | − | — |
| hsa-mir-6801 | MI0022646 | — | chr19 | 52222020 | 52222098 | + | — |
| hsa-mir-6800 | MI0022645 | 1 | chr19 | 49832018 | 49832099 | + | — |
| hsa-mir-6799 | MI0022644 | — | chr19 | 49791866 | 49791934 | + | — |
| hsa-mir-6798 | MI0022643 | — | chr19 | 49009906 | 49009972 | + | — |
| hsa-mir-6797 | MI0022642 | 6 | chr19 | 41869627 | 41869698 | + | — |
| hsa-mir-6796 | MI0022641 | 2 | chr19 | 40369846 | 40369907 | + | — |

TABLE 2-continued

| miRNA ID | Accession | RPM | Chromosome | Start | End | Strand | Confidence |
|---|---|---|---|---|---|---|---|
| hsa-mir-6795 | MI0022640 | 3 | chr19 | 15179283 | 15179350 | – | – |
| hsa-mir-6794 | MI0022639 | 26 | chr19 | 12852260 | 12852327 | + | – |
| hsa-mir-6793 | MI0022638 | – | chr19 | 10828973 | 10829035 | + | – |
| hsa-mir-6792 | MI0022637 | 7 | chr19 | 7617439 | 7617505 | + | – |
| hsa-mir-6791 | MI0022636 | 5 | chr19 | 6736712 | 6736778 | – | – |
| hsa-mir-6790 | MI0022635 | – | chr19 | 6392921 | 6392983 | – | – |
| hsa-mir-6789 | MI0022634 | 51 | chr19 | 2235829 | 2235926 | – | – |
| hsa-mir-6788 | MI0022633 | 65 | chr18 | 10759584 | 10759649 | – | – |
| hsa-mir-6787 | MI0022632 | – | chr17 | 82236668 | 82236728 | + | – |
| hsa-mir-6786 | MI0022631 | 13 | chr17 | 81693757 | 81693869 | + | – |
| hsa-mir-6785 | MI0022630 | 2 | chr17 | 75498548 | 75498628 | + | – |
| hsa-mir-6784 | MI0022629 | – | chr17 | 45114367 | 45114433 | – | – |
| hsa-mir-6783 | MI0022628 | – | chr17 | 44934618 | 44934681 | – | – |
| hsa-mir-6782 | MI0022627 | – | chr17 | 44207771 | 44207839 | – | – |
| hsa-mir-6781 | MI0022626 | – | chr17 | 42823880 | 42823943 | – | – |
| hsa-mir-6780b | MI0022681 | – | chr6 | 43434542 | 43434620 | + | – |
| hsa-mir-6780a | MI0022625 | – | chr17 | 42708084 | 42708151 | – | – |
| hsa-mir-6779 | MI0022624 | 6 | chr17 | 38914979 | 38915042 | + | – |
| hsa-mir-6778 | MI0022623 | 5 | chr17 | 18340814 | 18340886 | – | – |
| hsa-mir-6777 | MI0022622 | – | chr17 | 17813480 | 17813545 | – | – |
| hsa-mir-6776 | MI0022621 | – | chr17 | 2692861 | 2692919 | – | – |
| hsa-mir-6775 | MI0022620 | – | chr16 | 87834592 | 87834660 | – | – |
| hsa-mir-6774 | MI0022619 | – | chr16 | 85918347 | 85918416 | + | – |
| hsa-mir-6773 | MI0022618 | – | chr16 | 68233426 | 68233499 | – | – |
| hsa-mir-6772 | MI0022617 | – | chr16 | 57772289 | 57772352 | – | – |
| hsa-mir-6771 | MI0022616 | 5 | chr16 | 50292616 | 50292675 | + | – |
| hsa-mir-6770-3 | MI0026419 | – | chr16 | 18379351 | 18379410 | – | ✓ |
| hsa-mir-6770-2 | MI0026418 | – | chr16 | 16329305 | 16329364 | + | ✓ |
| hsa-mir-6770-1 | MI0022615 | – | chr16 | 14930820 | 14930879 | + | ✓ |
| hsa-mir-6769b | MI0022706 | – | chr1 | 206474803 | 206474864 | + | – |
| hsa-mir-6769a | MI0022614 | – | chr16 | 4671318 | 4671390 | + | – |
| hsa-mir-6768 | MI0022613 | – | chr16 | 2463967 | 2464038 | + | – |
| hsa-mir-6767 | MI0022612 | – | chr16 | 2445392 | 2445457 | + | – |
| hsa-mir-6766 | MI0022611 | – | chr15 | 89326739 | 89326810 | – | – |
| hsa-mir-6765 | MI0022610 | 9 | chr14 | 105150778 | 105150864 | – | – |
| hsa-mir-6764 | MI0022609 | 2 | chr14 | 100277357 | 100277417 | + | – |
| hsa-mir-6763 | MI0022608 | 5 | chr12 | 132581997 | 132582061 | + | – |
| hsa-mir-6762 | MI0022607 | – | chr12 | 113291523 | 113291608 | + | – |
| hsa-mir-6761 | MI0022606 | 1 | chr12 | 111799834 | 111799905 | + | – |

TABLE 2-continued

| miRNA ID | Accession | RPM | Chromosome | Start | End | Strand | Confidence |
|---|---|---|---|---|---|---|---|
| hsa-mir-6760 | MI0022605 | — | chr12 | 111304142 | 111304209 | + | — |
| hsa-mir-676 | MI0016436 | — | chrX | 70022857 | 70022923 | + | ✓ |
| hsa-mir-6759 | MI0022604 | — | chr12 | 57748618 | 57748682 | − | — |
| hsa-mir-6758 | MI0022603 | — | chr12 | 57512688 | 57512750 | + | ✓ |
| hsa-mir-6757 | MI0022602 | 3 | chr12 | 53056944 | 53057012 | + | — |
| hsa-mir-6756 | MI0022601 | 21 | chr11 | 119312950 | 119313012 | − | — |
| hsa-mir-6755 | MI0022600 | — | chr11 | 86278333 | 86278398 | + | — |
| hsa-mir-6754 | MI0022599 | — | chr11 | 71473503 | 71473568 | + | — |
| hsa-mir-6753 | MI0022598 | 13 | chr11 | 68044794 | 68044957 | + | — |
| hsa-mir-6752 | MI0022597 | 17 | chr11 | 67490245 | 67490315 | + | — |
| hsa-mir-6751 | MI0022596 | 41 | chr11 | 65129916 | 65129978 | − | — |
| hsa-mir-6750 | MI0022595 | 2 | chr11 | 64898363 | 64898437 | − | — |
| hsa-mir-675 | MI0005416 | 20 | chr11 | 1996759 | 1996831 | − | ✓ |
| hsa-mir-6749 | MI0022594 | 7 | chr11 | 64902387 | 64902455 | − | — |
| hsa-mir-6748 | MI0022593 | — | chr11 | 62789815 | 62789885 | + | — |
| hsa-mir-6747 | MI0022592 | 5 | chr11 | 62567011 | 62567071 | − | — |
| hsa-mir-6746 | MI0022591 | 2 | chr11 | 61878216 | 61878278 | − | — |
| hsa-mir-6745 | MI0022590 | — | chr11 | 47179611 | 47179737 | − | — |
| hsa-mir-6744 | MI0022589 | — | chr11 | 1256605 | 1256670 | + | — |
| hsa-mir-6743 | MI0022588 | — | chr11 | 209336 | 209406 | + | — |
| hsa-mir-6742 | MI0022587 | — | chr1 | 228397048 | 228397109 | − | — |
| hsa-mir-6741 | MI0022586 | — | chr1 | 225922080 | 225922142 | − | — |
| hsa-mir-6740 | MI0022585 | 4 | chr1 | 202003124 | 202003236 | + | — |
| hsa-mir-6739 | MI0022584 | — | chr1 | 201863373 | 201863447 | + | — |
| hsa-mir-6738 | MI0022583 | — | chr1 | 155951273 | 155951336 | − | — |
| hsa-mir-6737 | MI0022582 | — | chr1 | 153962351 | 153962420 | − | — |
| hsa-mir-6736 | MI0022581 | 6 | chr1 | 145850587 | 145850645 | − | — |
| hsa-mir-6735 | MI0022580 | 1 | chr1 | 43448539 | 43448611 | + | — |
| hsa-mir-6734 | MI0022579 | 1 | chr1 | 43364648 | 43364715 | − | — |
| hsa-mir-6733 | MI0022578 | — | chr1 | 43171652 | 43171712 | − | — |
| hsa-mir-6732 | MI0022577 | 2 | chr1 | 37480230 | 37480289 | + | — |
| hsa-mir-6731 | MI0022576 | 2 | chr1 | 24919345 | 24919416 | − | — |
| hsa-mir-6730 | MI0022575 | 51 | chr1 | 12578957 | 12579023 | − | — |
| hsa-mir-6729 | MI0022574 | — | chr1 | 12029158 | 12029222 | + | — |
| hsa-mir-6728 | MI0022573 | 84 | chr1 | 8866502 | 8866590 | − | — |
| hsa-mir-6727 | MI0022572 | 5 | chr1 | 1312502 | 1312566 | − | — |
| hsa-mir-6726 | MI0022571 | — | chr1 | 1296110 | 1296170 | − | — |
| hsa-mir-6724-4 | MI0031518 | 1 | chr21 | 8432530 | 8432621 | + | — |
| hsa-mir-6724-3 | MI0031517 | 1 | chr21 | 8388362 | 8388453 | + | — |

TABLE 2-continued

| miRNA ID | Accession | RPM | Chromosome | Start | End | Strand | Confidence |
|---|---|---|---|---|---|---|---|
| hsa-mir-6724-2 | MI0031516 | 1 | chr21 | 8249505 | 8249596 | + | — |
| hsa-mir-6724-1 | MI0022559 | 1 | chr21 | 8205315 | 8205406 | + | — |
| hsa-mir-6722 | MI0022557 | — | chr9 | 136746893 | 136746970 | — | — |
| hsa-mir-6721 | MI0022556 | 2 | chr6 | 32170030 | 32170116 | — | — |
| hsa-mir-6720 | MI0022555 | 1 | chr6 | 1390314 | 1390411 | — | ✓ |
| hsa-mir-6719 | MI0022554 | 33 | chr19 | 39829716 | 39829802 | — | — |
| hsa-mir-6718 | MI0022553 | — | chr18 | 3885353 | 3885432 | + | — |
| hsa-mir-6717 | MI0022551 | — | chr14 | 21023314 | 21023386 | — | — |
| hsa-mir-6716 | MI0022550 | 13 | chr11 | 118644000 | 118644079 | + | — |
| hsa-mir-6715b | MI0022549 | — | chr10 | 112299612 | 112299688 | — | — |
| hsa-mir-6715a | MI0022548 | 24 | chr10 | 112299612 | 112299690 | + | — |
| hsa-mir-671 | MI0003760 | 77 | chr7 | 151238421 | 151238538 | + | ✓ |
| hsa-mir-670 | MI0003933 | — | chr11 | 43559656 | 43559753 | + | — |
| hsa-mir-668 | MI0003761 | 7 | chr14 | 101055258 | 101055323 | + | — |
| hsa-mir-665 | MI0005563 | 14 | chr14 | 100875033 | 100875104 | + | — |
| hsa-mir-664b | MI0019134 | 2 | chrX | 154768596 | 154768656 | + | ✓ |
| hsa-mir-664a | MI0006442 | 64 | chr1 | 220200538 | 220200619 | — | ✓ |
| hsa-mir-663b | MI0006336 | 9 | chr2 | 132256966 | 132257080 | — | — |
| hsa-mir-663a | MI0003672 | 10 | chr20 | 26208186 | 26208278 | — | — |
| hsa-mir-662 | MI0003670 | — | chr16 | 770183 | 770277 | + | — |
| hsa-mir-661 | MI0003669 | 130 | chr8 | 143945191 | 143945279 | — | — |
| hsa-mir-660 | MI0003684 | 510 | chrX | 50013241 | 50013337 | + | ✓ |
| hsa-mir-659 | MI0003683 | 1 | chr22 | 37847678 | 37847774 | — | — |
| hsa-mir-658 | MI0003682 | 1 | chr22 | 37844272 | 37844371 | — | — |
| hsa-mir-657 | MI0003681 | 7 | chr17 | 81125276 | 81125373 | — | — |
| hsa-mir-656 | MI0003678 | — | chr14 | 101066724 | 101066801 | + | — |
| hsa-mir-655 | MI0003677 | 6 | chr14 | 101049550 | 101049646 | + | — |
| hsa-mir-654 | MI0003676 | 5 | chr14 | 101040219 | 101040299 | + | ✓ |
| hsa-mir-653 | MI0003674 | — | chr7 | 93482760 | 93482855 | — | ✓ |
| hsa-mir-6529 | MI0039501 | — | chr3 | 120084564 | 120084648 | — | — |
| hsa-mir-652 | MI0003667 | 189 | chrX | 110055329 | 110055426 | + | ✓ |
| hsa-mir-6516 | MI0025513 | 2 | chr17 | 77089417 | 77089497 | + | — |
| hsa-mir-6515 | MI0022227 | 4 | chr19 | 12940484 | 12940540 | + | — |
| hsa-mir-6514 | MI0022226 | — | chr11 | 62792702 | 62792771 | — | — |
| hsa-mir-6513 | MI0022225 | 2 | chr2 | 218280125 | 218280188 | — | — |
| hsa-mir-6512 | MI0022224 | 2 | chr2 | 177313806 | 177313882 | — | — |
| hsa-mir-6511b-2 | MI0023431 | 6 | chr16 | 15134075 | 15134145 | — | — |
| hsa-mir-6511b-1 | MI0022552 | 5 | chr16 | 2106669 | 2106753 | — | — |
| hsa-mir-6511a-4 | MI0023566 | 3 | chr16 | 18344013 | 18344079 | — | ✓ |

TABLE 2-continued

| miRNA ID | Accession | RPM | Chromosome | Start | End | Strand | Confidence |
|---|---|---|---|---|---|---|---|
| hsa-mir-6511a-3 | MI0023565 | 3 | chr16 | 16368876 | 16368942 | + | ✓ |
| hsa-mir-6511a-2 | MI0023564 | 3 | chr16 | 16324588 | 16324654 | + | ✓ |
| hsa-mir-6511a-1 | MI0022223 | 3 | chr16 | 14925937 | 14926003 | + | ✓ |
| hsa-mir-6510 | MI0022222 | 5 | chr17 | 41517164 | 41517217 | − | — |
| hsa-mir-651 | MI0003666 | 7 | chrX | 8126965 | 8127061 | + | ✓ |
| hsa-mir-6509 | MI0022221 | — | chr7 | 135206994 | 135207078 | − | — |
| hsa-mir-6508 | MI0022220 | — | chr21 | 39447010 | 39447069 | + | — |
| hsa-mir-6507 | MI0022219 | 2 | chr10 | 98924499 | 98924568 | − | — |
| hsa-mir-6506 | MI0022218 | — | chr16 | 15611030 | 15611095 | − | — |
| hsa-mir-6505 | MI0022217 | 1 | chr12 | 48132797 | 48132867 | + | — |
| hsa-mir-6504 | MI0022216 | — | chr16 | 81611348 | 81611408 | + | — |
| hsa-mir-6503 | MI0022215 | — | chr11 | 60209071 | 60209156 | − | — |
| hsa-mir-6502 | MI0022214 | — | chr12 | 66251082 | 66251157 | + | — |
| hsa-mir-6501 | MI0022213 | — | chr21 | 33550662 | 33550728 | + | — |
| hsa-mir-6500 | MI0022211 | 58 | chr1 | 51060018 | 51060103 | + | — |
| hsa-mir-650 | MI0003665 | — | chr22 | 22822776 | 22822871 | + | — |
| hsa-mir-6499 | MI0022209 | 7 | chr5 | 151522087 | 151522148 | − | — |
| hsa-mir-649 | MI0003664 | — | chr22 | 21034176 | 21034272 | − | — |
| hsa-mir-648 | MI0003663 | 31 | chr22 | 17980868 | 17980961 | − | — |
| hsa-mir-647 | MI0003662 | 42 | chr20 | 63942631 | 63942726 | − | — |
| hsa-mir-646 | MI0003661 | — | chr20 | 60308474 | 60308567 | + | — |
| hsa-mir-645 | MI0003660 | 21 | chr20 | 50585786 | 50585879 | + | — |
| hsa-mir-644a | MI0003659 | — | chr20 | 34466325 | 34466418 | + | — |
| hsa-mir-643 | MI0003658 | 216 | chr19 | 52281797 | 52281893 | + | ✓ |
| hsa-mir-642b | MI0016685 | — | chr19 | 45674932 | 45675008 | − | ✓ |
| hsa-mir-642a | MI0003657 | — | chr19 | 45674928 | 45675024 | + | ✓ |
| hsa-mir-641 | MI0003656 | 4 | chr19 | 40282543 | 40282641 | − | — |
| hsa-mir-640 | MI0003655 | 36 | chr19 | 19435063 | 19435158 | + | — |
| hsa-mir-639 | MI0003654 | 78 | chr19 | 14529543 | 14529640 | + | — |
| hsa-mir-638 | MI0003653 | 9 | chr19 | 10718404 | 10718503 | + | — |
| hsa-mir-637 | MI0003652 | 37 | chr19 | 3961414 | 3961512 | − | — |
| hsa-mir-636 | MI0003651 | 37 | chr17 | 76736450 | 76736548 | − | — |
| hsa-mir-635 | MI0003650 | — | chr17 | 68424451 | 68424548 | − | — |
| hsa-mir-634 | MI0003649 | — | chr17 | 66787072 | 66787168 | + | — |
| hsa-mir-633 | MI0003648 | — | chr17 | 62944215 | 62944312 | + | — |
| hsa-mir-632 | MI0003647 | 10 | chr17 | 32350109 | 32350202 | + | — |
| hsa-mir-631 | MI0003645 | — | chr15 | 75353611 | 75353685 | − | — |
| hsa-mir-630 | MI0003644 | 3442 | chr15 | 72587217 | 72587313 | + | — |
| hsa-mir-629 | MI0003643 | 99 | chr15 | 70079372 | 70079468 | − | ✓ |

TABLE 2-continued

| miRNA ID | Accession | RPM | Chromosome | Start | End | Strand | Confidence |
|---|---|---|---|---|---|---|---|
| hsa-mir-628 | MI0003642 | 4 | chr15 | 55372940 | 55373034 | − | − |
| hsa-mir-627 | MI0003641 | 3 | chr15 | 42199570 | 42199666 | − | ✓ |
| hsa-mir-626 | MI0003640 | − | chr15 | 41691585 | 41691678 | + | − |
| hsa-mir-625 | MI0003639 | 24 | chr14 | 65471102 | 65471186 | + | ✓ |
| hsa-mir-624 | MI0003638 | − | chr14 | 31014646 | 31014742 | − | − |
| hsa-mir-623 | MI0003637 | − | chr13 | 99356131 | 99356228 | + | − |
| hsa-mir-622 | MI0003636 | 5 | chr13 | 90231182 | 90231277 | + | − |
| hsa-mir-621 | MI0003635 | 11 | chr13 | 40810766 | 40810861 | + | − |
| hsa-mir-620 | MI0003634 | 20 | chr12 | 116148560 | 116148654 | − | − |
| hsa-mir-619 | MI0003633 | 201 | chr12 | 108836908 | 108837006 | − | − |
| hsa-mir-618 | MI0003632 | 13 | chr12 | 80935736 | 80935833 | − | − |
| hsa-mir-617 | MI0003631 | 38 | chr12 | 80832533 | 80832629 | − | − |
| hsa-mir-6165 | MI0021472 | 39 | chr17 | 49510817 | 49510900 | + | − |
| hsa-mir-616 | MI0003629 | 1 | chr12 | 57519163 | 57519259 | − | ✓ |
| hsa-mir-615 | MI0003628 | 117 | chr12 | 54033950 | 54034045 | + | ✓ |
| hsa-mir-614 | MI0003627 | − | chr12 | 12915829 | 12915918 | + | − |
| hsa-mir-6134 | MI0021279 | 38 | chrX | 28495555 | 28495663 | − | − |
| hsa-mir-6133 | MI0021278 | 1 | chr7 | 133290881 | 133290988 | + | − |
| hsa-mir-6132 | MI0021277 | − | chr7 | 117020211 | 117020319 | + | − |
| hsa-mir-6131 | MI0021276 | − | chr5 | 10478037 | 10478145 | + | − |
| hsa-mir-6130 | MI0021275 | 335 | chr21 | 23079284 | 23079392 | + | − |
| hsa-mir-613 | MI0003626 | 24 | chr12 | 12764649 | 12764743 | + | − |
| hsa-mir-6129 | MI0021274 | 8 | chr17 | 49288346 | 49288454 | − | − |
| hsa-mir-6128 | MI0021272 | 20 | chr11 | 56743873 | 56743981 | + | − |
| hsa-mir-6127 | MI0021271 | 87 | chr1 | 22633258 | 22633366 | − | − |
| hsa-mir-6126 | MI0021260 | 68 | chr16 | 3485381 | 3485469 | − | − |
| hsa-mir-6125 | MI0021259 | 4 | chr12 | 62260359 | 62260454 | + | − |
| hsa-mir-6124 | MI0021258 | 214 | chr11 | 12163683 | 12163767 | + | − |
| hsa-mir-612 | MI0003625 | 45 | chr11 | 65444458 | 65444557 | + | − |
| hsa-mir-611 | MI0003624 | 4 | chr11 | 61792495 | 61792561 | − | − |
| hsa-mir-610 | MI0003623 | 13 | chr11 | 28056815 | 28056910 | + | − |
| hsa-mir-6090 | MI0020367 | − | chr11 | 128522390 | 128522449 | + | − |
| hsa-mir-609 | MI0003622 | − | chr10 | 104218789 | 104218883 | − | − |
| hsa-mir-6089-2 | MI0023563 | 2 | chrY | 2609191 | 2609254 | + | − |
| hsa-mir-6089-1 | MI0020366 | 2 | chrX | 2609191 | 2609254 | + | − |
| hsa-mir-6088 | MI0020365 | 24 | chr19 | 45436654 | 45436704 | + | − |
| hsa-mir-6086 | MI0020363 | 83 | chrX | 13590292 | 13590346 | + | − |
| hsa-mir-6085 | MI0020362 | − | chr15 | 62343029 | 62343138 | + | − |
| hsa-mir-6084 | MI0020361 | − | chr1 | 20633679 | 20633788 | + | − |

TABLE 2-continued

| miRNA ID | Accession | RPM | Chromosome | Start | End | Strand | Confidence |
|---|---|---|---|---|---|---|---|
| hsa-mir-6083 | MI0020360 | 6 | chr3 | 124374332 | 124374437 | + | — |
| hsa-mir-6082 | MI0020359 | 22 | chr4 | 171186184 | 171186292 | + | — |
| hsa-mir-6081 | MI0020358 | — | chr9 | 95065350 | 95065446 | + | — |
| hsa-mir-6080 | MI0020357 | — | chr17 | 64780759 | 64780824 | + | — |
| hsa-mir-608 | MI0003621 | — | chr10 | 100974985 | 100975084 | + | — |
| hsa-mir-6079 | MI0020356 | — | chr1 | 43838622 | 43838683 | + | — |
| hsa-mir-6078 | MI0020355 | — | chr10 | 3991160 | 3991259 | + | — |
| hsa-mir-6077 | MI0020354 | — | chr1 | 148388282 | 148388363 | + | — |
| hsa-mir-6076 | MI0020353 | 21 | chr14 | 49966399 | 49966511 | + | — |
| hsa-mir-6075 | MI0020352 | 24 | chr5 | 1510762 | 1510856 | − | — |
| hsa-mir-6074 | MI0020351 | 49 | chr12 | 66023620 | 66023726 | − | — |
| hsa-mir-6073 | MI0020350 | 4 | chr11 | 15969533 | 15969621 | − | — |
| hsa-mir-6072 | MI0020349 | — | chr10 | 2076019 | 2076089 | − | — |
| hsa-mir-6071 | MI0020348 | — | chr2 | 85783600 | 85783677 | − | — |
| hsa-mir-6070 | MI0020347 | — | chr21 | 43609887 | 43609989 | − | — |
| hsa-mir-607 | MI0003620 | — | chr10 | 96828669 | 96828764 | − | — |
| hsa-mir-6069 | MI0020346 | 244 | chr22 | 35336721 | 35336799 | − | — |
| hsa-mir-6068 | MI0020345 | — | chr1 | 63326925 | 63326984 | − | — |
| hsa-mir-606 | MI0003619 | — | chr10 | 75552458 | 75552553 | + | — |
| hsa-mir-605 | MI0003618 | 20 | chr10 | 51299573 | 51299655 | + | ✓ |
| hsa-mir-604 | MI0003617 | — | chr10 | 29545004 | 29545097 | − | — |
| hsa-mir-603 | MI0003616 | 1 | chr10 | 24275685 | 24275781 | + | — |
| hsa-mir-602 | MI0003615 | 4 | chr9 | 137838419 | 137838516 | + | — |
| hsa-mir-601 | MI0003614 | — | chr9 | 123402525 | 123402603 | − | — |
| hsa-mir-600 | MI0003613 | — | chr9 | 123111546 | 123111643 | − | — |
| hsa-mir-599 | MI0003611 | 3 | chr8 | 99536636 | 99536730 | − | — |
| hsa-mir-598 | MI0003610 | 138 | chr8 | 11035206 | 11035302 | − | ✓ |
| hsa-mir-597 | MI0003609 | — | chr8 | 9741672 | 9741768 | + | ✓ |
| hsa-mir-596 | MI0003608 | — | chr8 | 1817231 | 1817307 | + | — |
| hsa-mir-595 | MI0003607 | — | chr7 | 158532718 | 158532813 | − | — |
| hsa-mir-593 | MI0003605 | — | chr7 | 128081861 | 128081960 | + | — |
| hsa-mir-592 | MI0003604 | — | chr7 | 127058088 | 127058184 | − | — |
| hsa-mir-591 | MI0003603 | — | chr7 | 96219662 | 96219756 | − | — |
| hsa-mir-590 | MI0003602 | 270 | chr7 | 74191198 | 74191294 | + | ✓ |
| hsa-mir-589 | MI0003599 | 8 | chr7 | 5495819 | 5495917 | − | ✓ |
| hsa-mir-588 | MI0003597 | 4 | chr6 | 126484631 | 126484713 | + | — |
| hsa-mir-587 | MI0003595 | — | chr6 | 106784125 | 106784220 | + | — |
| hsa-mir-586 | MI0003594 | — | chr6 | 45197674 | 45197770 | − | — |
| hsa-mir-585 | MI0003592 | 5 | chr5 | 169263601 | 169263694 | − | ✓ |

TABLE 2-continued

| miRNA ID | Accession | RPM | Chromosome | Start | End | Strand | Confidence |
|---|---|---|---|---|---|---|---|
| hsa-mir-584 | MI0003591 | 97 | chr5 | 149062313 | 149062409 | − | ✓ |
| hsa-mir-583 | MI0003590 | — | chr5 | 96079138 | 96079212 | + | — |
| hsa-mir-582 | MI0003589 | 151 | chr5 | 59703606 | 59703703 | − | ✓ |
| hsa-mir-581 | MI0003588 | 3 | chr5 | 53951504 | 53951599 | − | — |
| hsa-mir-580 | MI0003587 | — | chr5 | 36147892 | 36147988 | − | — |
| hsa-mir-579 | MI0003586 | 4 | chr5 | 32394378 | 32394475 | − | ✓ |
| hsa-mir-5787 | MI0019797 | — | chr3 | 50227436 | 50227490 | + | — |
| hsa-mir-578 | MI0003585 | — | chr4 | 165386242 | 165386337 | + | — |
| hsa-mir-577 | MI0003584 | 13 | chr4 | 114656759 | 114656854 | + | ✓ |
| hsa-mir-576 | MI0003583 | 15 | chr4 | 109488698 | 109488795 | + | ✓ |
| hsa-mir-575 | MI0003582 | 81 | chr4 | 82753337 | 82753430 | − | — |
| hsa-mir-574 | MI0003581 | 780 | chr4 | 38868032 | 38868127 | + | ✓ |
| hsa-mir-5739 | MI0019412 | 50 | chr22 | 28459869 | 28459948 | + | — |
| hsa-mir-573 | MI0003580 | — | chr4 | 24520192 | 24520290 | − | — |
| hsa-mir-572 | MI0003579 | 6 | chr4 | 11368827 | 11368921 | + | — |
| hsa-mir-571 | MI0003578 | — | chr4 | 350157 | 350252 | + | — |
| hsa-mir-5708 | MI0019316 | 55 | chr8 | 80241389 | 80241473 | + | — |
| hsa-mir-5707 | MI0019315 | — | chr7 | 158591616 | 158591696 | + | — |
| hsa-mir-5706 | MI0019314 | — | chr5 | 119154637 | 119154716 | + | — |
| hsa-mir-5705 | MI0019313 | — | chr4 | 87300495 | 87300583 | − | — |
| hsa-mir-5704 | MI0019312 | — | chr3 | 131985855 | 131985931 | − | — |
| hsa-mir-5703 | MI0019310 | 6 | chr2 | 227472132 | 227472187 | + | — |
| hsa-mir-5702 | MI0019309 | — | chr2 | 226658710 | 226658793 | − | — |
| hsa-mir-5701-3 | MI0031522 | — | chr15 | 21951242 | 21951323 | + | — |
| hsa-mir-5701-2 | MI0019593 | — | chr15 | 21513959 | 21514040 | + | — |
| hsa-mir-5701-1 | MI0019308 | — | chr15 | 20940252 | 20940333 | + | — |
| hsa-mir-5700 | MI0019307 | — | chr12 | 94561789 | 94561859 | + | — |
| hsa-mir-570 | MI0003577 | 4 | chr3 | 195699401 | 195699497 | + | — |
| hsa-mir-5699 | MI0019306 | 6 | chr10 | 641689 | 641778 | − | — |
| hsa-mir-5698 | MI0019305 | — | chr1 | 154104521 | 154104592 | − | — |
| hsa-mir-5697 | MI0019304 | — | chr1 | 9967381 | 9967458 | + | — |
| hsa-mir-5696 | MI0019303 | — | chr2 | 101309450 | 101309534 | + | — |
| hsa-mir-5695 | MI0019302 | 1 | chr19 | 12920320 | 12920404 | + | — |
| hsa-mir-5694 | MI0019301 | 2 | chr14 | 67441855 | 67441930 | − | — |
| hsa-mir-5693 | MI0019300 | 4 | chr13 | 51348567 | 51348639 | − | — |
| hsa-mir-5692c-2 | MI0019289 | 3 | chr7 | 97964405 | 97964481 | − | — |
| hsa-mir-5692c-1 | MI0019288 | — | chr5 | 135802985 | 135803075 | − | — |
| hsa-mir-5692b | MI0019311 | — | chr21 | 42950928 | 42951014 | − | — |
| hsa-mir-5692a-2 | MI0019298 | — | chr8 | 12719132 | 12719190 | + | — |

TABLE 2-continued

| miRNA ID | Accession | RPM | Chromosome | Start | End | Strand | Confidence |
|---|---|---|---|---|---|---|---|
| hsa-mir-5692a-1 | MI0019297 | — | chr7 | 97963658 | 97963726 | + | — |
| hsa-mir-5691 | MI0019296 | — | chr11 | 9090312 | 9090379 | − | — |
| hsa-mir-5690 | MI0019295 | — | chr6 | 35664717 | 35664789 | − | — |
| hsa-mir-569 | MI0003576 | — | chr3 | 171106664 | 171106759 | − | — |
| hsa-mir-5689 | MI0019294 | 9 | chr6 | 10439717 | 10439794 | + | — |
| hsa-mir-5688 | MI0019292 | — | chr3 | 85385710 | 85385792 | + | — |
| hsa-mir-5687 | MI0019291 | — | chr5 | 55508850 | 55508926 | − | — |
| hsa-mir-5685 | MI0019287 | 21 | chr6 | 53276993 | 53277071 | + | — |
| hsa-mir-5684 | MI0019285 | 46 | chr19 | 12787128 | 12787192 | + | — |
| hsa-mir-5683 | MI0019284 | — | chr6 | 6169334 | 6169409 | + | — |
| hsa-mir-5682 | MI0019282 | — | chr3 | 121049640 | 121049715 | + | ✓ |
| hsa-mir-5681b | MI0019293 | — | chr8 | 74548550 | 74548609 | − | — |
| hsa-mir-5681a | MI0019281 | — | chr8 | 74548543 | 74548617 | + | — |
| hsa-mir-5680 | MI0019280 | — | chr8 | 102125432 | 102125515 | + | — |
| hsa-mir-568 | MI0003574 | — | chr3 | 114316475 | 114316569 | − | — |
| hsa-mir-567 | MI0003573 | 70 | chr3 | 112112801 | 112112898 | + | — |
| hsa-mir-564 | MI0003570 | — | chr3 | 44861888 | 44861981 | + | — |
| hsa-mir-563 | MI0003569 | — | chr3 | 15873771 | 15873849 | + | — |
| hsa-mir-562 | MI0003568 | — | chr2 | 232172653 | 232172747 | + | — |
| hsa-mir-561 | MI0003567 | 32 | chr2 | 188297492 | 188297588 | + | ✓ |
| hsa-mir-5591 | MI0019151 | — | chr4 | 39411910 | 39411974 | + | — |
| hsa-mir-5590 | MI0019150 | — | chr2 | 134857820 | 134857873 | + | — |
| hsa-mir-559 | MI0003565 | 9 | chr2 | 47377675 | 47377770 | + | — |
| hsa-mir-5589 | MI0019148 | — | chr19 | 10038354 | 10038413 | + | — |
| hsa-mir-5588 | MI0019147 | 97 | chr3 | 185253210 | 185253272 | − | — |
| hsa-mir-5587 | MI0019144 | 3 | chr16 | 535316 | 535368 | + | — |
| hsa-mir-5586 | MI0019143 | — | chr14 | 59646962 | 59647020 | − | — |
| hsa-mir-5585 | MI0019142 | 320 | chr1 | 32086949 | 32087007 | + | — |
| hsa-mir-5584 | MI0019141 | — | chr1 | 44545493 | 44545552 | + | — |
| hsa-mir-5583-2 | MI0019140 | — | chr18 | 39676719 | 39676777 | − | ✓ |
| hsa-mir-5583-1 | MI0019139 | — | chr18 | 39676721 | 39676779 | + | ✓ |
| hsa-mir-5582 | MI0019138 | — | chr11 | 46753125 | 46753192 | − | — |
| hsa-mir-5581 | MI0019136 | — | chr1 | 37500935 | 37500994 | − | — |
| hsa-mir-5580 | MI0019135 | — | chr14 | 53948427 | 53948484 | − | — |
| hsa-mir-558 | MI0003564 | 134 | chr2 | 32532153 | 32532246 | + | — |
| hsa-mir-5579 | MI0019133 | — | chr11 | 79422169 | 79422226 | − | — |
| hsa-mir-5572 | MI0019117 | 94 | chr15 | 80581103 | 80581239 | + | — |
| hsa-mir-5571 | MI0019115 | 22 | chr22 | 22886267 | 22886379 | + | — |
| hsa-mir-557 | MI0003563 | — | chr1 | 168375524 | 168375621 | + | — |

TABLE 2-continued

| miRNA ID | Accession | RPM | Chromosome | Start | End | Strand | Confidence |
|----------|-----------|-----|------------|-------|-----|--------|------------|
| hsa-mir-556 | MI0003562 | 3 | chr1 | 162342546 | 162342640 | + | ✓ |
| hsa-mir-555 | MI0003561 | — | chr1 | 155346350 | 155346445 | − | — |
| hsa-mir-554 | MI0003559 | — | chr1 | 151545796 | 151545891 | + | — |
| hsa-mir-553 | MI0003558 | — | chr1 | 100281241 | 100281308 | + | — |
| hsa-mir-552 | MI0003557 | — | chr1 | 34669599 | 34669694 | − | ✓ |
| hsa-mir-551b | MI0003575 | 70 | chr3 | 168551854 | 168551949 | + | ✓ |
| hsa-mir-551a | MI0003556 | 7 | chr1 | 3560695 | 3560790 | − | — |
| hsa-mir-550b-2 | MI0016687 | 2 | chr7 | 32732981 | 32733077 | − | — |
| hsa-mir-550b-1 | MI0016686 | 2 | chr7 | 30289794 | 30289890 | − | — |
| hsa-mir-550a-3 | MI0003762 | 16 | chr7 | 29680734 | 29680828 | − | ✓ |
| hsa-mir-550a-2 | MI0003601 | 16 | chr7 | 32732981 | 32733077 | + | ✓ |
| hsa-mir-550a-1 | MI0003600 | 16 | chr7 | 30289794 | 30289890 | + | ✓ |
| hsa-mir-549a | MI0003679 | — | chr15 | 80841978 | 80842073 | − | — |
| hsa-mir-548z | MI0016688 | 3 | chr12 | 64622509 | 64622605 | − | — |
| hsa-mir-548y | MI0016595 | 1 | chr14 | 47760995 | 47761104 | − | ✓ |
| hsa-mir-548x-2 | MI0016833 | 8 | chr13 | 65966330 | 65966429 | − | — |
| hsa-mir-548x | MI0014244 | 3 | chr21 | 18686090 | 18686164 | − | ✓ |
| hsa-mir-548w | MI0014222 | 3 | chr16 | 26025237 | 26025310 | + | — |
| hsa-mir-548v | MI0014174 | 9 | chr8 | 17681578 | 17681657 | − | ✓ |
| hsa-mir-548u | MI0014168 | 17 | chr6 | 57390132 | 57390212 | + | — |
| hsa-mir-548t | MI0014164 | 2 | chr4 | 173268160 | 173268233 | + | — |
| hsa-mir-548s | MI0014141 | 5 | chr2 | 11767444 | 11767525 | + | — |
| hsa-mir-548q | MI0010637 | 5 | chr10 | 12725254 | 12725353 | − | — |
| hsa-mir-548p | MI0006420 | 7 | chr5 | 100816482 | 100816565 | − | — |
| hsa-mir-548o-2 | MI0016746 | 15 | chr20 | 38516563 | 38516632 | + | ✓ |
| hsa-mir-548o | MI0006402 | 5 | chr7 | 102405742 | 102405855 | − | — |
| hsa-mir-548n | MI0006399 | 7 | chr7 | 34940760 | 34940834 | − | — |
| hsa-mir-548m | MI0006400 | — | chrX | 95063141 | 95063226 | − | — |
| hsa-mir-548l | MI0006361 | 8 | chr11 | 94466495 | 94466580 | − | — |
| hsa-mir-548k | MI0006354 | 15 | chr11 | 70283955 | 70284070 | + | ✓ |
| hsa-mir-548j | MI0006345 | 1 | chr22 | 26555212 | 26555323 | − | ✓ |
| hsa-mir-548l-4 | MI0006424 | 16 | chrX | 84225752 | 84225828 | − | — |
| hsa-mir-548l-3 | MI0006423 | 17 | chr8 | 8088941 | 8089089 | − | — |
| hsa-mir-548l-2 | MI0006422 | 17 | chr4 | 9556168 | 9556316 | − | — |
| hsa-mir-548l-1 | MI0006421 | 17 | chr3 | 125790404 | 125790552 | − | — |
| hsa-mir-548h-5 | MI0016751 | 2 | chr6 | 131792172 | 131792231 | + | — |
| hsa-mir-548h-4 | MI0006414 | 4 | chr8 | 27048853 | 27048963 | − | ✓ |
| hsa-mir-548h-3 | MI0006413 | 6 | chr17 | 13543529 | 13543646 | − | ✓ |
| hsa-mir-548h-2 | MI0006412 | 3 | chr16 | 11306440 | 11306527 | − | ✓ |

TABLE 2-continued

| miRNA ID | Accession | RPM | Chromosome | Start | End | Strand | Confidence |
|---|---|---|---|---|---|---|---|
| hsa-mir-548h-1 | MI0006411 | 2 | chr14 | 64095024 | 64095125 | − | − |
| hsa-mir-548g | MI0006395 | — | chr4 | 147344629 | 147344717 | − | − |
| hsa-mir-548f-5 | MI0006378 | — | chrX | 32641474 | 32641559 | − | − |
| hsa-mir-548f-4 | MI0006377 | 8 | chr7 | 147378017 | 147378121 | − | − |
| hsa-mir-548f-3 | MI0006376 | 3 | chr5 | 110513829 | 110513915 | − | − |
| hsa-mir-548f-2 | MI0006375 | 2 | chr2 | 212426263 | 212426360 | − | − |
| hsa-mir-548f-1 | MI0006374 | 3 | chr10 | 54607874 | 54607957 | − | − |
| hsa-mir-548e | MI0006344 | 14 | chr10 | 110988926 | 110989013 | + | ✓ |
| hsa-mir-548d-2 | MI0003671 | 15 | chr17 | 67471489 | 67471585 | − | ✓ |
| hsa-mir-548d-1 | MI0003668 | 12 | chr8 | 123348034 | 123348130 | − | ✓ |
| hsa-mir-548c | MI0003630 | 13 | chr12 | 64622509 | 64622605 | + | − |
| hsa-mir-548bc | MI0032315 | 1 | chr17 | 39297400 | 39297509 | + | − |
| hsa-mir-548bb | MI0029321 | — | chr3 | 60617805 | 60617870 | − | − |
| hsa-mir-548ba | MI0025747 | 8 | chr2 | 49059603 | 49059658 | + | − |
| hsa-mir-548b | MI0003596 | 35 | chr6 | 119069047 | 119069143 | − | ✓ |
| hsa-mir-548az | MI0022212 | 8 | chr8 | 119325171 | 119325265 | + | − |
| hsa-mir-548ay | MI0022210 | 8 | chr3 | 32506283 | 32506389 | − | ✓ |
| hsa-mir-548ax | MI0019286 | 1 | chrX | 11318614 | 11318686 | − | − |
| hsa-mir-548aw | MI0019283 | — | chr9 | 132945707 | 132945771 | + | − |
| hsa-mir-548av | MI0019152 | 25 | chr18 | 72853321 | 72853382 | − | − |
| hsa-mir-548au | MI0019145 | 8 | chr9 | 93594841 | 93594894 | + | − |
| hsa-mir-548at | MI0019137 | — | chr17 | 42494773 | 42494830 | + | ✓ |
| hsa-mir-548as | MI0019132 | 1 | chr13 | 92490163 | 92490220 | + | − |
| hsa-mir-548ar | MI0019131 | — | chr13 | 114244505 | 114244561 | + | ✓ |
| hsa-mir-548aq | MI0019130 | 3 | chr3 | 185767847 | 185767904 | − | ✓ |
| hsa-mir-548ap | MI0017875 | 2 | chr15 | 85825635 | 85825730 | + | ✓ |
| hsa-mir-548ao | MI0017871 | — | chr8 | 41271048 | 41271143 | − | − |
| hsa-mir-548an | MI0016907 | — | chrX | 106639814 | 106639896 | + | ✓ |
| hsa-mir-548am | MI0016904 | 16 | chrX | 16627012 | 16627085 | − | ✓ |
| hsa-mir-548al | MI0016851 | 1 | chr11 | 74399237 | 74399333 | + | − |
| hsa-mir-548ak | MI0016840 | 3 | chr10 | 12130760 | 12130816 | − | − |
| hsa-mir-548aj-2 | MI0016815 | 2 | chrX | 38023895 | 38023986 | − | − |
| hsa-mir-548aj-1 | MI0016814 | 2 | chr6 | 132115192 | 132115263 | − | − |
| hsa-mir-548ai | MI0016813 | — | chr6 | 99124609 | 99124696 | + | − |
| hsa-mir-548ah | MI0016796 | 7 | chr4 | 76575551 | 76575626 | + | − |
| hsa-mir-548ag-2 | MI0016794 | 4 | chr20 | 60564562 | 60564625 | + | ✓ |
| hsa-mir-548ag-1 | MI0016793 | 3 | chr4 | 60922619 | 60922684 | + | − |
| hsa-mir-548ae-2 | MI0016780 | 10 | chr5 | 58530043 | 58530109 | − | ✓ |
| hsa-mir-548ae-1 | MI0016779 | 15 | chr2 | 184378975 | 184379044 | + | − |

TABLE 2-continued

| miRNA ID | Accession | RPM | Chromosome | Start | End | Strand | Confidence |
|----------|-----------|-----|------------|-------|-----|--------|------------|
| hsa-mir-548ad | MI0016770 | 8 | chr2 | 35471405 | 35471486 | + | — |
| hsa-mir-548ac | MI0016762 | 6 | chr1 | 116560024 | 116560111 | − | — |
| hsa-mir-548ab | MI0016752 | 7 | chr3 | 103524033 | 103524116 | − | — |
| hsa-mir-548aa-2 | MI0016690 | 1 | chr17 | 67471489 | 67471585 | + | — |
| hsa-mir-548aa-1 | MI0016689 | 1 | chr8 | 123348034 | 123348130 | + | — |
| hsa-mir-548a-3 | MI0003612 | 18 | chr8 | 104484369 | 104484465 | − | ✓ |
| hsa-mir-548a-2 | MI0003598 | 25 | chr6 | 135239160 | 135239256 | + | — |
| hsa-mir-548a-1 | MI0003593 | 21 | chr6 | 18571784 | 18571880 | + | — |
| hsa-mir-545 | MI0003516 | 11 | chrX | 74287104 | 74287209 | − | ✓ |
| hsa-mir-544b | MI0014159 | 1 | chr3 | 124732439 | 124732516 | + | — |
| hsa-mir-544a | MI0003515 | 2 | chr14 | 101048658 | 101048748 | + | — |
| hsa-mir-543 | MI0005565 | 6 | chr14 | 101031987 | 101032064 | + | — |
| hsa-mir-542 | MI0003686 | 174 | chrX | 134541341 | 134541437 | − | ✓ |
| hsa-mir-541 | MI0005539 | 28 | chr14 | 101064495 | 101064578 | + | ✓ |
| hsa-mir-539 | MI0003514 | 4 | chr14 | 101047321 | 101047398 | + | ✓ |
| hsa-mir-532 | MI0003205 | 322 | chrX | 50003148 | 50003238 | + | ✓ |
| hsa-mir-527 | MI0003179 | 27 | chr19 | 53754018 | 53754102 | + | — |
| hsa-mir-526b | MI0003150 | 1 | chr19 | 53694393 | 53694475 | + | — |
| hsa-mir-526a-2 | MI0003168 | — | chr19 | 53726922 | 53726986 | + | — |
| hsa-mir-526a-1 | MI0003157 | 23 | chr19 | 53706252 | 53706336 | + | — |
| hsa-mir-525 | MI0003152 | 8 | chr19 | 53697533 | 53697617 | + | — |
| hsa-mir-524 | MI0003160 | 2 | chr19 | 53711002 | 53711088 | + | — |
| hsa-mir-523 | MI0003153 | 3 | chr19 | 53698385 | 53698471 | + | — |
| hsa-mir-522 | MI0003177 | 8 | chr19 | 53751211 | 53751297 | + | ✓ |
| hsa-mir-521-2 | MI0003163 | 13 | chr19 | 53716594 | 53716680 | + | — |
| hsa-mir-521-1 | MI0003176 | — | chr19 | 53748636 | 53748722 | + | — |
| hsa-mir-520h | MI0003175 | 18 | chr19 | 53742512 | 53742599 | + | — |
| hsa-mir-520g | MI0003166 | 17 | chr19 | 53722166 | 53722255 | + | — |
| hsa-mir-520f | MI0003146 | 4 | chr19 | 53682159 | 53682245 | + | — |
| hsa-mir-520e | MI0003143 | 33 | chr19 | 53675711 | 53675797 | + | — |
| hsa-mir-520d | MI0003164 | — | chr19 | 53720096 | 53720182 | + | — |
| hsa-mir-520c | MI0003158 | 6 | chr19 | 53707453 | 53707539 | + | ✓ |
| hsa-mir-520b | MI0003155 | 9 | chr19 | 53701227 | 53701287 | + | — |
| hsa-mir-520a | MI0003149 | 4 | chr19 | 53690881 | 53690965 | + | ✓ |
| hsa-mir-519e | MI0003145 | 10 | chr19 | 53679940 | 53680023 | + | — |
| hsa-mir-519d | MI0003162 | 3 | chr19 | 53713347 | 53713434 | + | — |
| hsa-mir-519c | MI0003148 | 14 | chr19 | 53686469 | 53686555 | + | — |
| hsa-mir-519b | MI0003151 | 8 | chr19 | 53695213 | 53695293 | + | ✓ |
| hsa-mir-519a-2 | MI0003182 | 8 | chr19 | 53762344 | 53762430 | + | ✓ |

TABLE 2-continued

| miRNA ID | Accession | RPM | Chromosome | Start | End | Strand | Confidence |
|---|---|---|---|---|---|---|---|
| hsa-mir-519a-1 | MI0003178 | 11 | chr19 | 53752397 | 53752481 | + | ✓ |
| hsa-mir-5197 | MI0018176 | — | chr5 | 143679860 | 143679971 | + | — |
| hsa-mir-5196 | MI0018175 | 20 | chr19 | 35345513 | 35345627 | + | — |
| hsa-mir-5195 | MI0018174 | — | chr14 | 106850885 | 106850999 | − | — |
| hsa-mir-5194 | MI0018173 | — | chr8 | 130008334 | 130008453 | − | — |
| hsa-mir-5193 | MI0018172 | 2 | chr3 | 49806137 | 49806245 | − | — |
| hsa-mir-5192 | MI0018171 | 4 | chr2 | 62205826 | 62205917 | + | — |
| hsa-mir-5191 | MI0018170 | 64 | chr1 | 201719508 | 201719627 | + | — |
| hsa-mir-5190 | MI0018169 | — | chr18 | 13459947 | 13460026 | + | — |
| hsa-mir-518f | MI0003154 | 6 | chr19 | 53700015 | 53700101 | + | — |
| hsa-mir-518e | MI0003169 | 3 | chr19 | 53729838 | 53729925 | + | — |
| hsa-mir-518d | MI0003171 | — | chr19 | 53734877 | 53734963 | + | — |
| hsa-mir-518c | MI0003159 | 5 | chr19 | 53708735 | 53708835 | + | — |
| hsa-mir-518b | MI0003156 | 6 | chr19 | 53702737 | 53702819 | + | — |
| hsa-mir-518a-2 | MI0003173 | — | chr19 | 53739333 | 53739419 | + | — |
| hsa-mir-518a-1 | MI0003170 | — | chr19 | 53731006 | 53731090 | + | — |
| hsa-mir-5189 | MI0018168 | — | chr16 | 88468918 | 88469031 | + | — |
| hsa-mir-5188 | MI0018167 | — | chr12 | 124915547 | 124915659 | + | — |
| hsa-mir-5187 | MI0018166 | 1 | chr1 | 161227186 | 161227261 | + | — |
| hsa-mir-5186 | MI0018165 | 13 | chr3 | 151565876 | 151565995 | − | — |
| hsa-mir-517c | MI0003174 | 1 | chr19 | 53741313 | 53741407 | + | — |
| hsa-mir-517b | MI0003165 | 1 | chr19 | 53721076 | 53721142 | + | — |
| hsa-mir-517a | MI0003161 | 1 | chr19 | 53712268 | 53712354 | + | — |
| hsa-mir-516b-2 | MI0003167 | — | chr19 | 53725442 | 53725526 | + | — |
| hsa-mir-516b-1 | MI0003172 | — | chr19 | 53736845 | 53736934 | + | — |
| hsa-mir-516a-2 | MI0003181 | 32 | chr19 | 53761133 | 53761222 | + | — |
| hsa-mir-516a-1 | MI0003180 | 31 | chr19 | 53756741 | 53756830 | + | — |
| hsa-mir-515-2 | MI0003147 | 7 | chr19 | 53685009 | 53685091 | + | — |
| hsa-mir-515-1 | MI0003144 | 7 | chr19 | 53679003 | 53679085 | + | — |
| hsa-mir-514b | MI0014251 | 573 | chrX | 147250151 | 147250230 | − | ✓ |
| hsa-mir-514a-3 | MI0003200 | 434 | chrX | 147284641 | 147284728 | − | ✓ |
| hsa-mir-514a-2 | MI0003199 | 434 | chrX | 147281943 | 147282030 | − | ✓ |
| hsa-mir-514a-1 | MI0003198 | 431 | chrX | 147279247 | 147279344 | − | ✓ |
| hsa-mir-513c | MI0006649 | 23 | chrX | 147189704 | 147189787 | − | ✓ |
| hsa-mir-513b | MI0006648 | 24 | chrX | 147199044 | 147199127 | − | — |
| hsa-mir-513a-2 | MI0003192 | 20 | chrX | 147225826 | 147225952 | − | ✓ |
| hsa-mir-513a-1 | MI0003191 | 23 | chrX | 147213463 | 147213591 | − | ✓ |
| hsa-mir-512-2 | MI0003141 | — | chr19 | 53669157 | 53669254 | + | ✓ |
| hsa-mir-512-1 | MI0003140 | — | chr19 | 53666679 | 53666762 | + | ✓ |

TABLE 2-continued

| miRNA ID | Accession | RPM | Chromosome | Start | End | Strand | Confidence |
|---|---|---|---|---|---|---|---|
| hsa-mir-511 | MI0003127 | — | chr10 | 17845107 | 17845193 | + | ✓ |
| hsa-mir-5100 | MI0019116 | 107 | chr10 | 42997563 | 42997681 | + | — |
| hsa-mir-510 | MI0003197 | 20 | chrX | 147272335 | 147272408 | – | ✓ |
| hsa-mir-5094 | MI0017983 | — | chr15 | 89850637 | 89850721 | – | — |
| hsa-mir-5093 | MI0017982 | 38 | chr16 | 85306226 | 85306325 | – | — |
| hsa-mir-5092 | MI0017981 | — | chr3 | 125151465 | 125151552 | – | — |
| hsa-mir-5091 | MI0017980 | 6 | chr4 | 13627865 | 13627957 | + | — |
| hsa-mir-5090 | MI0017979 | 2 | chr7 | 102465742 | 102465826 | + | — |
| hsa-mir-509-3 | MI0005717 | 352 | chrX | 147259652 | 147259726 | – | ✓ |
| hsa-mir-509-2 | MI0005530 | 259 | chrX | 147258760 | 147258850 | – | ✓ |
| hsa-mir-509-1 | MI0003196 | 259 | chrX | 147260532 | 147260625 | – | ✓ |
| hsa-mir-5089 | MI0017978 | 34 | chr17 | 46973017 | 46973100 | + | — |
| hsa-mir-5088 | MI0017977 | — | chr19 | 49682117 | 49682195 | + | — |
| hsa-mir-5087 | MI0017976 | — | chr1 | 148334479 | 148334554 | – | — |
| hsa-mir-508 | MI0003195 | 347 | chrX | 147236913 | 147237027 | – | ✓ |
| hsa-mir-507 | MI0003194 | 20 | chrX | 147230984 | 147231077 | – | — |
| hsa-mir-506 | MI0003193 | 55 | chrX | 147230720 | 147230843 | – | ✓ |
| hsa-mir-505 | MI0003190 | 86 | chrX | 139924148 | 139924231 | – | — |
| hsa-mir-5047 | MI0017932 | — | chr17 | 64501214 | 64501313 | – | — |
| hsa-mir-504 | MI0003189 | 4 | chrX | 138667711 | 138667793 | – | ✓ |
| hsa-mir-503 | MI0003188 | 132 | chrX | 134546328 | 134546398 | – | ✓ |
| hsa-mir-502 | MI0003186 | 58 | chrX | 50014598 | 50014683 | + | ✓ |
| hsa-mir-5011 | MI0017879 | — | chr18 | 67081584 | 67081686 | + | — |
| hsa-mir-5010 | MI0017878 | 1 | chr17 | 42514188 | 42514307 | + | ✓ |
| hsa-mir-501 | MI0003185 | 53 | chrX | 50009722 | 50009805 | + | ✓ |
| hsa-mir-500b | MI0015903 | 13 | chrX | 50010672 | 50010750 | + | — |
| hsa-mir-500a | MI0003184 | 63 | chrX | 50008431 | 50008514 | + | ✓ |
| hsa-mir-5009 | MI0017877 | — | chr15 | 89883931 | 89884030 | – | — |
| hsa-mir-5008 | MI0017876 | 1 | chr1 | 227941590 | 227941683 | – | — |
| hsa-mir-5007 | MI0017874 | — | chr13 | 55174454 | 55174548 | + | — |
| hsa-mir-5006 | MI0017873 | 8 | chr13 | 41568286 | 41568395 | – | — |
| hsa-mir-5004 | MI0017870 | 7 | chr6 | 33438331 | 33438437 | + | — |
| hsa-mir-5003 | MI0017869 | 12 | chr5 | 172662165 | 172662263 | + | — |
| hsa-mir-5002 | MI0017868 | 9 | chr3 | 124132929 | 124133025 | + | — |
| hsa-mir-5001 | MI0017867 | — | chr2 | 232550474 | 232550573 | – | ✓ |
| hsa-mir-5000 | MI0017866 | 11 | chr2 | 75090812 | 75090914 | + | ✓ |
| hsa-mir-499b | MI0017396 | 6 | chr20 | 34990400 | 34990472 | – | — |
| hsa-mir-499a | MI0003183 | 382 | chr20 | 34990376 | 34990497 | + | ✓ |
| hsa-mir-4999 | MI0017865 | 13 | chr19 | 8389290 | 8389380 | – | — |

TABLE 2-continued

| miRNA ID | Accession | RPM | Chromosome | Start | End | Strand | Confidence |
|---|---|---|---|---|---|---|---|
| hsa-mir-498 | MI0003142 | 54 | chr19 | 53674197 | 53674320 | + | — |
| hsa-mir-497 | MI0003138 | 267 | chr17 | 7017911 | 7018022 | − | — |
| hsa-mir-496 | MI0003136 | — | chr14 | 101060573 | 101060674 | + | — |
| hsa-mir-495 | MI0003135 | 91 | chr14 | 101033755 | 101033836 | + | ✓ |
| hsa-mir-494 | MI0003134 | 10 | chr14 | 101029634 | 101029714 | + | — |
| hsa-mir-493 | MI0003132 | 10 | chr14 | 100869060 | 100869148 | + | ✓ |
| hsa-mir-492 | MI0003131 | — | chr12 | 94834398 | 94834513 | + | — |
| hsa-mir-491 | MI0003126 | 4 | chr9 | 20716105 | 20716188 | + | ✓ |
| hsa-mir-490 | MI0003125 | 13 | chr7 | 136903167 | 136903294 | + | ✓ |
| hsa-mir-489 | MI0003124 | — | chr7 | 93483936 | 93484019 | − | — |
| hsa-mir-488 | MI0003123 | 16 | chr1 | 177029363 | 177029445 | − | ✓ |
| hsa-mir-487b | MI0003530 | 23 | chr14 | 101046455 | 101046538 | + | — |
| hsa-mir-487a | MI0002471 | — | chr14 | 101052446 | 101052525 | + | ✓ |
| hsa-mir-486-2 | MI0023622 | 645 | chr8 | 41660444 | 41660507 | + | ✓ |
| hsa-mir-486-1 | MI0002470 | 650 | chr8 | 41660441 | 41660508 | − | ✓ |
| hsa-mir-485 | MI0002469 | 9 | chr14 | 101055419 | 101055491 | + | ✓ |
| hsa-mir-484 | MI0002468 | 435 | chr16 | 15643294 | 15643372 | + | — |
| hsa-mir-483 | MI0002467 | 83 | chr11 | 2134134 | 2134209 | − | ✓ |
| hsa-mir-4804 | MI0017452 | 3 | chr5 | 72878591 | 72878663 | + | — |
| hsa-mir-4803 | MI0017451 | — | chr5 | 72169467 | 72169540 | + | — |
| hsa-mir-4802 | MI0017450 | — | chr4 | 40502040 | 40502119 | − | ✓ |
| hsa-mir-4801 | MI0017449 | — | chr4 | 37241910 | 37241991 | − | — |
| hsa-mir-4800 | MI0017448 | 4 | chr4 | 2250077 | 2250156 | − | — |
| hsa-mir-4799 | MI0017446 | — | chr4 | 147782595 | 147782668 | + | — |
| hsa-mir-4798 | MI0017445 | — | chr4 | 7310450 | 7310524 | + | — |
| hsa-mir-4797 | MI0017444 | — | chr3 | 197293878 | 197293948 | − | — |
| hsa-mir-4796 | MI0017443 | — | chr3 | 114743445 | 114743525 | − | — |
| hsa-mir-4795 | MI0017442 | — | chr3 | 87226189 | 87226277 | − | — |
| hsa-mir-4794 | MI0017441 | — | chr1 | 64579847 | 64579923 | + | — |
| hsa-mir-4793 | MI0017440 | 8 | chr3 | 48644194 | 48644280 | − | — |
| hsa-mir-4791 | MI0017438 | 3 | chr3 | 19314848 | 19314931 | − | — |
| hsa-mir-4790 | MI0017437 | 52 | chr3 | 5250177 | 5250255 | − | — |
| hsa-mir-4789 | MI0017436 | — | chr3 | 175369540 | 175369621 | + | — |
| hsa-mir-4788 | MI0017435 | 4 | chr3 | 134437827 | 134437906 | + | — |
| hsa-mir-4787 | MI0017434 | 4 | chr3 | 50675080 | 50675163 | + | — |
| hsa-mir-4786 | MI0017433 | — | chr2 | 239943015 | 239943094 | − | ✓ |
| hsa-mir-4785 | MI0017430 | — | chr2 | 160407810 | 160407882 | − | — |
| hsa-mir-4784 | MI0017429 | — | chr2 | 131491160 | 131491236 | − | — |
| hsa-mir-4783 | MI0017428 | — | chr2 | 127423537 | 127423618 | − | — |

TABLE 2-continued

| miRNA ID | Accession | RPM | Chromosome | Start | End | Strand | Confidence |
|---|---|---|---|---|---|---|---|
| hsa-mir-4782 | MI0017427 | — | chr2 | 113721290 | 113721368 | − | — |
| hsa-mir-4781 | MI0017426 | — | chr1 | 54054079 | 54054154 | + | — |
| hsa-mir-4780 | MI0017424 | — | chr2 | 88082519 | 88082599 | − | — |
| hsa-mir-4779 | MI0017423 | 11 | chr2 | 86193026 | 86193108 | − | — |
| hsa-mir-4778 | MI0017422 | 2 | chr2 | 66358249 | 66358328 | − | ✓ |
| hsa-mir-4777 | MI0017421 | — | chr2 | 231362708 | 231362793 | + | — |
| hsa-mir-4776-2 | MI0017420 | 114 | chr2 | 212926257 | 212926336 | − | — |
| hsa-mir-4776-1 | MI0017419 | 8 | chr2 | 212926257 | 212926336 | + | — |
| hsa-mir-4775 | MI0017418 | — | chr2 | 207754807 | 207754881 | + | — |
| hsa-mir-4774 | MI0017417 | — | chr2 | 168582943 | 168583018 | + | — |
| hsa-mir-4773-2 | MI0017416 | 18 | chr2 | 151368334 | 151368411 | − | — |
| hsa-mir-4773-1 | MI0017415 | 17 | chr2 | 151368334 | 151368411 | + | — |
| hsa-mir-4772 | MI0017414 | 1 | chr2 | 102432289 | 102432366 | + | — |
| hsa-mir-4771-2 | MI0017413 | — | chr2 | 111771061 | 111771134 | − | — |
| hsa-mir-4771-1 | MI0017412 | — | chr2 | 87194786 | 87194859 | + | — |
| hsa-mir-4770 | MI0017411 | — | chrX | 6383906 | 6383963 | − | — |
| hsa-mir-4769 | MI0017410 | — | chrX | 47587429 | 47587505 | + | — |
| hsa-mir-4768 | MI0017409 | — | chrX | 17425881 | 17425954 | + | — |
| hsa-mir-4767 | MI0017408 | 2 | chrX | 7147860 | 7147937 | + | — |
| hsa-mir-4766 | MI0017407 | 1 | chr22 | 40813883 | 40813958 | − | — |
| hsa-mir-4765 | MI0017406 | — | chr2 | 32635255 | 32635331 | + | — |
| hsa-mir-4764 | MI0017405 | — | chr22 | 33436582 | 33436669 | − | — |
| hsa-mir-4763 | MI0017404 | 5 | chr22 | 46113566 | 46113657 | + | — |
| hsa-mir-4762 | MI0017403 | — | chr22 | 45760524 | 45760598 | + | — |
| hsa-mir-4761 | MI0017402 | 8 | chr22 | 19963753 | 19963834 | + | ✓ |
| hsa-mir-4760 | MI0017401 | — | chr21 | 40212352 | 40212431 | − | — |
| hsa-mir-4759 | MI0017400 | — | chr21 | 26953961 | 26954043 | + | — |
| hsa-mir-4758 | MI0017399 | — | chr20 | 62332487 | 62332557 | − | — |
| hsa-mir-4757 | MI0017398 | — | chr2 | 19348429 | 19348505 | + | — |
| hsa-mir-4756 | MI0017397 | 11 | chr20 | 54068408 | 54068485 | − | — |
| hsa-mir-4755 | MI0017395 | — | chr20 | 34049119 | 34049190 | + | ✓ |
| hsa-mir-4754 | MI0017394 | — | chr19 | 58386770 | 58386858 | − | — |
| hsa-mir-4753 | MI0017392 | 1 | chr1 | 235190034 | 235190116 | − | — |
| hsa-mir-4752 | MI0017391 | — | chr19 | 54282109 | 54282180 | + | — |
| hsa-mir-4751 | MI0017390 | — | chr19 | 49933064 | 49933137 | + | — |
| hsa-mir-4750 | MI0017389 | — | chr19 | 49888175 | 49888230 | + | — |
| hsa-mir-4749 | MI0017388 | 9 | chr19 | 49854591 | 49854651 | + | — |
| hsa-mir-4748 | MI0017387 | — | chr19 | 10780254 | 10780335 | + | — |
| hsa-mir-4747 | MI0017386 | — | chr19 | 4932687 | 4932740 | + | — |

TABLE 2-continued

| miRNA ID | Accession | RPM | Chromosome | Start | End | Strand | Confidence |
|---|---|---|---|---|---|---|---|
| hsa-mir-4746 | MI0017385 | — | chr19 | 4445978 | 4446048 | + | — |
| hsa-mir-4745 | MI0017384 | — | chr19 | 804940 | 805001 | + | — |
| hsa-mir-4744 | MI0017382 | — | chr18 | 49049687 | 49049768 | − | — |
| hsa-mir-4743 | MI0017381 | — | chr18 | 48670600 | 48670668 | + | — |
| hsa-mir-4742 | MI0017380 | — | chr1 | 224398227 | 224398311 | − | — |
| hsa-mir-4741 | MI0017379 | — | chr18 | 22933349 | 22933438 | + | — |
| hsa-mir-4740 | MI0017378 | 26 | chr17 | 81400716 | 81400778 | − | — |
| hsa-mir-4739 | MI0017377 | 166 | chr17 | 79707176 | 79707249 | − | — |
| hsa-mir-4738 | MI0017376 | 3 | chr17 | 75784521 | 75784607 | − | — |
| hsa-mir-4737 | MI0017374 | — | chr17 | 60043025 | 60043105 | − | — |
| hsa-mir-4736 | MI0017373 | 282 | chr17 | 58335976 | 58336022 | − | — |
| hsa-mir-4735 | MI0017372 | 75 | chr1 | 196582413 | 196582481 | − | — |
| hsa-mir-4734 | MI0017371 | 2 | chr17 | 38702262 | 38702331 | − | — |
| hsa-mir-4733 | MI0017370 | — | chr17 | 31094350 | 31094425 | − | — |
| hsa-mir-4732 | MI0017369 | 1 | chr17 | 28861655 | 28861730 | − | — |
| hsa-mir-4731 | MI0017368 | — | chr17 | 15251627 | 15251696 | − | — |
| hsa-mir-4730 | MI0017367 | 8 | chr17 | 80419418 | 80419493 | + | — |
| hsa-mir-4729 | MI0017366 | — | chr17 | 59366083 | 59366154 | + | — |
| hsa-mir-4728 | MI0017365 | — | chr17 | 39726495 | 39726561 | + | — |
| hsa-mir-4727 | MI0017364 | — | chr17 | 38825838 | 38825892 | + | — |
| hsa-mir-4726 | MI0017363 | — | chr17 | 38719691 | 38719748 | + | — |
| hsa-mir-4725 | MI0017362 | 24 | chr17 | 31575269 | 31575358 | + | — |
| hsa-mir-4724 | MI0017361 | 2 | chr17 | 31534883 | 31534971 | + | — |
| hsa-mir-4723 | MI0017359 | 1 | chr17 | 28360654 | 28360734 | + | — |
| hsa-mir-4722 | MI0017357 | 11 | chr16 | 88716278 | 88716337 | − | — |
| hsa-mir-4721 | MI0017356 | — | chr16 | 28843919 | 28844007 | − | — |
| hsa-mir-4720 | MI0017355 | — | chr16 | 81385018 | 81385093 | + | — |
| hsa-mir-4719 | MI0017354 | 41 | chr16 | 76868936 | 76869019 | + | — |
| hsa-mir-4718 | MI0017353 | — | chr16 | 12720321 | 12720371 | + | — |
| hsa-mir-4717 | MI0017352 | — | chr16 | 2274620 | 2274691 | + | — |
| hsa-mir-4716 | MI0017350 | 5 | chr15 | 49169070 | 49169153 | − | — |
| hsa-mir-4715 | MI0017349 | — | chr15 | 25848747 | 25848825 | − | — |
| hsa-mir-4714 | MI0017348 | — | chr15 | 98784426 | 98784502 | + | — |
| hsa-mir-4713 | MI0017347 | 4 | chr15 | 51242190 | 51242264 | + | — |
| hsa-mir-4712 | MI0017346 | — | chr15 | 50360329 | 50360410 | + | — |
| hsa-mir-4711 | MI0017345 | — | chr1 | 59733227 | 59733296 | − | — |
| hsa-mir-4710 | MI0017344 | 2 | chr14 | 104677694 | 104677749 | − | — |
| hsa-mir-4709 | MI0017342 | 4 | chr14 | 74480133 | 74480204 | − | — |
| hsa-mir-4708 | MI0017341 | 8 | chr14 | 65335117 | 65335183 | − | — |

TABLE 2-continued

| miRNA ID | Accession | RPM | Chromosome | Start | End | Strand | Confidence |
|---|---|---|---|---|---|---|---|
| hsa-mir-4707 | MI0017340 | — | chr14 | 22956950 | 22957029 | − | — |
| hsa-mir-4706 | MI0017339 | 8 | chr14 | 65044688 | 65044769 | + | — |
| hsa-mir-4705 | MI0017338 | — | chr13 | 102045934 | 102046004 | − | — |
| hsa-mir-4704 | MI0017337 | — | chr13 | 66218250 | 66218324 | + | ✓ |
| hsa-mir-4703 | MI0017336 | — | chr13 | 51552589 | 51552667 | + | — |
| hsa-mir-4701 | MI0017334 | — | chr12 | 48771975 | 48772037 | − | — |
| hsa-mir-4700 | MI0017333 | — | chr12 | 120723193 | 120723266 | + | — |
| hsa-mir-4699 | MI0017332 | 29 | chr12 | 81158388 | 81158461 | + | — |
| hsa-mir-4698 | MI0017331 | — | chr12 | 47187812 | 47187891 | + | — |
| hsa-mir-4697 | MI0017330 | — | chr11 | 133898504 | 133898581 | − | — |
| hsa-mir-4696 | MI0017329 | — | chr11 | 74720268 | 74720337 | − | — |
| hsa-mir-4695 | MI0017328 | 2 | chr1 | 18883202 | 18883275 | − | — |
| hsa-mir-4694 | MI0017327 | 75 | chr11 | 19760004 | 19760083 | − | — |
| hsa-mir-4693 | MI0017326 | 5 | chr11 | 103849906 | 103849980 | + | — |
| hsa-mir-4692 | MI0017325 | — | chr11 | 72783530 | 72783592 | + | — |
| hsa-mir-4691 | MI0017324 | 9 | chr11 | 68033897 | 68033981 | + | — |
| hsa-mir-4690 | MI0017323 | — | chr11 | 65636310 | 65636369 | + | — |
| hsa-mir-4689 | MI0017322 | 30 | chr1 | 5862672 | 5862741 | − | — |
| hsa-mir-4688 | MI0017321 | 50 | chr11 | 46376402 | 46376484 | + | — |
| hsa-mir-4687 | MI0017319 | 5 | chr11 | 3856062 | 3856141 | + | — |
| hsa-mir-4686 | MI0017318 | 18 | chr11 | 2173063 | 2173138 | + | — |
| hsa-mir-4685 | MI0017317 | 26 | chr10 | 98431292 | 98431360 | − | — |
| hsa-mir-4684 | MI0017316 | 2 | chr1 | 22719517 | 22719598 | + | — |
| hsa-mir-4683 | MI0017315 | 1 | chr10 | 35641172 | 35641252 | − | — |
| hsa-mir-4682 | MI0017314 | — | chr10 | 119958513 | 119958592 | + | — |
| hsa-mir-4681 | MI0017313 | 19 | chr10 | 119377972 | 119378043 | + | — |
| hsa-mir-4680 | MI0017312 | — | chr10 | 110898090 | 110898155 | + | — |
| hsa-mir-4679-2 | MI0017311 | 4 | chr10 | 89063335 | 89063411 | − | — |
| hsa-mir-4679-1 | MI0017310 | 4 | chr10 | 89063336 | 89063410 | + | — |
| hsa-mir-4678 | MI0017309 | — | chr10 | 87503881 | 87503954 | + | — |
| hsa-mir-4677 | MI0017308 | 1 | chr1 | 243346176 | 243346255 | + | ✓ |
| hsa-mir-4676 | MI0017307 | — | chr10 | 72721029 | 72721100 | + | — |
| hsa-mir-4675 | MI0017306 | — | chr10 | 20551970 | 20552046 | + | — |
| hsa-mir-4674 | MI0017305 | 8 | chr9 | 136546173 | 136546259 | − | — |
| hsa-mir-4673 | MI0017304 | — | chr9 | 136519568 | 136519626 | − | — |
| hsa-mir-4672 | MI0017303 | 46 | chr9 | 127869415 | 127869495 | − | — |
| hsa-mir-4671 | MI0017302 | — | chr1 | 234306467 | 234306539 | + | — |
| hsa-mir-4670 | MI0017301 | — | chr9 | 92527984 | 92528058 | − | — |
| hsa-mir-4669 | MI0017300 | 2 | chr9 | 134379411 | 134379472 | + | — |

TABLE 2-continued

| miRNA ID | Accession | RPM | Chromosome | Start | End | Strand | Confidence |
|----------|-----------|-----|------------|-------|-----|--------|------------|
| hsa-mir-4668 | MI0017298 | — | chr9 | 111932100 | 111932169 | + | — |
| hsa-mir-4667 | MI0017297 | 3 | chr9 | 35608094 | 35608159 | + | — |
| hsa-mir-4666b | MI0019299 | — | chrX | 29574278 | 29574358 | + | — |
| hsa-mir-4666a | MI0017296 | — | chr1 | 228462074 | 228462152 | + | — |
| hsa-mir-4665 | MI0017295 | — | chr9 | 6007826 | 6007904 | + | — |
| hsa-mir-4664 | MI0017294 | — | chr8 | 143733083 | 143733153 | − | — |
| hsa-mir-4663 | MI0017292 | 110 | chr8 | 123215788 | 123215863 | − | — |
| hsa-mir-4662b | MI0017293 | 1 | chr8 | 124821978 | 124822058 | − | — |
| hsa-mir-4662a | MI0017290 | 2 | chr8 | 124821985 | 124822051 | + | — |
| hsa-mir-4661 | MI0017289 | — | chr8 | 91205485 | 91205559 | + | — |
| hsa-mir-4660 | MI0017288 | 22 | chr8 | 9048445 | 9048518 | + | — |
| hsa-mir-466 | MI0014157 | 13 | chr3 | 31161704 | 31161787 | − | — |
| hsa-mir-4659b | MI0017291 | — | chr8 | 6745168 | 6745240 | − | — |
| hsa-mir-4659a | MI0017287 | 2 | chr8 | 6745164 | 6745244 | + | — |
| hsa-mir-4658 | MI0017286 | — | chr7 | 100156605 | 100156669 | − | — |
| hsa-mir-4657 | MI0017285 | — | chr7 | 44881748 | 44881800 | − | — |
| hsa-mir-4656 | MI0017284 | 11 | chr7 | 4788565 | 4788639 | − | — |
| hsa-mir-4655 | MI0017283 | 2 | chr7 | 1844180 | 1844253 | − | — |
| hsa-mir-4654 | MI0017282 | — | chr1 | 162157107 | 162157182 | + | — |
| hsa-mir-4653 | MI0017281 | — | chr7 | 101159473 | 101159555 | + | — |
| hsa-mir-4652 | MI0017280 | — | chr7 | 93716928 | 93717005 | + | — |
| hsa-mir-4651 | MI0017279 | 5 | chr7 | 75915197 | 75915269 | + | — |
| hsa-mir-4650-2 | MI0017278 | — | chr7 | 72697903 | 72697978 | + | — |
| hsa-mir-4650-1 | MI0017277 | — | chr7 | 67114322 | 67114397 | − | — |
| hsa-mir-4649 | MI0017276 | — | chr7 | 44110849 | 44110912 | + | — |
| hsa-mir-4648 | MI0017275 | — | chr7 | 2527074 | 2527145 | + | — |
| hsa-mir-4647 | MI0017274 | 5 | chr6 | 44254206 | 44254285 | − | — |
| hsa-mir-4646 | MI0017273 | — | chr6 | 31701029 | 31701091 | − | — |
| hsa-mir-4645 | MI0017272 | — | chr6 | 2854031 | 2854107 | − | — |
| hsa-mir-4644 | MI0017271 | 5 | chr6 | 170330761 | 170330844 | + | — |
| hsa-mir-4643 | MI0017270 | — | chr6 | 91521660 | 91521737 | + | — |
| hsa-mir-4642 | MI0017269 | — | chr6 | 44435641 | 44435722 | + | — |
| hsa-mir-4641 | MI0017268 | 33 | chr6 | 41598723 | 41598788 | + | — |
| hsa-mir-4640 | MI0017267 | 3 | chr6 | 30890883 | 30890972 | + | — |
| hsa-mir-4639 | MI0017266 | — | chr6 | 16141556 | 16141624 | + | — |
| hsa-mir-4638 | MI0017265 | 1 | chr5 | 181222566 | 181222633 | − | — |
| hsa-mir-4637 | MI0017264 | — | chr5 | 14825929 | 14826012 | − | — |
| hsa-mir-4636 | MI0017263 | — | chr5 | 9053816 | 9053895 | − | — |
| hsa-mir-4635 | MI0017262 | 2 | chr5 | 1062896 | 1062974 | − | — |

TABLE 2-continued

| miRNA ID | Accession | RPM | Chromosome | Start | End | Strand | Confidence |
|---|---|---|---|---|---|---|---|
| hsa-mir-4634 | MI0017261 | — | chr5 | 174751734 | 174751787 | + | — |
| hsa-mir-4633 | MI0017260 | — | chr5 | 129097688 | 129097766 | + | — |
| hsa-mir-4632 | MI0017259 | — | chr1 | 12191713 | 12191773 | + | — |
| hsa-mir-455 | MI0003513 | 353 | chr9 | 114209434 | 114209529 | + | — |
| hsa-mir-4540 | MI0016911 | — | chr9 | 36864254 | 36864308 | − | — |
| hsa-mir-454 | MI0003820 | 207 | chr17 | 59137758 | 59137872 | − | ✓ |
| hsa-mir-4539 | MI0016910 | 8 | chr14 | 105857513 | 105857572 | − | — |
| hsa-mir-4538 | MI0016909 | 2 | chr14 | 105858165 | 105858242 | − | — |
| hsa-mir-4537 | MI0016908 | 2 | chr14 | 105859484 | 105859553 | − | — |
| hsa-mir-4536-2 | MI0019149 | 70 | chrX | 55451495 | 55451582 | + | — |
| hsa-mir-4536-1 | MI0016906 | — | chrX | 55451495 | 55451582 | − | — |
| hsa-mir-4535 | MI0016903 | — | chr22 | 48780295 | 48780353 | + | — |
| hsa-mir-4534 | MI0016901 | — | chr22 | 37988794 | 37988853 | + | — |
| hsa-mir-4533 | MI0016900 | 22 | chr20 | 60478111 | 60478181 | + | — |
| hsa-mir-4531 | MI0016898 | 42 | chr19 | 44653686 | 44653732 | − | — |
| hsa-mir-4530 | MI0016897 | — | chr19 | 39409623 | 39409678 | − | — |
| hsa-mir-4529 | MI0016896 | — | chr18 | 55479221 | 55479298 | + | — |
| hsa-mir-4528 | MI0016895 | — | chr18 | 53237101 | 53237190 | + | — |
| hsa-mir-4527 | MI0016894 | — | chr18 | 47380496 | 47380565 | + | — |
| hsa-mir-4526 | MI0016893 | — | chr18 | 13611114 | 13611200 | + | — |
| hsa-mir-4525 | MI0016892 | 4 | chr17 | 82668233 | 82668307 | − | — |
| hsa-mir-4524b | MI0019114 | 45 | chr17 | 69099542 | 69099656 | + | — |
| hsa-mir-4524a | MI0016891 | — | chr17 | 69099564 | 69099632 | − | ✓ |
| hsa-mir-4523 | MI0016890 | — | chr17 | 29390662 | 29390730 | + | — |
| hsa-mir-4522 | MI0016889 | — | chr17 | 27293910 | 27293996 | − | — |
| hsa-mir-4521 | MI0016887 | 654 | chr17 | 8186945 | 8187004 | + | — |
| hsa-mir-4520-2 | MI0017358 | — | chr17 | 6655449 | 6655502 | + | — |
| hsa-mir-4520-1 | MI0016886 | — | chr17 | 6655440 | 6655509 | − | — |
| hsa-mir-452 | MI0001733 | 123 | chrX | 151959628 | 151959712 | − | ✓ |
| hsa-mir-451b | MI0017360 | — | chr17 | 28861371 | 28861438 | + | — |
| hsa-mir-451a | MI0001729 | 3855 | chr17 | 28861369 | 28861440 | − | — |
| hsa-mir-4519 | MI0016885 | — | chr16 | 30875266 | 30875323 | − | — |
| hsa-mir-4518 | MI0016884 | 2 | chr16 | 30503919 | 30504001 | + | — |
| hsa-mir-4517 | MI0016883 | 10 | chr16 | 28958583 | 28958661 | + | — |
| hsa-mir-4516 | MI0016882 | 229 | chr16 | 2133119 | 2133204 | + | — |
| hsa-mir-4515 | MI0016881 | 4 | chr15 | 83067335 | 83067415 | + | — |
| hsa-mir-4514 | MI0016880 | — | chr15 | 80997417 | 80997473 | − | — |
| hsa-mir-4513 | MI0016879 | 16 | chr15 | 74788672 | 74788757 | − | — |
| hsa-mir-4512 | MI0016878 | 11 | chr15 | 66496958 | 66497034 | − | — |

TABLE 2-continued

| miRNA ID | Accession | RPM | Chromosome | Start | End | Strand | Confidence |
|---|---|---|---|---|---|---|---|
| hsa-mir-4511 | MI0016877 | 6 | chr15 | 65719246 | 65719332 | – | – |
| hsa-mir-4510 | MI0016876 | 237 | chr15 | 35926856 | 35926923 | + | – |
| hsa-mir-450b | MI0005531 | 27 | chrX | 134540185 | 134540262 | – | ✓ |
| hsa-mir-450a-2 | MI0003187 | 275 | chrX | 134540508 | 134540607 | – | ✓ |
| hsa-mir-450a-1 | MI0001652 | 275 | chrX | 134540341 | 134540431 | – | ✓ |
| hsa-mir-4509-3 | MI0016875 | – | chr15 | 28490752 | 28490845 | – | – |
| hsa-mir-4509-2 | MI0016874 | – | chr15 | 28426491 | 28426584 | + | – |
| hsa-mir-4509-1 | MI0016873 | – | chr15 | 23197827 | 23197920 | + | – |
| hsa-mir-4508 | MI0016872 | 31 | chr15 | 23562062 | 23562131 | – | – |
| hsa-mir-4507 | MI0016871 | – | chr14 | 105858124 | 105858175 | – | – |
| hsa-mir-4506 | MI0016869 | – | chr14 | 93948226 | 93948302 | – | – |
| hsa-mir-4505 | MI0016868 | – | chr14 | 73758747 | 73758819 | + | – |
| hsa-mir-4504 | MI0016867 | – | chr14 | 50299855 | 50299946 | – | – |
| hsa-mir-4503 | MI0016866 | 119 | chr14 | 36952309 | 36952391 | – | – |
| hsa-mir-4502 | MI0016865 | – | chr13 | 114273828 | 114273908 | + | – |
| hsa-mir-4501 | MI0016864 | – | chr13 | 96427229 | 96427292 | + | – |
| hsa-mir-4500 | MI0016863 | 106 | chr13 | 87618665 | 87618740 | – | – |
| hsa-mir-449c | MI0003823 | 9 | chr5 | 55172262 | 55172353 | – | – |
| hsa-mir-449b | MI0003673 | 120 | chr5 | 55170646 | 55170742 | – | – |
| hsa-mir-449a | MI0001648 | 102 | chr5 | 55170532 | 55170622 | – | – |
| hsa-mir-4499 | MI0016862 | – | chr13 | 20433778 | 20433846 | – | – |
| hsa-mir-4498 | MI0016860 | 46 | chr12 | 120155434 | 120155499 | – | – |
| hsa-mir-4497 | MI0016859 | 96 | chr12 | 109833348 | 109833436 | + | – |
| hsa-mir-4496 | MI0016858 | – | chr12 | 108635810 | 108635870 | + | – |
| hsa-mir-4495 | MI0016857 | – | chr12 | 97939056 | 97939121 | – | – |
| hsa-mir-4494 | MI0016856 | – | chr12 | 47364186 | 47364269 | – | – |
| hsa-mir-4493 | MI0016855 | 23 | chr11 | 123381440 | 123381512 | – | – |
| hsa-mir-4492 | MI0016854 | 12 | chr11 | 118910708 | 118910787 | + | – |
| hsa-mir-4491 | MI0016853 | – | chr11 | 111347757 | 111347824 | + | – |
| hsa-mir-4490 | MI0016852 | – | chr11 | 90555774 | 90555857 | – | – |
| hsa-mir-4489 | MI0016850 | – | chr11 | 65649192 | 65649253 | + | – |
| hsa-mir-4488 | MI0016849 | 67 | chr11 | 61508596 | 61508657 | + | – |
| hsa-mir-4487 | MI0016848 | – | chr11 | 47400970 | 47401042 | + | ✓ |
| hsa-mir-4486 | MI0016847 | – | chr11 | 19575310 | 19575372 | + | – |
| hsa-mir-4485 | MI0016846 | 20 | chr11 | 10508270 | 10508326 | – | – |
| hsa-mir-4484 | MI0016845 | 24 | chr10 | 125819740 | 125819822 | + | – |
| hsa-mir-4483 | MI0016844 | – | chr10 | 113777993 | 113778054 | – | – |
| hsa-mir-4482 | MI0016843 | – | chr10 | 104268336 | 104268405 | – | – |
| hsa-mir-4481 | MI0016842 | – | chr10 | 12653138 | 12653197 | – | – |

TABLE 2-continued

| miRNA ID | Accession | RPM | Chromosome | Start | End | Strand | Confidence |
|---|---|---|---|---|---|---|---|
| hsa-mir-4480 | MI0016841 | 100 | chr10 | 12578753 | 12578823 | + | — |
| hsa-mir-448 | MI0001637 | — | chrX | 114823454 | 114823564 | + | — |
| hsa-mir-4479 | MI0016838 | — | chr9 | 136886733 | 136886803 | + | — |
| hsa-mir-4478 | MI0016831 | — | chr9 | 122120082 | 122120167 | − | — |
| hsa-mir-4477b | MI0016830 | 11 | chr9 | 41233755 | 41233835 | − | — |
| hsa-mir-4477a | MI0016829 | 3 | chr9 | 41233755 | 41233835 | + | — |
| hsa-mir-4476 | MI0016828 | — | chr9 | 36893462 | 36893531 | − | — |
| hsa-mir-4475 | MI0016827 | — | chr9 | 36823539 | 36823599 | − | — |
| hsa-mir-4474 | MI0016826 | — | chr9 | 20502265 | 20502342 | − | — |
| hsa-mir-4473 | MI0016825 | — | chr9 | 20411148 | 20411238 | − | — |
| hsa-mir-4472-2 | MI0016824 | 65 | chr12 | 116428252 | 116428318 | − | — |
| hsa-mir-4472-1 | MI0016823 | 24 | chr8 | 142176339 | 142176418 | + | — |
| hsa-mir-4471 | MI0016822 | — | chr8 | 100382763 | 100382845 | + | — |
| hsa-mir-4470 | MI0016821 | — | chr8 | 61714788 | 61714859 | + | — |
| hsa-mir-4469 | MI0016820 | — | chr8 | 42896197 | 42896275 | − | — |
| hsa-mir-4468 | MI0016819 | — | chr7 | 138123758 | 138123821 | + | — |
| hsa-mir-4467 | MI0016818 | — | chr7 | 102471469 | 102471531 | + | — |
| hsa-mir-4466 | MI0016817 | 1 | chr6 | 156779678 | 156779731 | − | — |
| hsa-mir-4465 | MI0016816 | — | chr6 | 140683814 | 140683883 | + | — |
| hsa-mir-4464 | MI0016812 | — | chr6 | 90312742 | 90312833 | + | — |
| hsa-mir-4463 | MI0016811 | — | chr6 | 75428407 | 75428473 | + | — |
| hsa-mir-4462 | MI0016810 | — | chr6 | 37555365 | 37555422 | − | — |
| hsa-mir-4460 | MI0016806 | — | chr5 | 129397062 | 129397147 | − | — |
| hsa-mir-4458 | MI0016804 | — | chr5 | 8460925 | 8460999 | + | — |
| hsa-mir-4457 | MI0016803 | — | chr5 | 1309310 | 1309377 | − | — |
| hsa-mir-4456 | MI0016802 | — | | | | | — |
| hsa-mir-4455 | MI0016801 | 30 | chr4 | 184938383 | 184938440 | − | — |
| hsa-mir-4454 | MI0016800 | 457 | chr4 | 163093574 | 163093628 | − | — |
| hsa-mir-4453 | MI0016799 | — | chr4 | 152536428 | 152536516 | + | — |
| hsa-mir-4452 | MI0016798 | 7 | chr4 | 86542482 | 86542552 | − | — |
| hsa-mir-4451 | MI0016797 | 13 | chr4 | 85722468 | 85722533 | + | — |
| hsa-mir-4450 | MI0016795 | — | chr4 | 76573568 | 76573632 | + | — |
| hsa-mir-4449 | MI0016792 | 943 | chr4 | 52712682 | 52712747 | + | — |
| hsa-mir-4448 | MI0016791 | 59 | chr3 | 183886800 | 183886885 | + | — |
| hsa-mir-4447 | MI0016790 | — | chr3 | 116850277 | 116850367 | − | — |
| hsa-mir-4446 | MI0016789 | 1 | chr3 | 113594876 | 113594942 | + | — |
| hsa-mir-4445 | MI0016788 | 100 | chr3 | 109602828 | 109602897 | + | — |
| hsa-mir-4444-2 | MI0019111 | 9 | chr3 | 75214476 | 75214549 | + | — |
| hsa-mir-4444-1 | MI0016787 | 9 | chr2 | 177212726 | 177212799 | + | — |

TABLE 2-continued

| miRNA ID | Accession | RPM | Chromosome | Start | End | Strand | Confidence |
|---|---|---|---|---|---|---|---|
| hsa-mir-4443 | MI0016786 | 872 | chr3 | 48196564 | 48196616 | + | — |
| hsa-mir-4442 | MI0016785 | 6 | chr3 | 25664873 | 25664939 | − | — |
| hsa-mir-4441 | MI0016784 | — | chr2 | 239085827 | 239085926 | − | — |
| hsa-mir-4440 | MI0016783 | — | chr2 | 239068817 | 239068914 | − | — |
| hsa-mir-4439 | MI0016782 | — | chr2 | 225010461 | 225010540 | − | — |
| hsa-mir-4438 | MI0016781 | 138 | chr2 | 213758067 | 213758159 | + | — |
| hsa-mir-4437 | MI0016778 | — | chr2 | 181305593 | 181305652 | − | — |
| hsa-mir-4436b-2 | MI0019110 | 7 | chr2 | 110284853 | 110284943 | + | — |
| hsa-mir-4436b-1 | MI0017425 | 7 | chr2 | 110086433 | 110086523 | − | — |
| hsa-mir-4436a | MI0016776 | — | chr2 | 88812370 | 88812454 | + | — |
| hsa-mir-4435-2 | MI0016777 | — | chr2 | 111321013 | 111321086 | − | — |
| hsa-mir-4435-1 | MI0016775 | — | chr2 | 87629755 | 87629834 | + | — |
| hsa-mir-4434 | MI0016774 | — | chr2 | 64525513 | 64525565 | + | — |
| hsa-mir-4433b | MI0025511 | — | chr2 | 64340747 | 64340848 | − | — |
| hsa-mir-4433a | MI0016773 | 5 | chr2 | 64340759 | 64340839 | + | — |
| hsa-mir-4432 | MI0016772 | 16 | chr2 | 60387362 | 60387445 | − | — |
| hsa-mir-4431 | MI0016771 | 5 | chr2 | 52702522 | 52702615 | − | — |
| hsa-mir-4430 | MI0016769 | 12 | chr2 | 33418516 | 33418564 | + | — |
| hsa-mir-4429 | MI0016768 | 1989 | chr2 | 11540605 | 11540677 | − | — |
| hsa-mir-4428 | MI0016767 | — | chr1 | 237471119 | 237471191 | + | — |
| hsa-mir-4427 | MI0016766 | — | chr1 | 233624152 | 233624219 | + | — |
| hsa-mir-4426 | MI0016765 | — | chr1 | 192716328 | 192716390 | + | — |
| hsa-mir-4425 | MI0016764 | 14 | chr1 | 25023503 | 25023586 | + | — |
| hsa-mir-4424 | MI0016763 | — | chr1 | 178677749 | 178677834 | + | — |
| hsa-mir-4423 | MI0016760 | 10 | chr1 | 85133794 | 85133873 | + | ✓ |
| hsa-mir-4422 | MI0016759 | — | chr1 | 55225641 | 55225723 | + | — |
| hsa-mir-4421 | MI0016758 | — | chr1 | 51059837 | 51059905 | + | — |
| hsa-mir-4420 | MI0016757 | — | chr1 | 30739156 | 30739232 | − | — |
| hsa-mir-4418 | MI0016754 | 44 | chr1 | 22266239 | 22266300 | + | — |
| hsa-mir-4330 | MI0015902 | 11 | chrX | 151168222 | 151168326 | + | — |
| hsa-mir-433 | MI0001723 | 2 | chr14 | 100881886 | 100881978 | + | ✓ |
| hsa-mir-4329 | MI0015901 | 4 | chrX | 112780718 | 112780788 | − | — |
| hsa-mir-4328 | MI0015904 | 80 | chrX | 78901194 | 78901249 | − | — |
| hsa-mir-4327 | MI0015867 | 57 | chr21 | 30375294 | 30375378 | − | — |
| hsa-mir-4326 | MI0015866 | — | chr20 | 63286808 | 63286866 | + | — |
| hsa-mir-4325 | MI0015865 | — | chr20 | 57321502 | 57321591 | − | — |
| hsa-mir-4324 | MI0015854 | 56 | chr19 | 49308797 | 49308868 | − | — |
| hsa-mir-4323 | MI0015853 | — | chr19 | 42133445 | 42133513 | − | — |
| hsa-mir-4322 | MI0015851 | 9 | chr19 | 10230413 | 10230485 | + | — |

TABLE 2-continued

| miRNA ID | Accession | RPM | Chromosome | Start | End | Strand | Confidence |
|---|---|---|---|---|---|---|---|
| hsa-mir-4321 | MI0015852 | — | chr19 | 2250639 | 2250718 | + | — |
| hsa-mir-4320 | MI0015849 | — | chr18 | 50126499 | 50126563 | − | — |
| hsa-mir-432 | MI0003133 | 55 | chr14 | 100884483 | 100884576 | + | — |
| hsa-mir-4319 | MI0015848 | — | chr18 | 44970082 | 44970166 | − | — |
| hsa-mir-4318 | MI0015847 | 62 | chr18 | 37657135 | 37657215 | + | — |
| hsa-mir-4317 | MI0015850 | 1 | chr18 | 6374361 | 6374425 | − | — |
| hsa-mir-4316 | MI0015845 | 209 | chr17 | 77396984 | 77397054 | − | — |
| hsa-mir-4315-2 | MI0015983 | — | chr17 | 64822030 | 64822102 | − | — |
| hsa-mir-4315-1 | MI0015844 | — | chr17 | 45475363 | 45475435 | − | — |
| hsa-mir-4314 | MI0015846 | 150 | chr17 | 8088056 | 8088147 | + | — |
| hsa-mir-4313 | MI0015843 | 28 | chr15 | 75762215 | 75762315 | − | — |
| hsa-mir-4312 | MI0015842 | 57 | chr15 | 68801850 | 68801925 | − | — |
| hsa-mir-4311 | MI0015841 | 56 | chr15 | 66040233 | 66040332 | + | — |
| hsa-mir-4310 | MI0015840 | 77 | chr15 | 41866495 | 41866551 | − | — |
| hsa-mir-431 | MI0001721 | — | chr14 | 100881007 | 100881120 | + | — |
| hsa-mir-4309 | MI0015837 | — | chr14 | 102539644 | 102539726 | + | — |
| hsa-mir-4308 | MI0015839 | 6 | chr14 | 54878113 | 54878193 | − | — |
| hsa-mir-4307 | MI0015838 | — | chr14 | 26908642 | 26908725 | + | — |
| hsa-mir-4306 | MI0015836 | 135 | chr13 | 99643059 | 99643149 | + | — |
| hsa-mir-4305 | MI0015835 | 214 | chr13 | 39664034 | 39664135 | − | — |
| hsa-mir-4304 | MI0015832 | 13 | chr12 | 123010667 | 123010728 | − | — |
| hsa-mir-4303 | MI0015834 | — | chr12 | 97995383 | 97995448 | − | — |
| hsa-mir-4302 | MI0015833 | — | chr12 | 25874020 | 25874079 | − | — |
| hsa-mir-4301 | MI0015828 | 8 | chr11 | 113450023 | 113450088 | − | — |
| hsa-mir-4300 | MI0015831 | — | chr11 | 81890741 | 81890836 | − | — |
| hsa-mir-4299 | MI0015829 | — | chr11 | 11656651 | 11656722 | − | — |
| hsa-mir-4298 | MI0015830 | 9 | chr11 | 1859464 | 1859536 | − | — |
| hsa-mir-4297 | MI0015824 | — | chr10 | 129843299 | 129843374 | − | — |
| hsa-mir-4296 | MI0015823 | 6 | chr10 | 125032783 | 125032870 | − | — |
| hsa-mir-4295 | MI0015822 | — | chr10 | 112634170 | 112634254 | + | — |
| hsa-mir-4294 | MI0015827 | 171 | chr10 | 48985512 | 48985587 | − | — |
| hsa-mir-4293 | MI0015826 | — | chr10 | 14383200 | 14383277 | − | — |
| hsa-mir-4292 | MI0015897 | — | chr9 | 136830957 | 136831023 | + | — |
| hsa-mir-4291 | MI0015900 | — | chr9 | 93819357 | 93819421 | + | — |
| hsa-mir-4290 | MI0015899 | 145 | chr9 | 90023441 | 90023535 | − | — |
| hsa-mir-429 | MI0001641 | 381 | chr1 | 1169005 | 1169087 | + | — |
| hsa-mir-4289 | MI0015898 | 852 | chr9 | 88745836 | 88745905 | − | — |
| hsa-mir-4288 | MI0015896 | 8 | chr8 | 28505116 | 28505182 | − | — |
| hsa-mir-4287 | MI0015895 | — | chr8 | 27886039 | 27886116 | − | — |

TABLE 2-continued

| miRNA ID | Accession | RPM | Chromosome | Start | End | Strand | Confidence |
|---|---|---|---|---|---|---|---|
| hsa-mir-4286 | MI0015894 | 310 | chr8 | 10666978 | 10667070 | + | — |
| hsa-mir-4285 | MI0015891 | 7 | chr7 | 102293103 | 102293187 | + | — |
| hsa-mir-4284 | MI0015893 | 22 | chr7 | 73711317 | 73711397 | + | — |
| hsa-mir-4283-2 | MI0015982 | — | chr7 | 63621090 | 63621169 | + | — |
| hsa-mir-4283-1 | MI0015892 | — | chr7 | 56955785 | 56955864 | − | — |
| hsa-mir-4282 | MI0015890 | — | chr6 | 72967687 | 72967753 | − | — |
| hsa-mir-4281 | MI0015885 | 11 | chr5 | 176629439 | 176629500 | − | — |
| hsa-mir-4280 | MI0015889 | — | chr5 | 87114879 | 87114954 | − | — |
| hsa-mir-4279 | MI0015887 | 13 | chr5 | 31936102 | 31936159 | − | — |
| hsa-mir-4278 | MI0015888 | — | chr5 | 6827853 | 6827921 | − | — |
| hsa-mir-4277 | MI0015886 | — | chr5 | 1708785 | 1708868 | − | — |
| hsa-mir-4276 | MI0015882 | — | chr4 | 174423795 | 174423864 | + | — |
| hsa-mir-4275 | MI0015883 | 266 | chr4 | 28819582 | 28819668 | + | — |
| hsa-mir-4274 | MI0015884 | 33 | chr4 | 7460028 | 7460118 | + | — |
| hsa-mir-4273 | MI0015881 | — | chr3 | 75738280 | 75738363 | + | — |
| hsa-mir-4272 | MI0015880 | — | chr3 | 67225464 | 67225527 | + | — |
| hsa-mir-4271 | MI0015879 | 24 | chr3 | 49274120 | 49274186 | + | — |
| hsa-mir-4270 | MI0015878 | 14 | chr3 | 15496239 | 15496308 | − | — |
| hsa-mir-4269 | MI0015875 | — | chr2 | 239305462 | 239305545 | + | — |
| hsa-mir-4268 | MI0015874 | — | chr2 | 219906502 | 219906565 | − | — |
| hsa-mir-4267 | MI0015871 | — | chr2 | 110069961 | 110070042 | − | — |
| hsa-mir-4266 | MI0015870 | — | chr2 | 109313571 | 109313625 | − | — |
| hsa-mir-4265 | MI0015869 | 5 | chr2 | 109141490 | 109141588 | − | — |
| hsa-mir-4264 | MI0015877 | 877 | chr2 | 79649294 | 79649359 | − | — |
| hsa-mir-4263 | MI0015876 | — | chr2 | 27996367 | 27996449 | + | — |
| hsa-mir-4262 | MI0015872 | — | chr2 | 11836933 | 11836986 | − | — |
| hsa-mir-4261 | MI0015868 | — | chr2 | 10192614 | 10192671 | − | — |
| hsa-mir-4260 | MI0015859 | 350 | chr1 | 209623444 | 209623510 | − | — |
| hsa-mir-4259 | MI0015858 | 10 | chr1 | 159899979 | 159900079 | − | — |
| hsa-mir-4258 | MI0015857 | 9 | chr1 | 154975693 | 154975783 | + | — |
| hsa-mir-4257 | MI0015856 | 12 | chr1 | 150551929 | 150552014 | + | — |
| hsa-mir-4256 | MI0015855 | — | chr1 | 112461770 | 112461833 | − | — |
| hsa-mir-4255 | MI0015863 | — | chr1 | 37161563 | 37161634 | + | — |
| hsa-mir-4254 | MI0015862 | — | chr1 | 31758660 | 31758735 | − | — |
| hsa-mir-4253 | MI0015860 | — | chr1 | 22863159 | 22863226 | − | — |
| hsa-mir-4252 | MI0015864 | — | chr1 | 6429834 | 6429896 | − | — |
| hsa-mir-4251 | MI0015861 | — | chr1 | 3127975 | 3128035 | + | — |
| hsa-mir-425 | MI0001448 | 1131 | chr3 | 49020148 | 49020234 | − | ✓ |
| hsa-mir-424 | MI0001446 | 3666 | chrX | 134546614 | 134546711 | − | ✓ |

TABLE 2-continued

| miRNA ID | Accession | RPM | Chromosome | Start | End | Strand | Confidence |
|---|---|---|---|---|---|---|---|
| hsa-mir-423 | MI0001445 | 3706 | chr17 | 30117079 | 30117172 | + | ✓ |
| hsa-mir-422a | MI0001444 | 7 | chr15 | 63870930 | 63871019 | − | − |
| hsa-mir-421 | MI0003685 | 120 | chrX | 74218377 | 74218461 | − | ✓ |
| hsa-mir-412 | MI0002464 | — | chr14 | 101065447 | 101065537 | + | − |
| hsa-mir-411 | MI0003675 | 86 | chr14 | 101023325 | 101023420 | + | ✓ |
| hsa-mir-410 | MI0002465 | 12 | chr14 | 101065912 | 101065991 | + | ✓ |
| hsa-mir-409 | MI0001735 | 3 | chr14 | 101065300 | 101065378 | + | ✓ |
| hsa-mir-3978 | MI0016996 | — | chrX | 110082118 | 110082218 | + | − |
| hsa-mir-3977 | MI0016995 | — | chr5 | 82840155 | 82840224 | + | − |
| hsa-mir-3976 | MI0016994 | — | chr18 | 5840695 | 5840833 | + | − |
| hsa-mir-3975 | MI0016993 | 100 | chr18 | 35591737 | 35591806 | + | − |
| hsa-mir-3974 | MI0016992 | — | chr12 | 17673299 | 17673394 | + | − |
| hsa-mir-3973 | MI0016991 | 200 | chr11 | 36010098 | 36010204 | + | − |
| hsa-mir-3972 | MI0016990 | 122 | chr1 | 17277889 | 17277975 | + | − |
| hsa-mir-3960 | MI0016964 | 95 | chr9 | 127785833 | 127785923 | + | − |
| hsa-mir-3945 | MI0016602 | — | chr4 | 184851013 | 184851110 | − | − |
| hsa-mir-3944 | MI0016601 | 10 | chr10 | 133371556 | 133371663 | − | ✓ |
| hsa-mir-3943 | MI0016600 | — | chr7 | 43150895 | 43150994 | + | − |
| hsa-mir-3942 | MI0016599 | — | chr15 | 35372256 | 35372364 | − | ✓ |
| hsa-mir-3941 | MI0016598 | — | chr10 | 122416965 | 122417067 | + | − |
| hsa-mir-3940 | MI0016597 | — | chr19 | 6416410 | 6416511 | − | − |
| hsa-mir-3939 | MI0016596 | — | chr6 | 166997807 | 166997912 | − | − |
| hsa-mir-3938 | MI0016594 | — | chr3 | 55852492 | 55852594 | − | − |
| hsa-mir-3937 | MI0016593 | — | chrX | 39661216 | 39661321 | + | − |
| hsa-mir-3936 | MI0016592 | — | chr5 | 132365490 | 132365599 | − | − |
| hsa-mir-3935 | MI0016591 | 3 | chr16 | 56245520 | 56245623 | + | − |
| hsa-mir-3934 | MI0016590 | 1 | chr6 | 33698128 | 33698234 | + | − |
| hsa-mir-3929 | MI0016439 | 238 | chr18 | 35934088 | 35934142 | − | − |
| hsa-mir-3928 | MI0016438 | 1 | chr22 | 31160062 | 31160119 | − | − |
| hsa-mir-3927 | MI0016435 | — | chr9 | 109511475 | 109511545 | − | − |
| hsa-mir-3926-2 | MI0016437 | 6 | chr8 | 12727237 | 12727299 | + | − |
| hsa-mir-3926-1 | MI0016434 | 5 | chr8 | 12727232 | 12727304 | − | − |
| hsa-mir-3925 | MI0016433 | — | chr6 | 36622436 | 36622512 | − | − |
| hsa-mir-3924 | MI0016432 | 100 | chr10 | 57304479 | 57304559 | − | − |
| hsa-mir-3923 | MI0016430 | — | chr3 | 79507887 | 79507969 | + | − |
| hsa-mir-3922 | MI0016429 | — | chr12 | 104591633 | 104591716 | + | − |
| hsa-mir-3921 | MI0016428 | 4 | chr3 | 99964314 | 99964398 | − | − |
| hsa-mir-3920 | MI0016427 | — | chr11 | 101519820 | 101519905 | − | − |
| hsa-mir-3919 | MI0016425 | — | chr3 | 159282646 | 159282734 | + | − |

TABLE 2-continued

| miRNA ID | Accession | RPM | Chromosome | Start | End | Strand | Confidence |
|----------|-----------|-----|------------|-------|-----|--------|------------|
| hsa-mir-3918 | MI0016424 | — | chr6 | 158764661 | 158764753 | − | — |
| hsa-mir-3917 | MI0016423 | 3 | chr1 | 25906362 | 25906454 | − | — |
| hsa-mir-3916 | MI0016422 | 14 | chr1 | 247201967 | 247202060 | − | — |
| hsa-mir-3915 | MI0016420 | — | chrX | 32583656 | 32583752 | − | — |
| hsa-mir-3914-2 | MI0016421 | — | chr7 | 71307674 | 71307768 | + | — |
| hsa-mir-3914-1 | MI0016419 | — | chr7 | 71307672 | 71307770 | + | — |
| hsa-mir-3913-2 | MI0016418 | 4 | chr12 | 69584723 | 69584822 | + | — |
| hsa-mir-3913-1 | MI0016417 | 2 | chr12 | 69584722 | 69584823 | − | — |
| hsa-mir-3912 | MI0016416 | — | chr5 | 171386656 | 171386760 | − | — |
| hsa-mir-3911 | MI0016415 | 1 | chr9 | 127690687 | 127690795 | − | — |
| hsa-mir-3910-2 | MI0016431 | 2 | chr9 | 91636264 | 91636345 | − | — |
| hsa-mir-3910-1 | MI0016414 | 2 | chr9 | 91636251 | 91636361 | + | — |
| hsa-mir-3909 | MI0016413 | — | chr22 | 35335640 | 35335758 | + | ✓ |
| hsa-mir-3908 | MI0016412 | 72 | chr12 | 123536409 | 123536534 | + | — |
| hsa-mir-3907 | MI0016410 | 36 | chr7 | 151433489 | 151433639 | − | — |
| hsa-mir-384 | MI0001145 | — | chrX | 76919273 | 76919360 | − | — |
| hsa-mir-383 | MI0000791 | 8 | chr8 | 14853438 | 14853510 | − | — |
| hsa-mir-382 | MI0000790 | 23 | chr14 | 101054306 | 101054381 | + | ✓ |
| hsa-mir-381 | MI0000789 | 22 | chr14 | 101045920 | 101045994 | + | ✓ |
| hsa-mir-380 | MI0000788 | 1 | chr14 | 101025017 | 101025077 | + | ✓ |
| hsa-mir-379 | MI0000787 | 263 | chr14 | 101022066 | 101022132 | + | ✓ |
| hsa-mir-378j | MI0021273 | 7 | chr17 | 37614931 | 37615039 | − | — |
| hsa-mir-3781 | MI0016902 | 5084 | chr22 | 41923222 | 41923297 | − | — |
| hsa-mir-378h | MI0016808 | 3791 | chr5 | 154829458 | 154829540 | + | — |
| hsa-mir-378g | MI0016761 | 4642 | | | | | — |
| hsa-mir-378f | MI0016756 | 4762 | chr1 | 23929070 | 23929147 | + | — |
| hsa-mir-378e | MI0016750 | 3130 | chr5 | 170028488 | 170028566 | + | — |
| hsa-mir-378d-2 | MI0003840 | 4789 | chr8 | 93916022 | 93916119 | − | — |
| hsa-mir-378d-1 | MI0016749 | 3415 | chr4 | 5923275 | 5923328 | − | — |
| hsa-mir-378c | MI0015825 | 4978 | chr10 | 130962588 | 130962668 | − | — |
| hsa-mir-378b | MI0014154 | 3955 | chr3 | 10330229 | 10330285 | + | — |
| hsa-mir-378a | MI0000786 | 6009 | chr5 | 149732825 | 149732890 | + | ✓ |
| hsa-mir-377 | MI0000785 | 15 | chr14 | 101062050 | 101062118 | + | ✓ |
| hsa-mir-376c | MI0000776 | 214 | chr14 | 101039690 | 101039755 | + | ✓ |
| hsa-mir-376b | MI0002466 | 115 | chr14 | 101040436 | 101040535 | + | ✓ |
| hsa-mir-376a-2 | MI0003529 | 119 | chr14 | 101040069 | 101040148 | + | ✓ |
| hsa-mir-376a-1 | MI0000784 | 120 | chr14 | 101040782 | 101040849 | + | ✓ |
| hsa-mir-375 | MI0000783 | 3418 | chr2 | 219001645 | 219001708 | − | ✓ |
| hsa-mir-374c | MI0016684 | 8 | chrX | 74218549 | 74218618 | + | — |

TABLE 2-continued

| miRNA ID | Accession | RPM | Chromosome | Start | End | Strand | Confidence |
|---|---|---|---|---|---|---|---|
| hsa-mir-374b | MI0005566 | 1108 | chrX | 74218547 | 74218618 | − | ✓ |
| hsa-mir-374a | MI0000782 | 1271 | chrX | 74287286 | 74287357 | − | ✓ |
| hsa-mir-373 | MI0000781 | 2 | chr19 | 53788705 | 53788773 | + | − |
| hsa-mir-372 | MI0000780 | 91 | chr19 | 53787890 | 53787956 | + | − |
| hsa-mir-371b | MI0017393 | 23 | chr19 | 53787677 | 53787742 | − | − |
| hsa-mir-371a | MI0000779 | − | chr19 | 53787675 | 53787741 | + | − |
| hsa-mir-3714 | MI0016135 | 5 | chr3 | 16933196 | 16933260 | + | − |
| hsa-mir-3713 | MI0016134 | − | | | | | − |
| hsa-mir-370 | MI0000778 | 9 | chr14 | 100911139 | 100911213 | + | ✓ |
| hsa-mir-3692 | MI0016093 | − | chr6 | 157529132 | 157529200 | + | − |
| hsa-mir-3691 | MI0016092 | − | chr6 | 5148233 | 5148322 | − | − |
| hsa-mir-3690-2 | MI0023561 | − | chrY | 1293918 | 1293992 | + | − |
| hsa-mir-3690-1 | MI0016091 | − | chrX | 1293918 | 1293992 | + | − |
| hsa-mir-369 | MI0000777 | 53 | chr14 | 101065598 | 101065667 | + | ✓ |
| hsa-mir-3689f | MI0016837 | 25 | chr9 | 134850742 | 134850807 | − | − |
| hsa-mir-3689e | MI0016836 | − | chr9 | 134850570 | 134850641 | − | − |
| hsa-mir-3689d-2 | MI0016835 | − | chr9 | 134850277 | 134850356 | − | − |
| hsa-mir-3689d-1 | MI0016834 | − | chr9 | 134849609 | 134849682 | − | − |
| hsa-mir-3689c | MI0016832 | − | chr9 | 134849298 | 134849369 | − | − |
| hsa-mir-3689b | MI0016411 | − | chr9 | 134850125 | 134850272 | − | − |
| hsa-mir-3689a | MI0016090 | − | chr9 | 134849487 | 134849564 | − | − |
| hsa-mir-3688-2 | MI0017447 | 3 | chr4 | 159128805 | 159128891 | + | − |
| hsa-mir-3688-1 | MI0016089 | 73 | chr4 | 159128802 | 159128894 | − | − |
| hsa-mir-3686 | MI0016087 | − | chr8 | 129484057 | 129484142 | − | − |
| hsa-mir-3685 | MI0016086 | − | chr12 | 95309923 | 95309984 | + | − |
| hsa-mir-3684 | MI0016085 | − | chr4 | 98997387 | 98997460 | + | − |
| hsa-mir-3683 | MI0016084 | − | chr7 | 7066964 | 7067045 | − | − |
| hsa-mir-3682 | MI0016083 | 4 | chr2 | 53849122 | 53849205 | − | − |
| hsa-mir-3681 | MI0016082 | − | chr2 | 12199130 | 12199201 | + | − |
| hsa-mir-3680-2 | MI0019113 | 3 | chr16 | 29599179 | 29599265 | − | − |
| hsa-mir-3680-1 | MI0016081 | 3 | chr16 | 21506049 | 21506135 | − | − |
| hsa-mir-3679 | MI0016080 | − | chr2 | 134127125 | 134127192 | + | − |
| hsa-mir-3678 | MI0016079 | 10 | chr17 | 75406069 | 75406162 | + | − |
| hsa-mir-3677 | MI0016078 | 8 | chr16 | 2270713 | 2270772 | + | ✓ |
| hsa-mir-3675 | MI0016076 | − | chr1 | 16858949 | 16859021 | − | − |
| hsa-mir-3674 | MI0016075 | − | chr8 | 1801125 | 1801192 | + | − |
| hsa-mir-3672 | MI0016073 | − | chrX | 121370972 | 121371053 | + | − |
| hsa-mir-3671 | MI0016072 | − | chr1 | 65057755 | 65057842 | − | − |
| hsa-mir-3670-4 | MI0031514 | − | chr16 | 18488301 | 18488365 | − | − |

TABLE 2-continued

| miRNA ID | Accession | RPM | Chromosome | Start | End | Strand | Confidence |
|---|---|---|---|---|---|---|---|
| hsa-mir-3670-3 | MI0031513 | — | chr16 | 18405698 | 18405762 | − | — |
| hsa-mir-3670-2 | MI0019112 | — | chr16 | 16306370 | 16306434 | + | — |
| hsa-mir-3670-1 | MI0016071 | — | chr16 | 14907717 | 14907781 | + | — |
| hsa-mir-367 | MI0000775 | 9 | chr4 | 112647874 | 112647941 | − | — |
| hsa-mir-3668 | MI0016069 | — | chr6 | 140205252 | 140205326 | + | — |
| hsa-mir-3667 | MI0016068 | — | chr22 | 49543393 | 49543466 | − | — |
| hsa-mir-3666 | MI0016067 | — | chr7 | 114653345 | 114653455 | + | — |
| hsa-mir-3665 | MI0016066 | 63 | chr13 | 77698012 | 77698116 | − | — |
| hsa-mir-3664 | MI0016065 | — | chr11 | 70872270 | 70872368 | − | — |
| hsa-mir-3663 | MI0016064 | 38 | chr10 | 117167678 | 117167774 | − | — |
| hsa-mir-3662 | MI0016063 | — | chr6 | 134979338 | 134979432 | − | — |
| hsa-mir-3661 | MI0016062 | 5 | chr5 | 134225757 | 134225852 | + | — |
| hsa-mir-3660 | MI0016061 | 29 | chr5 | 90016621 | 90016720 | − | — |
| hsa-mir-365b | MI0000769 | 1025 | chr17 | 31575411 | 31575521 | + | ✓ |
| hsa-mir-365a | MI0000767 | 1023 | chr16 | 14309285 | 14309371 | + | ✓ |
| hsa-mir-3659 | MI0016060 | — | chr1 | 38089231 | 38089329 | + | — |
| hsa-mir-3658 | MI0016058 | 3 | chr1 | 165907921 | 165907976 | + | — |
| hsa-mir-3657 | MI0016057 | — | chr12 | 112037599 | 112037715 | − | ✓ |
| hsa-mir-3655 | MI0016055 | — | chr5 | 140647844 | 140647926 | + | — |
| hsa-mir-3654 | MI0016054 | — | chr7 | 133034860 | 133034915 | − | — |
| hsa-mir-3652 | MI0016052 | 5 | chr12 | 103930425 | 103930555 | + | — |
| hsa-mir-3651 | MI0016051 | 3 | chr9 | 92292458 | 92292547 | − | — |
| hsa-mir-3650 | MI0016050 | — | chr5 | 38557502 | 38557561 | − | — |
| hsa-mir-3649 | MI0016049 | 28 | chr12 | 1660315 | 1660380 | − | — |
| hsa-mir-3648-2 | MI0031512 | 8 | chr21 | 8986999 | 8987178 | + | — |
| hsa-mir-3648-1 | MI0016048 | 8 | chr21 | 8208473 | 8208652 | + | — |
| hsa-mir-3646 | MI0016046 | 18 | chr20 | 44408120 | 44408203 | + | — |
| hsa-mir-363 | MI0000764 | 757 | chrX | 134169378 | 134169452 | − | ✓ |
| hsa-mir-3622b | MI0016014 | 6 | chr8 | 27701673 | 27701767 | − | — |
| hsa-mir-3622a | MI0016013 | 5 | chr8 | 27701677 | 27701759 | + | — |
| hsa-mir-3621 | MI0016012 | — | chr9 | 137169186 | 137169270 | − | — |
| hsa-mir-3620 | MI0016011 | — | chr1 | 228097263 | 228097341 | + | — |
| hsa-mir-362 | MI0000762 | 61 | chrX | 50008964 | 50009028 | + | ✓ |
| hsa-mir-3619 | MI0016009 | 2 | chr22 | 46091044 | 46091126 | + | — |
| hsa-mir-3618 | MI0016008 | 8 | chr22 | 20085746 | 20085833 | + | — |
| hsa-mir-3617 | MI0016007 | — | chr20 | 45705102 | 45705180 | − | — |
| hsa-mir-3616 | MI0016006 | 2 | chr20 | 47166967 | 47167058 | + | ✓ |
| hsa-mir-3615 | MI0016005 | 11 | chr17 | 74748613 | 74748699 | + | — |
| hsa-mir-3614 | MI0016004 | 19 | chr17 | 56891270 | 56891355 | − | ✓ |

TABLE 2-continued

| miRNA ID | Accession | RPM | Chromosome | Start | End | Strand | Confidence |
|---|---|---|---|---|---|---|---|
| hsa-mir-3613 | MI0016003 | 321 | chr13 | 49996415 | 49996501 | − | ✓ |
| hsa-mir-3612 | MI0016002 | — | chr12 | 128294092 | 128294178 | + | — |
| hsa-mir-3611 | MI0016001 | 4 | chr10 | 35079598 | 35079680 | − | ✓ |
| hsa-mir-3610 | MI0016000 | 13 | chr8 | 116874728 | 116874800 | − | — |
| hsa-mir-361 | MI0000760 | 866 | chrX | 85903636 | 85903707 | − | ✓ |
| hsa-mir-3609 | MI0015999 | 73 | chr7 | 98881650 | 98881729 | + | — |
| hsa-mir-3606 | MI0015996 | 9 | chr2 | 188995630 | 188995692 | + | — |
| hsa-mir-3605 | MI0015995 | 1 | chr1 | 33332393 | 33332492 | − | — |
| hsa-mir-3529 | MI0017351 | — | chr15 | 88611847 | 88611924 | − | — |
| hsa-mir-34c | MI0000743 | 379 | chr11 | 111513439 | 111513515 | + | ✓ |
| hsa-mir-34b | MI0000742 | 43 | chr11 | 111512938 | 111513021 | + | ✓ |
| hsa-mir-34a | MI0000268 | 269 | chr1 | 9151668 | 9151777 | − | ✓ |
| hsa-mir-346 | MI0000826 | 3 | chr10 | 86264694 | 86264788 | − | — |
| hsa-mir-345 | MI0000825 | 123 | chr14 | 100307859 | 100307956 | + | ✓ |
| hsa-mir-342 | MI0000805 | 776 | chr14 | 100109655 | 100109753 | + | ✓ |
| hsa-mir-340 | MI0000802 | 913 | chr5 | 180015303 | 180015397 | − | ✓ |
| hsa-mir-33b | MI0003646 | 27 | chr17 | 17813836 | 17813931 | − | ✓ |
| hsa-mir-33a | MI0000091 | 256 | chr22 | 41900944 | 41901012 | + | ✓ |
| hsa-mir-339 | MI0000815 | 238 | chr7 | 1022933 | 1023026 | − | ✓ |
| hsa-mir-338 | MI0000814 | 97 | chr17 | 81125883 | 81125949 | − | ✓ |
| hsa-mir-337 | MI0000806 | 21 | chr14 | 100874493 | 100874585 | + | ✓ |
| hsa-mir-335 | MI0000816 | 3777 | chr7 | 130496111 | 130496204 | + | ✓ |
| hsa-mir-331 | MI0000812 | 226 | chr12 | 95308420 | 95308513 | + | — |
| hsa-mir-330 | MI0000803 | 70 | chr19 | 45638994 | 45639087 | − | ✓ |
| hsa-mir-329-2 | MI0001726 | — | chr14 | 101027100 | 101027183 | + | ✓ |
| hsa-mir-329-1 | MI0001725 | — | chr14 | 101026785 | 101026864 | + | ✓ |
| hsa-mir-328 | MI0000804 | 31 | chr16 | 67202321 | 67202395 | − | — |
| hsa-mir-326 | MI0000808 | 14 | chr11 | 75335092 | 75335186 | − | — |
| hsa-mir-325 | MI0000824 | — | chrX | 77005404 | 77005501 | − | — |
| hsa-mir-324 | MI0000813 | 210 | chr17 | 7223297 | 7223379 | − | ✓ |
| hsa-mir-323b | MI0014206 | — | chr14 | 101056219 | 101056300 | + | — |
| hsa-mir-323a | MI0000807 | 1 | chr14 | 101025732 | 101025817 | + | ✓ |
| hsa-mir-320e | MI0014234 | 4717 | chr19 | 46709282 | 46709354 | − | — |
| hsa-mir-320d-2 | MI0008192 | 2985 | chrX | 140926160 | 140926231 | − | — |
| hsa-mir-320d-1 | MI0008190 | 4526 | chr13 | 40727816 | 40727887 | − | — |
| hsa-mir-320c-2 | MI0008191 | 4285 | chr18 | 24321675 | 24321746 | + | — |
| hsa-mir-320c-1 | MI0003778 | 3570 | chr18 | 21683518 | 21683589 | + | — |
| hsa-mir-320b-2 | MI0003839 | 5249 | chr1 | 224257040 | 224257110 | − | — |
| hsa-mir-320b-1 | MI0003776 | 5177 | chr1 | 116671746 | 116671817 | + | — |

TABLE 2-continued

| miRNA ID | Accession | RPM | Chromosome | Start | End | Strand | Confidence |
|---|---|---|---|---|---|---|---|
| hsa-mir-320a | MI0000542 | 5331 | chr8 | 22244966 | 22245037 | − | ✓ |
| hsa-mir-3202-2 | MI0014253 | 3 | chrX | 153981098 | 153981176 | − | — |
| hsa-mir-3202-1 | MI0014252 | 1 | chrX | 153981097 | 153981177 | + | — |
| hsa-mir-3201 | MI0014250 | — | chr22 | 48274364 | 48274415 | + | — |
| hsa-mir-3200 | MI0014249 | 3 | chr22 | 30731557 | 30731641 | + | ✓ |
| hsa-mir-32 | MI0000090 | 222 | chr9 | 109046229 | 109046298 | − | ✓ |
| hsa-mir-3199-2 | MI0014248 | — | chr22 | 27920526 | 27920611 | + | — |
| hsa-mir-3199-1 | MI0014247 | — | chr22 | 27920525 | 27920612 | − | — |
| hsa-mir-3198-2 | MI0017335 | — | chr12 | 54231397 | 54231476 | − | — |
| hsa-mir-3198-1 | MI0014246 | — | chr22 | 17764180 | 17764259 | − | — |
| hsa-mir-3197 | MI0014245 | — | chr21 | 41167557 | 41167629 | + | — |
| hsa-mir-3196 | MI0014241 | 12 | chr20 | 63238779 | 63238842 | + | — |
| hsa-mir-3195 | MI0014240 | 27 | chr20 | 62064802 | 62064885 | + | — |
| hsa-mir-3194 | MI0014239 | — | chr20 | 51452905 | 51452977 | − | — |
| hsa-mir-3193 | MI0014238 | — | chr20 | 31607186 | 31607240 | + | — |
| hsa-mir-3192 | MI0014237 | 457 | chr20 | 18470615 | 18470691 | + | — |
| hsa-mir-3191 | MI0014236 | — | chr19 | 47226944 | 47227019 | − | — |
| hsa-mir-3190 | MI0014235 | 12 | chr19 | 47226942 | 47227021 | + | — |
| hsa-mir-3189 | MI0014233 | 2 | chr19 | 18386562 | 18386634 | + | — |
| hsa-mir-3188 | MI0014232 | 1 | chr19 | 18282077 | 18282161 | + | — |
| hsa-mir-3187 | MI0014231 | 2 | chr19 | 813584 | 813653 | + | — |
| hsa-mir-3186 | MI0014229 | — | chr17 | 81451104 | 81451188 | − | — |
| hsa-mir-3185 | MI0014227 | 6 | chr17 | 48724408 | 48724475 | − | — |
| hsa-mir-3184 | MI0014226 | — | chr17 | 30117086 | 30117160 | − | — |
| hsa-mir-3183 | MI0014225 | — | chr17 | 1022476 | 1022559 | − | — |
| hsa-mir-3182 | MI0014224 | 37 | chr16 | 83508346 | 83508408 | + | — |
| hsa-mir-3181 | MI0014223 | 10 | chr16 | 50742305 | 50742377 | + | — |
| hsa-mir-3180-5 | MI0016409 | 15 | chr16 | 2135977 | 2136129 | − | — |
| hsa-mir-3180-4 | MI0016408 | 14 | chr16 | 15154850 | 15155002 | − | — |
| hsa-mir-3180-3 | MI0014217 | 13 | chr16 | 18402178 | 18402271 | − | ✓ |
| hsa-mir-3180-2 | MI0014215 | 13 | chr16 | 16309879 | 16309966 | + | ✓ |
| hsa-mir-3180-1 | MI0014214 | 13 | chr16 | 14911220 | 14911313 | + | ✓ |
| hsa-mir-3179-4 | MI0031510 | — | chr16 | 18494493 | 18494576 | − | — |
| hsa-mir-3179-3 | MI0014221 | — | chr16 | 18411894 | 18411977 | − | — |
| hsa-mir-3179-2 | MI0014216 | — | chr16 | 16300159 | 16300242 | + | — |
| hsa-mir-3179-1 | MI0014213 | — | chr16 | 14901508 | 14901591 | + | — |
| hsa-mir-3178 | MI0014212 | 37 | chr16 | 2531922 | 2532005 | − | — |
| hsa-mir-3177 | MI0014211 | — | chr16 | 1734985 | 1735066 | + | — |
| hsa-mir-3176 | MI0014210 | 51 | chr16 | 543277 | 543366 | + | — |

TABLE 2-continued

| miRNA ID | Accession | RPM | Chromosome | Start | End | Strand | Confidence |
|----------|-----------|-----|------------|-------|-----|--------|------------|
| hsa-mir-3175 | MI0014209 | 1 | chr15 | 92904399 | 92904475 | + | — |
| hsa-mir-3174 | MI0014208 | — | chr15 | 90006755 | 90006841 | + | — |
| hsa-mir-3173 | MI0014204 | 7 | chr14 | 95137919 | 95137986 | − | ✓ |
| hsa-mir-3171 | MI0014202 | — | chr14 | 27633205 | 27633278 | − | ✓ |
| hsa-mir-3170 | MI0014201 | — | chr13 | 98208524 | 98208600 | + | — |
| hsa-mir-3169 | MI0014200 | — | chr13 | 61199798 | 61199880 | − | — |
| hsa-mir-3168 | MI0014199 | 98 | chr13 | 41101019 | 41101100 | − | — |
| hsa-mir-3167 | MI0014198 | — | chr11 | 126988458 | 126988542 | − | — |
| hsa-mir-3166 | MI0014196 | — | chr11 | 88176502 | 88176593 | + | — |
| hsa-mir-3165 | MI0014195 | 1 | chr11 | 72072228 | 72072302 | − | — |
| hsa-mir-3164 | MI0014194 | — | chr11 | 69083176 | 69083258 | + | — |
| hsa-mir-3163 | MI0014193 | 4 | chr11 | 66934434 | 66934506 | − | — |
| hsa-mir-3162 | MI0014192 | 1 | chr11 | 59595077 | 59595158 | − | — |
| hsa-mir-3161 | MI0014191 | — | chr11 | 48096782 | 48096858 | + | — |
| hsa-mir-3160-2 | MI0014190 | 1 | chr11 | 46451807 | 46451887 | + | — |
| hsa-mir-3160-1 | MI0014189 | — | chr11 | 46451805 | 46451889 | − | — |
| hsa-mir-3159 | MI0014188 | 638 | chr11 | 18387787 | 18387860 | + | — |
| hsa-mir-3158-2 | MI0014187 | 2 | chr10 | 101601417 | 101601497 | − | ✓ |
| hsa-mir-3158-1 | MI0014186 | 2 | chr10 | 101601417 | 101601497 | + | ✓ |
| hsa-mir-3157 | MI0014185 | — | chr10 | 96064315 | 96064399 | − | ✓ |
| hsa-mir-3156-3 | MI0014242 | — | chr21 | 13406384 | 13406460 | − | — |
| hsa-mir-3156-2 | MI0014230 | — | chr18 | 14830166 | 14830242 | + | — |
| hsa-mir-3156-1 | MI0014184 | — | chr10 | 45164014 | 45164088 | + | — |
| hsa-mir-3155b | MI0016839 | 22 | chr10 | 6152207 | 6152262 | − | — |
| hsa-mir-3155a | MI0014183 | 2 | chr10 | 6152196 | 6152277 | + | ✓ |
| hsa-mir-3154 | MI0014182 | 1 | chr9 | 128244947 | 128245030 | − | — |
| hsa-mir-3153 | MI0014180 | — | chr9 | 89312225 | 89312306 | + | — |
| hsa-mir-3152 | MI0014179 | 19 | chr9 | 18573306 | 18573379 | + | — |
| hsa-mir-3151 | MI0014178 | — | chr8 | 103154614 | 103154689 | + | — |
| hsa-mir-3150b | MI0016426 | 5 | chr8 | 95072911 | 95072996 | − | — |
| hsa-mir-3150a | MI0014177 | 24 | chr8 | 95072914 | 95072993 | + | — |
| hsa-mir-3149 | MI0014176 | 130 | chr8 | 76966768 | 76966850 | − | — |
| hsa-mir-3148 | MI0014175 | — | chr8 | 29957272 | 29957348 | − | — |
| hsa-mir-3147 | MI0014173 | — | chr7 | 57405025 | 57405090 | + | — |
| hsa-mir-3146 | MI0014172 | — | chr7 | 19705358 | 19705436 | − | — |
| hsa-mir-3145 | MI0014170 | — | chr6 | 138435213 | 138435294 | − | — |
| hsa-mir-3144 | MI0014169 | 3 | chr6 | 120015179 | 120015257 | + | ✓ |
| hsa-mir-3143 | MI0014167 | 172 | chr6 | 27147626 | 27147688 | + | — |
| hsa-mir-3142 | MI0014166 | — | chr5 | 160474402 | 160474483 | + | — |

TABLE 2-continued

| miRNA ID | Accession | RPM | Chromosome | Start | End | Strand | Confidence |
|---|---|---|---|---|---|---|---|
| hsa-mir-3141 | MI0014165 | 1 | chr5 | 154596012 | 154596072 | – | – |
| hsa-mir-3140 | MI0014163 | – | chr4 | 152489327 | 152489416 | – | ✓ |
| hsa-mir-3139 | MI0014162 | 48 | chr4 | 143343460 | 143343535 | + | – |
| hsa-mir-3138 | MI0014161 | 1 | chr4 | 10078611 | 10078692 | – | – |
| hsa-mir-3137 | MI0014160 | 28 | chr3 | 195134506 | 195134580 | – | – |
| hsa-mir-3136 | MI0014158 | – | chr3 | 69048958 | 69049035 | – | – |
| hsa-mir-3135b | MI0016809 | 71 | chr6 | 32749912 | 32749979 | – | – |
| hsa-mir-3135a | MI0014156 | 367 | chr3 | 20137565 | 20137641 | + | – |
| hsa-mir-3134 | MI0014155 | 14 | chr3 | 15697298 | 15697371 | – | – |
| hsa-mir-3133 | MI0014153 | – | chr2 | 241477905 | 241477982 | + | – |
| hsa-mir-3132 | MI0014152 | – | chr2 | 219549073 | 219549147 | – | – |
| hsa-mir-3131 | MI0014151 | – | chr2 | 219058688 | 219058750 | – | – |
| hsa-mir-3130-2 | MI0014148 | 3 | chr2 | 206783234 | 206783308 | + | ✓ |
| hsa-mir-3130-1 | MI0014147 | 3 | chr2 | 206783234 | 206783308 | – | ✓ |
| hsa-mir-3129 | MI0014146 | – | chr2 | 189133036 | 189133111 | – | – |
| hsa-mir-3128 | MI0014145 | – | chr2 | 177255945 | 177256010 | – | – |
| hsa-mir-3127 | MI0014144 | – | chr2 | 96798278 | 96798353 | + | – |
| hsa-mir-3126 | MI0014143 | – | chr2 | 69103682 | 69103755 | + | ✓ |
| hsa-mir-3125 | MI0014142 | 9 | chr2 | 12737367 | 12737444 | + | – |
| hsa-mir-3124 | MI0014140 | – | chr1 | 248826377 | 248826443 | + | – |
| hsa-mir-3123 | MI0014139 | 46 | chr1 | 241132272 | 241132346 | + | – |
| hsa-mir-3122 | MI0014138 | – | chr1 | 212077613 | 212077685 | + | – |
| hsa-mir-3121 | MI0014137 | – | chr1 | 180438314 | 180438390 | – | – |
| hsa-mir-3120 | MI0014136 | – | chr1 | 172138808 | 172138888 | + | – |
| hsa-mir-3119-2 | MI0014135 | – | chr1 | 170151378 | 170151462 | + | – |
| hsa-mir-3119-1 | MI0014134 | – | chr1 | 170151378 | 170151462 | – | – |
| hsa-mir-3118-4 | MI0014207 | – | chr15 | 21843750 | 21843824 | + | – |
| hsa-mir-3118-3 | MI0014133 | – | chr15 | 21406385 | 21406459 | + | – |
| hsa-mir-3118-2 | MI0014132 | – | chr15 | 20832795 | 20832869 | + | – |
| hsa-mir-3118-1 | MI0014131 | – | chr21 | 13644775 | 13644850 | – | – |
| hsa-mir-3117 | MI0014130 | – | chr1 | 66628440 | 66628517 | + | – |
| hsa-mir-3116-2 | MI0014129 | – | chr1 | 62078789 | 62078856 | – | – |
| hsa-mir-3116-1 | MI0014128 | – | chr1 | 62078786 | 62078859 | + | – |
| hsa-mir-3115 | MI0014127 | 29 | chr1 | 23044305 | 23044372 | + | – |
| hsa-mir-31 | MI0000089 | 1263 | chr9 | 21512115 | 21512185 | – | ✓ |
| hsa-mir-30e | MI0000749 | 10738 | chr1 | 40754355 | 40754446 | + | ✓ |
| hsa-mir-30d | MI0000255 | 11691 | chr8 | 134804876 | 134804945 | – | ✓ |
| hsa-mir-30c-2 | MI0000254 | 3223 | chr6 | 71376960 | 71377031 | – | ✓ |
| hsa-mir-30c-1 | MI0000736 | 3205 | chr1 | 40757284 | 40757372 | + | ✓ |

TABLE 2-continued

| miRNA ID | Accession | RPM | Chromosome | Start | End | Strand | Confidence |
|----------|-----------|-----|------------|-------|-----|--------|------------|
| hsa-mir-30b | MI0000441 | 2245 | chr8 | 134800520 | 134800607 | – | ✓ |
| hsa-mir-30a | MI0000088 | 15057 | chr6 | 71403551 | 71403621 | – | ✓ |
| hsa-mir-3085 | MI0039500 | – | chr10 | 97875813 | 97875897 | – | – |
| hsa-mir-3074 | MI0014181 | 4 | chr9 | 95086014 | 95086094 | – | – |
| hsa-mir-3065 | MI0014228 | 39 | chr17 | 81125877 | 81125955 | + | ✓ |
| hsa-mir-3064 | MI0017375 | – | chr17 | 64500774 | 64500839 | – | – |
| hsa-mir-3059 | MI0039499 | 8 | chr12 | 86745068 | 86745149 | – | ✓ |
| hsa-mir-302f | MI0006418 | – | chr18 | 30298910 | 30298960 | + | – |
| hsa-mir-302e | MI0006417 | – | chr11 | 7234766 | 7234837 | + | – |
| hsa-mir-302d | MI0000774 | 10 | chr4 | 112648004 | 112648071 | – | – |
| hsa-mir-302c | MI0000773 | – | chr4 | 112648363 | 112648430 | – | – |
| hsa-mir-302b | MI0000772 | – | chr4 | 112648485 | 112648557 | – | – |
| hsa-mir-302a | MI0000738 | 42 | chr4 | 112648183 | 112648251 | – | ✓ |
| hsa-mir-301b | MI0005568 | 140 | chr22 | 21652981 | 21653058 | + | ✓ |
| hsa-mir-301a | MI0000745 | 227 | chr17 | 59151136 | 59151221 | – | ✓ |
| hsa-mir-300 | MI0005525 | – | chr14 | 101041363 | 101041445 | + | – |
| hsa-mir-29c | MI0000735 | 11179 | chr1 | 207801852 | 207801939 | – | ✓ |
| hsa-mir-29b-2 | MI0000107 | 8561 | chr1 | 207802443 | 207802523 | – | ✓ |
| hsa-mir-29b-1 | MI0000105 | 8558 | chr7 | 130877459 | 130877539 | – | ✓ |
| hsa-mir-29a | MI0000087 | 11796 | chr7 | 130876747 | 130876810 | – | ✓ |
| hsa-mir-299 | MI0000744 | 14 | chr14 | 101023794 | 101023856 | + | ✓ |
| hsa-mir-298 | MI0005523 | – | chr20 | 58818226 | 58818313 | – | – |
| hsa-mir-297 | MI0005775 | 3 | chr4 | 110860582 | 110860647 | – | – |
| hsa-mir-296 | MI0000747 | 12 | chr20 | 58817615 | 58817694 | – | ✓ |
| hsa-mir-2909 | MI0013083 | – | chr17 | 37033745 | 37033813 | + | – |
| hsa-mir-2861 | MI0013006 | 9 | chr9 | 127785918 | 127786007 | + | – |
| hsa-mir-28 | MI0000086 | 3607 | chr3 | 188688781 | 188688866 | + | ✓ |
| hsa-mir-27b | MI0000440 | 14864 | chr9 | 95085445 | 95085541 | + | ✓ |
| hsa-mir-27a | MI0000085 | 8588 | chr19 | 13836440 | 13836517 | – | ✓ |
| hsa-mir-26b | MI0000084 | 17403 | chr2 | 218402646 | 218402722 | + | ✓ |
| hsa-mir-26a-2 | MI0000750 | 36460 | chr12 | 57824609 | 57824692 | – | ✓ |
| hsa-mir-26a-1 | MI0000083 | 26870 | chr3 | 37969404 | 37969480 | + | ✓ |
| hsa-mir-2682 | MI0012063 | – | chr1 | 98045242 | 98045351 | – | – |
| hsa-mir-2681 | MI0012062 | – | chr13 | 101967642 | 101967746 | – | – |
| hsa-mir-25 | MI0000082 | 3122 | chr7 | 100093560 | 100093643 | – | ✓ |
| hsa-mir-2467 | MI0017432 | – | chr2 | 239351724 | 239351804 | – | ✓ |
| hsa-mir-24-2 | MI0000081 | 3749 | chr19 | 13836287 | 13836359 | – | ✓ |
| hsa-mir-24-1 | MI0000080 | 3719 | chr9 | 95086021 | 95086088 | + | ✓ |
| hsa-mir-23c | MI0016010 | 5962 | chrX | 20017088 | 20017187 | – | – |

TABLE 2-continued

| miRNA ID | Accession | RPM | Chromosome | Start | End | Strand | Confidence |
|---|---|---|---|---|---|---|---|
| hsa-mir-23b | MI0000439 | 11091 | chr9 | 95085208 | 95085304 | + | — |
| hsa-mir-23a | MI0000079 | 10137 | chr19 | 13836587 | 13836659 | − | ✓ |
| hsa-mir-2392 | MI0016870 | — | chr14 | 100814491 | 100814574 | + | — |
| hsa-mir-2355 | MI0015873 | 10 | chr2 | 207109987 | 207110073 | − | — |
| hsa-mir-2278 | MI0011285 | 3 | chr9 | 94809962 | 94810057 | + | — |
| hsa-mir-2277 | MI0011284 | — | chr5 | 93620696 | 93620788 | − | ✓ |
| hsa-mir-2276 | MI0011282 | — | chr13 | 24162416 | 24162504 | + | ✓ |
| hsa-mir-224 | MI0000301 | 237 | chrX | 151958578 | 151958658 | − | ✓ |
| hsa-mir-223 | MI0000300 | 1044 | chrX | 66018870 | 66018979 | + | ✓ |
| hsa-mir-222 | MI0000299 | 3517 | chrX | 45747015 | 45747124 | − | ✓ |
| hsa-mir-221 | MI0000298 | 4317 | chrX | 45746157 | 45746266 | − | ✓ |
| hsa-mir-22 | MI0000078 | 3830 | chr17 | 1713903 | 1713987 | − | ✓ |
| hsa-mir-219b | MI0017299 | — | chr9 | 128392621 | 128392708 | + | ✓ |
| hsa-mir-219a-2 | MI0000740 | 141 | chr9 | 128392618 | 128392714 | − | ✓ |
| hsa-mir-219a-1 | MI0000296 | — | chr6 | 33207835 | 33207944 | + | ✓ |
| hsa-mir-218-2 | MI0000295 | 1077 | chr5 | 168768146 | 168768255 | − | ✓ |
| hsa-mir-218-1 | MI0000294 | 1151 | chr4 | 20528275 | 20528384 | + | ✓ |
| hsa-mir-217 | MI0000293 | 120 | chr2 | 55982967 | 55983076 | − | — |
| hsa-mir-216b | MI0005569 | 5 | chr2 | 56000714 | 56000795 | − | — |
| hsa-mir-216a | MI0000292 | 413 | chr2 | 55988950 | 55989059 | − | ✓ |
| hsa-mir-215 | MI0000291 | 686 | chr1 | 220117853 | 220117962 | − | — |
| hsa-mir-214 | MI0000290 | 459 | chr1 | 172138798 | 172138907 | − | ✓ |
| hsa-mir-212 | MI0000288 | 28 | chr17 | 2050271 | 2050380 | − | ✓ |
| hsa-mir-2117 | MI0010636 | — | chr17 | 43444806 | 43444885 | + | — |
| hsa-mir-2116 | MI0010635 | — | chr15 | 59171183 | 59171262 | − | ✓ |
| hsa-mir-2115 | MI0010634 | 1 | chr3 | 48316360 | 48316459 | − | ✓ |
| hsa-mir-2114 | MI0010633 | — | chrX | 150228004 | 150228083 | + | ✓ |
| hsa-mir-2113 | MI0003939 | 8 | chr6 | 98024531 | 98024621 | + | — |
| hsa-mir-2110 | MI0010629 | 11 | chr10 | 114174105 | 114174179 | − | ✓ |
| hsa-mir-211 | MI0000287 | 500 | chr15 | 31065032 | 31065141 | − | ✓ |
| hsa-mir-210 | MI0000286 | 160 | chr11 | 568089 | 568198 | − | ✓ |
| hsa-mir-21 | MI0000077 | 99440 | chr17 | 59841266 | 59841337 | + | ✓ |
| hsa-mir-20b | MI0001519 | 544 | chrX | 134169809 | 134169877 | − | ✓ |
| hsa-mir-20a | MI0000076 | 7477 | chr13 | 91351065 | 91351135 | + | ✓ |
| hsa-mir-208b | MI0005570 | 49 | chr14 | 23417987 | 23418063 | − | ✓ |
| hsa-mir-208a | MI0000251 | 90 | chr14 | 23388596 | 23388666 | − | ✓ |
| hsa-mir-206 | MI0000490 | 375 | chr6 | 52144349 | 52144434 | + | — |
| hsa-mir-2054 | MI0010488 | — | chr4 | 125507259 | 125507307 | + | — |
| hsa-mir-2053 | MI0010487 | — | chr8 | 112643493 | 112643583 | + | — |

TABLE 2-continued

| miRNA ID | Accession | RPM | Chromosome | Start | End | Strand | Confidence |
|---|---|---|---|---|---|---|---|
| hsa-mir-2052 | MI0010486 | — | chr8 | 74705693 | 74705747 | + | — |
| hsa-mir-205 | MI0000285 | 6213 | chr1 | 209432133 | 209432242 | + | ✓ |
| hsa-mir-204 | MI0000284 | 400 | chr9 | 70809975 | 70810084 | − | ✓ |
| hsa-mir-203b | MI0017343 | — | chr14 | 104117418 | 104117503 | − | — |
| hsa-mir-203a | MI0000283 | 524 | chr14 | 104117405 | 104117514 | + | ✓ |
| hsa-mir-202 | MI0003130 | 190 | chr10 | 133247511 | 133247620 | − | ✓ |
| hsa-mir-200c | MI0000650 | 4878 | chr12 | 6963699 | 6963766 | + | ✓ |
| hsa-mir-200b | MI0000342 | 3832 | chr1 | 1167104 | 1167198 | + | ✓ |
| hsa-mir-200a | MI0000737 | 2312 | chr1 | 1167863 | 1167952 | + | ✓ |
| hsa-mir-19b-2 | MI0000075 | 11771 | chrX | 134169671 | 134169766 | − | ✓ |
| hsa-mir-19b-1 | MI0000074 | 11311 | chr13 | 91351192 | 91351278 | + | ✓ |
| hsa-mir-19a | MI0000073 | 10618 | chr13 | 91350891 | 91350972 | + | ✓ |
| hsa-mir-199b | MI0000282 | 9394 | chr9 | 128244721 | 128244830 | − | ✓ |
| hsa-mir-199a-2 | MI0000281 | 10237 | chr1 | 172144535 | 172144644 | − | ✓ |
| hsa-mir-199a-1 | MI0000242 | 10013 | chr19 | 10817426 | 10817496 | − | ✓ |
| hsa-mir-198 | MI0000240 | 7 | chr3 | 120395668 | 120395729 | − | — |
| hsa-mir-1976 | MI0009986 | 1 | chr1 | 26554542 | 26554593 | + | — |
| hsa-mir-1973 | MI0009983 | 5 | | | | | — |
| hsa-mir-1972-2 | MI0015977 | 94 | chr16 | 70030346 | 70030422 | + | — |
| hsa-mir-1972-1 | MI0009982 | 94 | chr16 | 15010321 | 15010397 | − | — |
| hsa-mir-197 | MI0000239 | 195 | chr1 | 109598893 | 109598967 | + | ✓ |
| hsa-mir-196b | MI0001150 | 1662 | chr7 | 27169480 | 27169563 | − | ✓ |
| hsa-mir-196a-2 | MI0000279 | 1231 | chr12 | 53991738 | 53991847 | + | ✓ |
| hsa-mir-196a-1 | MI0000238 | 1430 | chr17 | 48632490 | 48632559 | − | ✓ |
| hsa-mir-195 | MI0000489 | 2034 | chr17 | 7017615 | 7017701 | − | ✓ |
| hsa-mir-194-2 | MI0000732 | 155 | chr11 | 64891355 | 64891439 | − | ✓ |
| hsa-mir-194-1 | MI0000488 | 167 | chr1 | 220118157 | 220118241 | − | — |
| hsa-mir-193b | MI0003137 | 657 | chr16 | 14303967 | 14304049 | + | ✓ |
| hsa-mir-193a | MI0000487 | 540 | chr17 | 31559996 | 31560083 | + | ✓ |
| hsa-mir-192 | MI0000234 | 781 | chr11 | 64891137 | 64891246 | − | ✓ |
| hsa-mir-1915 | MI0008336 | 3 | chr10 | 21496562 | 21496641 | − | — |
| hsa-mir-1914 | MI0008335 | — | chr20 | 63941465 | 63941544 | − | — |
| hsa-mir-1913 | MI0008334 | 2 | chr6 | 166509354 | 166509433 | − | — |
| hsa-mir-1912 | MI0008333 | 8 | chrX | 114651544 | 114651623 | + | ✓ |
| hsa-mir-1911 | MI0008332 | — | chrX | 114763184 | 114763263 | + | — |
| hsa-mir-1910 | MI0008331 | 5 | chr16 | 85741621 | 85741700 | − | — |
| hsa-mir-191 | MI0000465 | 8868 | chr3 | 49020618 | 49020709 | − | ✓ |
| hsa-mir-190b | MI0005545 | 8 | chr1 | 154193665 | 154193743 | − | — |
| hsa-mir-190a | MI0000486 | 15 | chr15 | 62823957 | 62824041 | + | ✓ |

TABLE 2-continued

| miRNA ID | Accession | RPM | Chromosome | Start | End | Strand | Confidence |
|---|---|---|---|---|---|---|---|
| hsa-mir-1909 | MI0008330 | 2 | chr19 | 1816159 | 1816238 | – | — |
| hsa-mir-1908 | MI0008329 | 20 | chr11 | 61815161 | 61815240 | – | — |
| hsa-mir-18b | MI0001518 | 2965 | chrX | 134170041 | 134170111 | – | ✓ |
| hsa-mir-18a | MI0000072 | 3057 | chr13 | 91350751 | 91350821 | + | ✓ |
| hsa-mir-188 | MI0000484 | 28 | chrX | 50003503 | 50003588 | + | ✓ |
| hsa-mir-187 | MI0000274 | 111 | chr18 | 35904818 | 35904926 | – | ✓ |
| hsa-mir-186 | MI0000483 | 4207 | chr1 | 71067631 | 71067716 | – | ✓ |
| hsa-mir-185 | MI0000482 | 1871 | chr22 | 20033139 | 20033220 | + | ✓ |
| hsa-mir-1843 | MI0032314 | 7 | chr1 | 175968370 | 175968479 | – | — |
| hsa-mir-184 | MI0000481 | 127 | chr15 | 79209788 | 79209871 | + | ✓ |
| hsa-mir-183 | MI0000273 | 490 | chr7 | 129774905 | 129775014 | – | ✓ |
| hsa-mir-1827 | MI0008195 | 29 | chr12 | 100189884 | 100189949 | + | — |
| hsa-mir-1825 | MI0008193 | — | chr20 | 32237795 | 32237847 | + | — |
| hsa-mir-182 | MI0000272 | 1322 | chr7 | 129770383 | 129770492 | – | ✓ |
| hsa-mir-181d | MI0003139 | 896 | chr19 | 13874875 | 13875011 | + | ✓ |
| hsa-mir-181c | MI0000271 | 180 | chr19 | 13874699 | 13874808 | + | ✓ |
| hsa-mir-181b-2 | MI0000683 | 894 | chr9 | 124693710 | 124693798 | + | ✓ |
| hsa-mir-181b-1 | MI0000270 | 893 | chr1 | 198858873 | 198858982 | – | ✓ |
| hsa-mir-181a-2 | MI0000269 | 3589 | chr9 | 124692442 | 124692551 | + | ✓ |
| hsa-mir-181a-1 | MI0000289 | 3606 | chr1 | 198859044 | 198859153 | – | ✓ |
| hsa-mir-17 | MI0000071 | 9521 | chr13 | 91350605 | 91350688 | + | ✓ |
| hsa-mir-16-2 | MI0000115 | 10438 | chr3 | 160404745 | 160404825 | + | ✓ |
| hsa-mir-16-1 | MI0000070 | 10589 | chr13 | 50048973 | 50049061 | – | ✓ |
| hsa-mir-15b | MI0000438 | 6198 | chr3 | 160404588 | 160404685 | + | ✓ |
| hsa-mir-15a | MI0000069 | 4045 | chr13 | 50049119 | 50049201 | – | ✓ |
| hsa-mir-1587 | MI0016905 | — | chrX | 39837561 | 39837613 | + | — |
| hsa-mir-155 | MI0000681 | 355 | chr21 | 25573980 | 25574044 | + | ✓ |
| hsa-mir-154 | MI0000480 | 2 | chr14 | 101059755 | 101059838 | + | ✓ |
| hsa-mir-1539 | MI0007260 | — | chr18 | 49487373 | 49487422 | + | — |
| hsa-mir-1538 | MI0007259 | — | chr16 | 69565808 | 69565868 | – | — |
| hsa-mir-1537 | MI0007258 | 2 | chr1 | 235853000 | 235853060 | – | — |
| hsa-mir-153-2 | MI0000464 | 75 | chr7 | 157574336 | 157574422 | – | ✓ |
| hsa-mir-153-1 | MI0000463 | 69 | chr2 | 219294111 | 219294200 | – | ✓ |
| hsa-mir-152 | MI0000462 | 2307 | chr17 | 48037161 | 48037247 | – | ✓ |
| hsa-mir-151b | MI0003772 | 2711 | chr14 | 100109419 | 100109514 | – | — |
| hsa-mir-151a | MI0000809 | 4889 | chr8 | 140732564 | 140732653 | – | — |
| hsa-mir-150 | MI0000479 | 699 | chr19 | 49500785 | 49500868 | – | ✓ |
| hsa-mir-149 | MI0000478 | 130 | chr2 | 240456001 | 240456089 | + | ✓ |
| hsa-mir-148b | MI0000811 | 2746 | chr12 | 54337216 | 54337314 | + | ✓ |

TABLE 2-continued

| miRNA ID | Accession | RPM | Chromosome | Start | End | Strand | Confidence |
|---|---|---|---|---|---|---|---|
| hsa-mir-148a | MI0000253 | 15136 | chr7 | 25949919 | 25949986 | − | ✓ |
| hsa-mir-147b | MI0005544 | 32 | chr15 | 45433050 | 45433129 | + | ✓ |
| hsa-mir-147a | MI0000262 | 44 | chr9 | 120244979 | 120245050 | − | — |
| hsa-mir-1471 | MI0007076 | — | chr2 | 231892242 | 231892298 | − | — |
| hsa-mir-1470 | MI0007075 | — | chr19 | 15449548 | 15449608 | + | — |
| hsa-mir-146b | MI0003129 | 2237 | chr10 | 102436512 | 102436584 | + | ✓ |
| hsa-mir-146a | MI0000477 | 2369 | chr5 | 160485352 | 160485450 | + | ✓ |
| hsa-mir-1469 | MI0007074 | 10 | chr15 | 96333261 | 96333307 | + | — |
| hsa-mir-1468 | MI0003782 | — | chrX | 63786002 | 63786087 | − | — |
| hsa-mir-145 | MI0000461 | 29896 | chr5 | 149430646 | 149430733 | + | ✓ |
| hsa-mir-144 | MI0000460 | 640 | chr17 | 28861533 | 28861618 | − | ✓ |
| hsa-mir-143 | MI0000459 | 104879 | chr5 | 149428918 | 149429023 | + | ✓ |
| hsa-mir-142 | MI0000458 | 3620 | chr17 | 58331232 | 58331318 | − | ✓ |
| hsa-mir-141 | MI0000457 | 1700 | chr12 | 6964097 | 6964191 | + | ✓ |
| hsa-mir-140 | MI0000456 | 5403 | chr16 | 69933081 | 69933180 | + | ✓ |
| hsa-mir-139 | MI0000261 | 195 | chr11 | 72615063 | 72615130 | − | ✓ |
| hsa-mir-138-2 | MI0000455 | 159 | chr16 | 56858518 | 56858601 | + | ✓ |
| hsa-mir-138-1 | MI0000476 | 180 | chr3 | 44114212 | 44114310 | + | ✓ |
| hsa-mir-137 | MI0000454 | 246 | chr1 | 98046070 | 98046171 | − | ✓ |
| hsa-mir-136 | MI0000475 | 77 | chr14 | 100884702 | 100884783 | + | ✓ |
| hsa-mir-135b | MI0000810 | 189 | chr1 | 205448302 | 205448398 | − | ✓ |
| hsa-mir-135a-2 | MI0000453 | 444 | chr12 | 97563812 | 97563911 | + | ✓ |
| hsa-mir-135a-1 | MI0000452 | 590 | chr3 | 52294219 | 52294308 | − | ✓ |
| hsa-mir-1343 | MI0017320 | — | chr11 | 34941837 | 34941920 | + | ✓ |
| hsa-mir-134 | MI0000474 | 118 | chr14 | 101054687 | 101054759 | + | ✓ |
| hsa-mir-133b | MI0000822 | 224 | chr6 | 52148923 | 52149041 | + | ✓ |
| hsa-mir-133a-2 | MI0000451 | 543 | chr20 | 62564912 | 62565013 | + | ✓ |
| hsa-mir-133a-1 | MI0000450 | 543 | chr18 | 21825698 | 21825785 | − | ✓ |
| hsa-mir-1324 | MI0006657 | — | chr3 | 75630763 | 75630858 | + | — |
| hsa-mir-1323 | MI0003786 | 7 | chr19 | 53671968 | 53672040 | + | — |
| hsa-mir-1322 | MI0006653 | — | chr8 | 10825373 | 10825443 | − | — |
| hsa-mir-1321 | MI0006652 | — | chrX | 85835780 | 85835858 | + | — |
| hsa-mir-132 | MI0000449 | 751 | chr17 | 2049908 | 2050008 | − | ✓ |
| hsa-mir-130b | MI0000748 | 869 | chr22 | 21653304 | 21653385 | + | ✓ |
| hsa-mir-130a | MI0000448 | 1813 | chr11 | 57641198 | 57641286 | + | ✓ |
| hsa-mir-1307 | MI0006444 | 249 | chr10 | 103394253 | 103394401 | − | ✓ |
| hsa-mir-1306 | MI0006443 | 6 | chr22 | 20086058 | 20086142 | + | ✓ |
| hsa-mir-1305 | MI0006372 | — | chr4 | 182169293 | 182169378 | + | — |
| hsa-mir-1304 | MI0006371 | 51 | chr11 | 93733674 | 93733764 | − | ✓ |

TABLE 2-continued

| miRNA ID | Accession | RPM | Chromosome | Start | End | Strand | Confidence |
|---|---|---|---|---|---|---|---|
| hsa-mir-1303 | MI0006370 | 48 | chr5 | 154685776 | 154685861 | + | — |
| hsa-mir-1302-9 | MI0015978 | 2 | chr9 | 30144 | 30281 | + | — |
| hsa-mir-1302-8 | MI0006369 | — | chr9 | 97363554 | 97363681 | − | — |
| hsa-mir-1302-7 | MI0006368 | 29 | chr8 | 141786242 | 141786313 | − | — |
| hsa-mir-1302-6 | MI0006367 | — | chr7 | 18127220 | 18127309 | − | — |
| hsa-mir-1302-5 | MI0006366 | — | chr20 | 50614636 | 50614785 | − | — |
| hsa-mir-1302-4 | MI0006365 | 1 | chr2 | 207269275 | 207269424 | − | — |
| hsa-mir-1302-3 | MI0006364 | 2 | chr2 | 113582959 | 113583096 | − | — |
| hsa-mir-1302-2 | MI0006363 | 2 | chr1 | 30366 | 30503 | + | — |
| hsa-mir-1302-11 | MI0015980 | 2 | chr19 | 71973 | 72110 | + | — |
| hsa-mir-1302-10 | MI0015979 | 2 | chr15 | 101960459 | 101960596 | − | — |
| hsa-mir-1302-1 | MI0006362 | — | chr12 | 112695034 | 112695176 | − | — |
| hsa-mir-1301 | MI0003815 | 50 | chr2 | 25328640 | 25328721 | − | ✓ |
| hsa-mir-1299 | MI0006359 | 6 | chr9 | 40929010 | 40929092 | − | — |
| hsa-mir-1298 | MI0003938 | 2 | chrX | 114715233 | 114715344 | + | ✓ |
| hsa-mir-1297 | MI0006358 | — | chr13 | 54311972 | 54312048 | − | — |
| hsa-mir-1296 | MI0003780 | 27 | chr10 | 63372957 | 63373048 | − | ✓ |
| hsa-mir-1295b | MI0019146 | — | chr1 | 171101739 | 171101798 | + | — |
| hsa-mir-1295a | MI0006357 | 1 | chr1 | 171101728 | 171101806 | − | — |
| hsa-mir-1294 | MI0006356 | 6 | chr5 | 154347106 | 154347247 | + | ✓ |
| hsa-mir-1293 | MI0006355 | 4 | chr12 | 50234142 | 50234212 | − | — |
| hsa-mir-1292 | MI0006433 | — | chr20 | 2652777 | 2652842 | + | — |
| hsa-mir-1291 | MI0006353 | 8 | chr12 | 48654444 | 48654530 | − | — |
| hsa-mir-1290 | MI0006352 | 798 | chr1 | 18897071 | 18897148 | − | — |
| hsa-mir-129-2 | MI0000473 | 68 | chr11 | 43581394 | 43581483 | + | ✓ |
| hsa-mir-129-1 | MI0000252 | 69 | chr7 | 128207872 | 128207943 | + | ✓ |
| hsa-mir-1289-2 | MI0006351 | 41 | chr5 | 133427596 | 133427706 | − | — |
| hsa-mir-1289-1 | MI0006350 | 146 | chr20 | 35453954 | 35454097 | − | — |
| hsa-mir-1288 | MI0006432 | — | chr17 | 16282014 | 16282088 | + | — |
| hsa-mir-1287 | MI0006349 | 7 | chr10 | 98395218 | 98395307 | − | ✓ |
| hsa-mir-1286 | MI0006348 | — | chr22 | 20249134 | 20249211 | − | — |
| hsa-mir-1285-2 | MI0006347 | 17 | chr2 | 70252918 | 70253005 | − | — |
| hsa-mir-1285-1 | MI0006346 | 392 | chr7 | 92204015 | 92204098 | − | ✓ |
| hsa-mir-1284 | MI0006431 | — | chr3 | 71541970 | 71542089 | − | ✓ |
| hsa-mir-1283-2 | MI0006430 | 102 | chr19 | 53758232 | 53758318 | + | — |
| hsa-mir-1283-1 | MI0003832 | 114 | chr19 | 53688481 | 53688567 | + | — |
| hsa-mir-1282 | MI0006429 | 115 | chr15 | 43793659 | 43793759 | − | — |
| hsa-mir-1281 | MI0006428 | — | chr22 | 41092513 | 41092566 | + | — |
| hsa-mir-128-2 | MI0000727 | 690 | chr3 | 35744476 | 35744559 | + | ✓ |

TABLE 2-continued

| miRNA ID | Accession | RPM | Chromosome | Start | End | Strand | Confidence |
|---|---|---|---|---|---|---|---|
| hsa-mir-128-1 | MI0000447 | 693 | chr2 | 135665397 | 135665478 | + | ✓ |
| hsa-mir-1279 | MI0006426 | — | chr12 | 69273157 | 69273218 | − | — |
| hsa-mir-1278 | MI0006425 | — | chr1 | 193136503 | 193136583 | + | ✓ |
| hsa-mir-1277 | MI0006419 | 41 | chrX | 118386394 | 118386471 | + | ✓ |
| hsa-mir-1276 | MI0006416 | — | chr15 | 85770496 | 85770578 | − | — |
| hsa-mir-1275 | MI0006415 | 241 | chr6 | 33999972 | 34000051 | − | — |
| hsa-mir-1273h | MI0025512 | 23 | chr16 | 24203116 | 24203231 | + | — |
| hsa-mir-1273c | MI0014171 | 12 | chr6 | 154853360 | 154853436 | + | ✓ |
| hsa-mir-1272 | MI0006408 | 67 | chr15 | 64762387 | 64762515 | − | — |
| hsa-mir-1271 | MI0003814 | 36 | chr5 | 176367946 | 176368031 | + | ✓ |
| hsa-mir-1270 | MI0006407 | — | chr19 | 20399272 | 20399354 | − | — |
| hsa-mir-127 | MI0000472 | 395 | chr14 | 100882979 | 100883075 | + | ✓ |
| hsa-mir-1269b | MI0016888 | 77 | chr17 | 12917268 | 12917342 | − | — |
| hsa-mir-1269a | MI0006406 | 82 | chr4 | 66276824 | 66276928 | + | ✓ |
| hsa-mir-1268b | MI0016748 | 53 | chr17 | 80098828 | 80098877 | + | — |
| hsa-mir-1268a | MI0006405 | 95 | chr15 | 22225278 | 22225329 | − | — |
| hsa-mir-1267 | MI0006404 | 3 | chr13 | 107531171 | 107531248 | − | — |
| hsa-mir-1266 | MI0006403 | — | chr15 | 52277117 | 52277200 | − | — |
| hsa-mir-1265 | MI0006401 | — | chr10 | 14436576 | 14436661 | + | — |
| hsa-mir-1264 | MI0003758 | 1 | chrX | 114652655 | 114652723 | + | — |
| hsa-mir-1263 | MI0006398 | — | chr3 | 164171471 | 164171556 | − | — |
| hsa-mir-1262 | MI0006397 | — | chr1 | 68183518 | 68183610 | − | — |
| hsa-mir-1261 | MI0006396 | 64 | chr11 | 90869121 | 90869202 | − | — |
| hsa-mir-1260b | MI0014197 | 913 | chr11 | 96341438 | 96341526 | + | — |
| hsa-mir-1260a | MI0006394 | 898 | chr14 | 77266218 | 77266290 | + | — |
| hsa-mir-126 | MI0000471 | 4481 | chr9 | 136670602 | 136670686 | + | ✓ |
| hsa-mir-125b-2 | MI0000470 | 11409 | chr21 | 16590237 | 16590325 | + | ✓ |
| hsa-mir-125b-1 | MI0000446 | 13830 | chr11 | 122099757 | 122099844 | − | ✓ |
| hsa-mir-125a | MI0000469 | 3993 | chr19 | 51693254 | 51693339 | + | ✓ |
| hsa-mir-1258 | MI0006392 | — | chr2 | 179860836 | 179860908 | − | — |
| hsa-mir-1257 | MI0006391 | 8 | chr20 | 61953546 | 61953662 | − | — |
| hsa-mir-1256 | MI0006390 | — | chr1 | 20988314 | 20988432 | − | ✓ |
| hsa-mir-1255b-2 | MI0006436 | 4 | chr1 | 167998660 | 167998726 | + | — |
| hsa-mir-1255b-1 | MI0006435 | 4 | chr4 | 36426366 | 36426428 | − | — |
| hsa-mir-1255a | MI0006389 | 6 | chr4 | 101330302 | 101330414 | − | ✓ |
| hsa-mir-1253 | MI0006387 | — | chr17 | 2748078 | 2748182 | − | — |
| hsa-mir-1252 | MI0006434 | — | chr12 | 79419257 | 79419321 | + | — |
| hsa-mir-1251 | MI0006386 | — | chr12 | 97491909 | 97491978 | + | — |
| hsa-mir-1250 | MI0006385 | 41 | chr17 | 81133196 | 81133308 | − | — |

TABLE 2-continued

| miRNA ID | Accession | RPM | Chromosome | Start | End | Strand | Confidence |
|---|---|---|---|---|---|---|---|
| hsa-mir-1249 | MI0006384 | 9 | chr22 | 45200954 | 45201019 | − | ✓ |
| hsa-mir-1248 | MI0006383 | 7 | chr3 | 186786672 | 186786777 | + | − |
| hsa-mir-1247 | MI0006382 | 25 | chr14 | 101560287 | 101560422 | − | ✓ |
| hsa-mir-1246 | MI0006381 | 7472 | chr2 | 176600980 | 176601052 | − | − |
| hsa-mir-1245b | MI0017431 | − | chr2 | 188978093 | 188978161 | − | − |
| hsa-mir-1245a | MI0006380 | − | chr2 | 188978092 | 188978161 | + | − |
| hsa-mir-1244-4 | MI0031511 | − | chr12 | 12111952 | 12112036 | + | − |
| hsa-mir-1244-3 | MI0015975 | − | chr12 | 9239467 | 9239551 | − | − |
| hsa-mir-1244-2 | MI0015974 | − | chr5 | 118974586 | 118974670 | + | − |
| hsa-mir-1244-1 | MI0006379 | − | chr2 | 231713314 | 231713398 | + | − |
| hsa-mir-1243 | MI0006373 | − | chr4 | 113106863 | 113106955 | + | − |
| hsa-mir-124-3 | MI0000445 | 256 | chr20 | 63178500 | 63178586 | + | ✓ |
| hsa-mir-124-2 | MI0000444 | 247 | chr8 | 64379149 | 64379257 | + | ✓ |
| hsa-mir-124-1 | MI0000443 | 254 | chr8 | 9903388 | 9903472 | − | ✓ |
| hsa-mir-1238 | MI0006328 | − | chr19 | 10552122 | 10552204 | + | − |
| hsa-mir-1237 | MI0006327 | − | chr11 | 64368602 | 64368703 | + | − |
| hsa-mir-1236 | MI0006326 | − | chr6 | 31956839 | 31956940 | − | − |
| hsa-mir-1234 | MI0006324 | 1236 | chr8 | 144400086 | 144400165 | − | − |
| hsa-mir-1233-2 | MI0015973 | 2 | chr15 | 34528290 | 34528371 | − | − |
| hsa-mir-1233-1 | MI0006323 | 2 | chr15 | 34382069 | 34382150 | − | − |
| hsa-mir-1231 | MI0006321 | − | chr1 | 201808611 | 201808702 | + | − |
| hsa-mir-122b | MI0017383 | 136 | chr18 | 58451080 | 58451152 | − | ✓ |
| hsa-mir-1229 | MI0006319 | 3 | chr5 | 179798278 | 179798346 | − | − |
| hsa-mir-1228 | MI0006318 | 4 | chr12 | 57194504 | 57194576 | + | − |
| hsa-mir-1227 | MI0006316 | − | chr19 | 2234062 | 2234149 | − | − |
| hsa-mir-1226 | MI0006313 | 5 | chr3 | 47849555 | 47849629 | + | − |
| hsa-mir-1225 | MI0006311 | − | chr16 | 2090195 | 2090284 | − | − |
| hsa-mir-1224 | MI0003764 | 18 | chr3 | 184241405 | 184241489 | + | − |
| hsa-mir-122 | MI0000442 | 1201 | chr18 | 58451074 | 58451158 | + | ✓ |
| hsa-mir-12136 | MI0039740 | 457 | chr1 | 632615 | 632685 | − | − |
| hsa-mir-12135 | MI0039739 | 225 | chr15 | 73299910 | 73299979 | + | − |
| hsa-mir-12133 | MI0039735 | − | chr1 | 94543702 | 94543779 | + | − |
| hsa-mir-12132 | MI0039734 | − | chr1 | 61846075 | 61846176 | + | − |
| hsa-mir-12131 | MI0039733 | − | chr6 | 151102675 | 151102776 | + | − |
| hsa-mir-12130 | MI0039732 | − | chr5 | 116255743 | 116255834 | + | − |
| hsa-mir-12129 | MI0039731 | − | chrX | 153335462 | 153335537 | + | − |
| hsa-mir-12128 | MI0039730 | 55 | chr16 | 85207796 | 85207895 | + | − |
| hsa-mir-12127 | MI0039729 | − | chr3 | 10280351 | 10280452 | + | − |
| hsa-mir-12126 | MI0039728 | 18 | chr9 | 130241387 | 130241488 | + | − |

TABLE 2-continued

| miRNA ID | Accession | RPM | Chromosome | Start | End | Strand | Confidence |
|---|---|---|---|---|---|---|---|
| hsa-mir-12125 | MI0039727 | — | chr5 | 168165845 | 168165929 | + | — |
| hsa-mir-12124 | MI0039726 | 6 | chr3 | 128846808 | 128846908 | + | — |
| hsa-mir-12123 | MI0039725 | — | chr8 | 79332188 | 79332274 | + | — |
| hsa-mir-12122 | MI0039724 | — | chr20 | 49863859 | 49863953 | + | — |
| hsa-mir-12121 | MI0039723 | 35 | chr14 | 104865314 | 104865411 | + | — |
| hsa-mir-12120 | MI0039722 | — | chrY | 13479177 | 13479266 | + | — |
| hsa-mir-12119 | MI0039721 | — | chr7 | 99409172 | 99409264 | + | — |
| hsa-mir-12118 | MI0039720 | — | chr5 | 173303730 | 173303817 | + | — |
| hsa-mir-12117 | MI0039719 | 12 | chr9 | 33108692 | 33108765 | + | — |
| hsa-mir-12116 | MI0039718 | 59 | chr1 | 179803924 | 179804025 | + | — |
| hsa-mir-12115 | MI0039717 | 100 | chr4 | 22515312 | 22515385 | + | — |
| hsa-mir-12114 | MI0039716 | 13 | chr22 | 50407442 | 50407524 | + | — |
| hsa-mir-12113 | MI0039715 | — | chr4 | 11783178 | 11783248 | + | — |
| hsa-mir-1208 | MI0006341 | — | chr8 | 128150116 | 128150188 | + | — |
| hsa-mir-1207 | MI0006340 | — | chr8 | 128049152 | 128049238 | + | — |
| hsa-mir-1206 | MI0006339 | — | chr8 | 128008898 | 128008956 | + | — |
| hsa-mir-1205 | MI0006338 | — | chr8 | 127960633 | 127960695 | + | — |
| hsa-mir-1204 | MI0006337 | — | chr8 | 127795962 | 127796028 | + | — |
| hsa-mir-1203 | MI0006335 | — | chr17 | 48156427 | 48156511 | − | — |
| hsa-mir-1202 | MI0006334 | 28 | chr6 | 155946797 | 155946879 | + | — |
| hsa-mir-1200 | MI0006332 | — | chr7 | 36919357 | 36919432 | − | — |
| hsa-mir-1199 | MI0020340 | — | chr19 | 14073361 | 14073479 | + | — |
| hsa-mir-1197 | MI0006656 | — | chr14 | 101025564 | 101025651 | + | — |
| hsa-mir-1193 | MI0014205 | 52 | chr14 | 101030052 | 101030129 | + | — |
| hsa-mir-1185-2 | MI0003821 | 2 | chr14 | 101044198 | 101044283 | + | ✓ |
| hsa-mir-1185-1 | MI0003844 | 2 | chr14 | 101042977 | 101043062 | + | ✓ |
| hsa-mir-1184-3 | MI0015972 | 180 | chrX | 155457517 | 155457615 | + | — |
| hsa-mir-1184-2 | MI0015971 | 180 | chrX | 155383100 | 155383198 | − | — |
| hsa-mir-1184-1 | MI0006277 | 180 | chrX | 154887360 | 154887458 | − | — |
| hsa-mir-1183 | MI0006276 | — | chr7 | 21471058 | 21471146 | + | — |
| hsa-mir-1182 | MI0006275 | — | chr1 | 231019828 | 231019924 | − | — |
| hsa-mir-1181 | MI0006274 | 3 | chr19 | 10403458 | 10403538 | − | — |
| hsa-mir-1180 | MI0006273 | 103 | chr17 | 19344506 | 19344574 | − | ✓ |
| hsa-mir-1179 | MI0006272 | — | chr15 | 88608107 | 88608197 | + | — |
| hsa-mir-1178 | MI0006271 | — | chr12 | 119713634 | 119713724 | − | — |
| hsa-mir-11401 | MI0036560 | 8 | chr16 | 87853896 | 87853964 | + | — |
| hsa-mir-11400 | MI0036559 | 12 | chr7 | 142474527 | 142474603 | + | — |
| hsa-mir-11399 | MI0036558 | — | chr1 | 112882050 | 112882129 | + | — |
| hsa-mir-11181 | MI0035972 | — | chr15 | 87946206 | 87946268 | − | — |

TABLE 2-continued

| miRNA ID | Accession | RPM | Chromosome | Start | End | Strand | Confidence |
|---|---|---|---|---|---|---|---|
| hsa-mir-10b | MI0000267 | 7790 | chr2 | 176150303 | 176150412 | + | — |
| hsa-mir-10a | MI0000266 | 5181 | chr17 | 48579838 | 48579947 | − | ✓ |
| hsa-mir-107 | MI0000114 | 11858 | chr10 | 89592747 | 89592827 | − | ✓ |
| hsa-mir-106b | MI0000734 | 1841 | chr7 | 100093993 | 100094074 | − | ✓ |
| hsa-mir-106a | MI0000113 | 7942 | chrX | 134170198 | 134170278 | − | ✓ |
| hsa-mir-10527 | MI0033674 | 2 | chr12 | 63823663 | 63823727 | + | — |
| hsa-mir-10526 | MI0033673 | — | chr11 | 122152103 | 122152156 | − | — |
| hsa-mir-10525 | MI0033672 | — | chr7 | 74595968 | 74596026 | + | — |
| hsa-mir-10524 | MI0033671 | 12 | chr6 | 78539263 | 78539309 | − | — |
| hsa-mir-10523 | MI0033669 | 36 | chr5 | 172915083 | 172915158 | + | — |
| hsa-mir-10522 | MI0033668 | — | chr5 | 17155930 | 17155992 | − | — |
| hsa-mir-105-2 | MI0000112 | 15 | chrX | 152394412 | 152394492 | − | ✓ |
| hsa-mir-105-1 | MI0000111 | 15 | chrX | 152392219 | 152392299 | − | ✓ |
| hsa-mir-10401 | MI0033425 | 156 | chr21 | 8206563 | 8206618 | + | — |
| hsa-mir-10400 | MI0033424 | 16 | chr8 | 144462485 | 144462539 | − | — |
| hsa-mir-103b-2 | MI0007262 | — | chr20 | 3917502 | 3917563 | − | — |
| hsa-mir-103b-1 | MI0007261 | 233 | chr5 | 168560904 | 168560965 | + | — |
| hsa-mir-103a-2 | MI0000108 | 12432 | chr20 | 3917494 | 3917571 | + | ✓ |
| hsa-mir-103a-1 | MI0000109 | 12432 | chr5 | 168560896 | 168560973 | − | ✓ |
| hsa-mir-10399 | MI0033423 | 19 | chr7 | 139044100 | 139044157 | − | — |
| hsa-mir-10398 | MI0033422 | 8 | chr6 | 41733554 | 41733610 | − | — |
| hsa-mir-10397 | MI0033421 | — | chr5 | 10402364 | 10402431 | + | — |
| hsa-mir-10396b | MI0033426 | — | chr21 | 8436324 | 8436374 | + | ✓ |
| hsa-mir-10396a | MI0033420 | — | chr21 | 8987617 | 8987665 | + | — |
| hsa-mir-10395 | MI0033419 | — | chr19 | 12703601 | 12703664 | − | — |
| hsa-mir-10394 | MI0033418 | — | chr19 | 58393364 | 58393446 | + | — |
| hsa-mir-10393 | MI0033417 | — | chr15 | 44717844 | 44717893 | + | — |
| hsa-mir-10392 | MI0033416 | 8 | chr11 | 64878523 | 64878609 | − | — |
| hsa-mir-10226 | MI0033056 | 169 | chr17 | 48032882 | 48032951 | + | — |
| hsa-mir-101-2 | MI0000739 | 6084 | chr9 | 4850297 | 4850375 | + | ✓ |
| hsa-mir-101-1 | MI0000103 | 6056 | chr1 | 65058434 | 65058508 | − | ✓ |
| hsa-mir-100 | MI0000102 | 10013 | chr11 | 122152229 | 122152308 | − | ✓ |
| hsa-mir-1-2 | MI0000437 | 13316 | chr18 | 21829004 | 21829088 | − | — |
| hsa-mir-1-1 | MI0000651 | 6511 | chr20 | 62554306 | 62554376 | + | ✓ |
| hsa-let-7i | MI0000434 | 17040 | chr12 | 62603686 | 62603769 | + | ✓ |
| hsa-let-7g | MI0000433 | 102832 | chr3 | 52268278 | 52268361 | − | ✓ |
| hsa-let-7f-2 | MI0000068 | 118700 | chrX | 53557192 | 53557274 | − | ✓ |
| hsa-let-7f-1 | MI0000067 | 109279 | chr9 | 94176347 | 94176433 | + | ✓ |
| hsa-let-7e | MI0000066 | 50938 | chr19 | 51692786 | 51692864 | + | ✓ |

TABLE 2-continued

| miRNA ID | Accession | RPM | Chromosome | Start | End | Strand | Confidence |
|----------|-----------|-----|------------|-------|-----|--------|------------|
| hsa-let-7d | MI0000065 | 4649 | chr9 | 94178834 | 94178920 | + | ✓ |
| hsa-let-7c | MI0000064 | 135622 | chr21 | 16539828 | 16539911 | + | ✓ |
| hsa-let-7b | MI0000063 | 83403 | chr22 | 46113686 | 46113768 | + | ✓ |
| hsa-let-7a-3 | MI0000062 | 142757 | chr22 | 46112749 | 46112822 | + | ✓ |
| hsa-let-7a-2 | MI0000061 | 142652 | chr11 | 122146522 | 122146593 | − | ✓ |
| hsa-let-7a-1 | MI0000060 | 145261 | chr9 | 94175957 | 94176036 | + | ✓ |

AAV

Recombinant AAV genomes of the disclosure comprise a disclosed nucleic acid molecule and one or more AAV ITRs flanking a nucleic acid molecule. AAV DNA in the rAAV genomes may be from any AAV serotype for which a recombinant virus can be derived including, but not limited to, AAV serotypes AAV-B1, AAVrh.74, AAV-1, AAV-2, AAV-3, AAV-4, AAV-5, AAV-6, AAV-7, AAV-8, AAV-9, AAV-10, AAV-11, AAV-12 and AAV-13. Production of pseudotyped rAAV is disclosed in, for example, WO 01/83692. Other types of rAAV variants, for example rAAV with capsid mutations, are also contemplated. See, for example, Marsic et al., Molecular Therapy, 22(11): 1900-1909 (2014). As noted in the Background section above, the nucleotide sequences of the genomes of various AAV sero-types are known in the art. To promote skeletal muscle specific expression, AAV1, AAV5, AAV6, AAV8 or AAV9 may be used.

Self-complementary AAV (scAAV) vectors are also con-templated for use in the present disclosure. scAAV vectors are generated by reducing the vector size to approximately 2500 base pairs, which comprise 2200 base pairs of unique transgene sequence plus two copies of the 145 base pair ITR packaged as a dimer. The scAAV have the ability to re-fold into double stranded DNA templates for expression. McCa-rthy, *Mol. Therap.* 16(10): 1648-1656, 2008.

DNA plasmids of the disclosure comprise a rAAV genome. The DNA plasmids are transferred to cells permis-sible for infection with a helper virus of AAV (e.g., adeno-virus, El-deleted adenovirus or herpesvirus) for assembly of the rAAV genome into infectious viral particles. Techniques to produce rAAV particles, in which an AAV genome to be packaged, rep and cap genes, and helper virus functions are provided to a cell, are known in the art. Production of rAAV requires that the following components are present within a single cell (denoted herein as a packaging cell): a rAAV genome, AAV rep and cap genes separate from (i.e., not in) the rAAV genome, and helper virus functions. The AAV rep and cap genes may be from any AAV serotype for which recombinant virus can be derived and may be from a different AAV serotype than the rAAV genome ITRs, includ-ing, but not limited to, AAV serotypes AAV-1, AAV-2, AAV-3, AAV-4, AAV-5, AAV-6, AAV-7, AAV-8, AAV-9, AAV-10, AAV-11, AAV-12 and AAV-13. Production of pseudotyped rAAV is disclosed in, for example, WO 01/83692 which is incorporated by reference herein in its entirety.

A method of generating a packaging cell is to create a cell line that stably expresses all the necessary components for AAV particle production. For example, a plasmid (or mul-tiple plasmids) comprising a rAAV genome lacking AAV rep and cap genes, AAV rep and cap genes separate from the rAAV genome, and a selectable marker, such as a neomycin resistance gene, are integrated into the genome of a cell. AAV genomes have been introduced into bacterial plasmids by procedures such as GC tailing (Samulski et al., 1982, Proc. Natl. Acad. S6. USA, 79:2077-2081), addition of synthetic linkers containing restriction endonuclease cleav-age sites (Laughlin et al., 1983, Gene, 23:65-73) or by direct, blunt-end ligation (Senapathy & Carter, 1984, J. Biol. Chem., 259:4661-4666). The packaging cell line is then infected with a helper virus such as adenovirus. The advan-tages of this method are that the cells are selectable and are suitable for large-scale production of rAAV. Other examples of suitable methods employ adenovirus or baculovirus rather than plasmids to introduce rAAV genomes and/or rep and cap genes into packaging cells.

General principles of rAAV production are reviewed in, for example, Carter, 1992, Current Opinions in Biotechnol-ogy, 1533-539; and Muzyczka, 1992, Curr. Topics in Micro-bial. and Immunol., 158:97-129). Various approaches are described in Ratschin et al., Mol. Cell. Biol. 4:2072 (1984); Hermonat et al., Proc. Natl. Acad. Sci. USA, 81:6466 (1984); Tratschin et al., Mol. Cell. Biol. 5:3251 (1985); McLaughlin et al., J. Virol., 62:1963 (1988); and Lebkowski et al., 1988 Mol. Cell. Biol., 7:349 (1988). Samulski et al. (1989, J. Virol., 63:3822-3828); U.S. Pat. No. 5,173,414; WO 95/13365 and corresponding U.S. Pat. No. 5,658.776; WO 95/13392; WO 96/17947; PCT/US98/18600; WO 97/09441 (PCT/US96/14423); WO 97/08298 (PCT/US96/13872); WO 97/21825 (PCT/US96/20777); WO 97/06243 (PCT/FR96/01064); WO 99/11764; Perrin et al. (1995) Vaccine 13:1244-1250; Paul et al. (1993) Human Gene Therapy 4:609-615; Clark et al. (1996) Gene Therapy 3:1124-1132; U.S. Patent. No. 5,786,211; U.S. Patent No. 5,871,982; and U.S. Pat No. 6,258,595. The foregoing documents are hereby incorporated by reference in their entirety herein, with particular emphasis on those sections of the documents relating to rAAV production.

The disclosure thus provides packaging cells that produce infectious rAAV. In one embodiment packaging cells may be stably transformed cancer cells such as HeLa cells, 293 cells and PerC.6 cells (a cognate 293 line). In another embodi-ment, packaging cells are cells that are not transformed cancer cells, such as low passage 293 cells (human fetal kidney cells transformed with El of adenovirus), MRC-5 cells (human fetal fibroblasts), WI-38 cells (human fetal fibroblasts), Vero cells (monkey kidney cells) and FRhL-2 cells (rhesus fetal lung cells).

Recombinant AAV (i.e., infectious encapsidated rAAV particles) of the disclosure comprise a rAAV genome. Embodiments include, but are not limited to, the rAAV named "AAV.miDUX4.405" including a genome encoding the DUX4 miRNA hDux.mi405 (encoded by the DNA set out in SEQ ID NO: 1 and the rAAV named "AAV.miDUX4.1155" including a genome encoding the DUX4 miRNA hDux.mil155 (encoded by the DNA set out in SEQ ID NO: 2). In exemplary embodiments, the genomes of both rAAV lack AAV rep and cap DNA, that is, there is no AAV rep or cap DNA between the ITRs of the genomes. Examples of rAAV that may be constructed to comprise the nucleic acid molecules of the disclosure are set out in International Patent Application No. PCT/US2012/047999 (WO 2013/016352) incorporated by reference herein in its entirety.

The rAAV may be purified by methods such as by column chromatography or cesium chloride gradients. Methods for purifying rAAV vectors from helper virus are known in the art and include methods disclosed in, for example, Clark et al., Hum. Gene Ther., 10(6): 1031-1039 (1999); Schenpp and Clark, Methods Mol. Med., 69 427-443 (2002); U.S. Pat. No. 6,566,118 and WO 98/09657.

In another embodiment, the disclosure contemplates compositions comprising a disclosed rAAV. Compositions of the disclosure comprise rAAV in a pharmaceutically acceptable carrier. The compositions may also comprise other ingredients such as diluents and adjuvants. Acceptable carriers, diluents and adjuvants are nontoxic to recipients and are preferably inert at the dosages and concentrations employed, and include buffers such as phosphate, citrate, or other organic acids; antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, pluronics or polyethylene glycol (PEG).

Titers of rAAV to be administered in methods of the disclosure will vary depending, for example, on the particular rAAV, the mode of administration, the treatment goal, the individual, and the cell type(s) being targeted, and may be determined by methods known in the art. Titers of rAAV may range from about $1\times10^6$, about $1\times10^7$, about $1\times10^8$, about $1\times10^9$, about $1\times10^{10}$, about $1\times10^{11}$, about $1\times10^{12}$, about $1\times10^{13}$ to about $1\times10^{14}$ or more DNase resistant particles (DRP) per ml. Dosages may also be expressed in units of viral genomes (vg).

Methods of transducing a target cell with rAAV, in vivo or in vitro, are contemplated by the disclosure. The in vivo methods comprise the step of administering an effective dose, or effective multiple doses, of a composition comprising a rAAV of the disclosure to an animal (including a human being) in need thereof. If the dose is administered prior to development of a disorder/disease, the administration is prophylactic. If the dose is administered after the development of a disorder/disease, the administration is therapeutic. In embodiments of the disclosure, an effective dose is a dose that alleviates (eliminates or reduces) at least one symptom associated with the disorder/disease state being treated, that slows or prevents progression to a disorder/disease state, that slows or prevents progression of a disorder/disease state, that diminishes the extent of disease, that results in remission (partial or total) of disease, and/or that prolongs survival. An example of a disease contemplated for prevention or treatment with the disclosed methods is FSHD.

Combination therapies are also contemplated by the disclosure. Combination as used herein includes both simultaneous treatment and sequential treatments. Combinations of methods of the disclosure with standard medical treatments (e.g., corticosteroids) are specifically contemplated, as are combinations with novel therapies.

Administration of an effective dose of the compositions may be by routes known in the art including, but not limited to, intramuscular, parenteral, intravenous, oral, buccal, nasal, pulmonary, intracranial, intraosseous, intraocular, rectal, or vaginal. Route(s) of administration and serotype(s) of AAV components of the rAAV (in particular, the AAV ITRs and capsid protein) of the disclosure may be chosen and/or matched by those skilled in the art taking into account the infection and/or disease state being treated and the target cells/tissue(s) that are to express the DUX4 miRNAs.

The disclosure provides for local administration and systemic administration of an effective dose of recombinant AAV and compositions of the disclosure. For example, systemic administration is administration into the circulatory system so that the entire body is affected. Systemic administration includes enteral administration such as absorption through the gastrointestinal tract and parental administration through injection, infusion or implantation.

In particular, actual administration of rAAV of the present disclosure may be accomplished by using any physical method that will transport the rAAV recombinant vector into the target tissue of an animal. Administration according to the disclosure includes, but is not limited to, injection into muscle, the bloodstream and/or directly into the liver. Simply resuspending a rAAV in phosphate buffered saline has been demonstrated to be sufficient to provide a vehicle useful for muscle tissue expression, and there are no known restrictions on the carriers or other components that can be co-administered with the rAAV (although compositions that degrade DNA should be avoided in the normal manner with rAAV). Capsid proteins of a rAAV may be modified so that the rAAV is targeted to a particular target tissue of interest such as muscle. See, for example, WO 02/053703, the disclosure of which is incorporated by reference herein. Pharmaceutical compositions can be prepared as injectable formulations or as topical formulations to be delivered to the muscles by transdermal transport. Numerous formulations for both intramuscular injection and transdermal transport have been previously developed and can be used in the practice of the disclosed methods and compositions. The rAAV can be used with any pharmaceutically acceptable carrier for ease of administration and handling.

For purposes of intramuscular injection, solutions in an adjuvant such as sesame or peanut oil or in aqueous propylene glycol can be employed, as well as sterile aqueous solutions. Such aqueous solutions can be buffered, if desired, and the liquid diluent first rendered isotonic with saline or glucose. Solutions of rAAV as a free acid (DNA contains acidic phosphate groups) or a pharmacologically acceptable salt can be prepared in water suitably mixed with a surfactant such as hydroxypropylcellulose. A dispersion of rAAV can also be prepared in glycerol, liquid polyethylene glycols and mixtures thereof and in oils. Under ordinary conditions of storage and use, these preparations contain a preservative to prevent the growth of microorganisms. In this connection, the sterile aqueous media employed are all readily obtainable by techniques known to those skilled in the art.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating actions of microorganisms such as bacteria and fungi. The carrier can be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating such as lecithin, by the maintenance of the required particle size in the case of a dispersion and by the use of surfactants. The prevention of the action of microorganisms can be brought about by various antibacterial and antifungal agents, for example, parabens, chlorobutanol, phenol, sorbic acid, thimerosal and the like. In many cases it will be preferable to include isotonic agents, for example, sugars or sodium chloride. Prolonged absorption of the injectable compositions can be brought about by use of agents delaying absorption, for example, aluminum monostearate and gelatin.

Sterile injectable solutions are prepared by incorporating rAAV in the required amount in the appropriate solvent with various other ingredients enumerated above, as required, followed by filter sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique that yield a powder of the active ingredient plus any additional desired ingredient from the previously sterile-filtered solution thereof.

Transduction with rAAV may also be carried out in vitro. In one embodiment, desired target muscle cells are removed from the subject, transduced with rAAV and reintroduced into the subject. Alternatively, syngeneic or xenogeneic muscle cells can be used where those cells will not generate an inappropriate immune response in the subject.

Suitable methods for the transduction and reintroduction of transduced cells into a subject are known in the art. In one embodiment, cells can be transduced in vitro by combining rAAV with muscle cells, e.g., in appropriate media, and screening for those cells harboring the DNA of interest using techniques such as Southern blots and/or PCR, or by using selectable markers. Transduced cells can then be formulated into pharmaceutical compositions, and the composition introduced into the subject by various techniques, such as by intramuscular, intravenous, subcutaneous and intraperitoneal injection, or by injection into smooth and cardiac muscle, using e.g., a catheter.

Transduction of cells with rAAV of the disclosure results in sustained expression of DUX4 miRNAs. The present disclosure thus provides methods of administering/delivering rAAV which express DUX4 miRNAs to an animal, preferably a human being. These methods include transducing tissues (including, but not limited to, tissues such as muscle, organs such as liver and brain, and glands such as salivary glands) with one or more disclosed rAAV. Transduction may be carried out with gene cassettes comprising tissue specific control elements. For example, one embodiment provides methods of transducing muscle cells and muscle tissues directed by muscle specific control elements, including, but not limited to, those derived from the actin and myosin gene families, such as from the myoD gene family [See Weintraub et al., *Science,* 251: 761-766 (1991)], the myocyte-specific enhancer binding factor MEF-2 [Cserjesi and Olson, *Mol Cell Biol* 11: 4854-4862 (1991)], control elements derived from the human skeletal actin gene [Muscat et al., *Mol Cell Biol,* 7: 4089-4099 (1987)], the cardiac actin gene, muscle creatine kinase sequence elements [See Johnson et al., *Mol Cell Biol,* 9:3393-3399 (1989)] and the murine creatine kinase enhancer (mCK) element, control elements derived from the skeletal fast-twitch troponin C gene, the slow-twitch cardiac troponin C gene and the slow-twitch troponin I gene: hypoxia-inducible nuclear factors (Semenza et al., *Proc Natl Acad Sci USA,* 88: 5680-5684 (1991)), steroid-inducible elements and promoters including the glucocorticoid response element (GRE) (See Mader and White, *Proc. Nall. Acad. Sci. USA* 90: 5603-5607 (1993)), and other control elements.

Muscle tissue is an attractive target for in vivo DNA delivery, because it is not a vital organ and is easy to access. The disclosure contemplates sustained expression of miRNAs from transduced myofibers.

By "muscle cell" or "muscle tissue" is meant a cell or group of cells derived from muscle of any kind (for example, skeletal muscle and smooth muscle, e.g. from the digestive tract, urinary bladder, blood vessels or cardiac tissue). Such muscle cells may be differentiated or undifferentiated, such as myoblasts, myocytes, myotubes, cardiomyocytes and cardiomyoblasts.

The term "transduction" is used to refer to the administration/delivery of DUX4 miRNAs to a recipient cell either in vivo or in vitro, via a replication-deficient rAAV resulting in expression of a DUX4 miRNA by the recipient cell.

Thus, the disclosure provides methods of administering an effective dose (or doses, administered essentially simultaneously or doses given at intervals) of rAAV that encode DUX4 miRNAs to a patient in need thereof.

DUX4 and Facioscapulohumeral Muscular Dystrophy

Muscular dystrophies (MDs) are a group of genetic diseases. The group is characterized by progressive weakness and degeneration of the skeletal muscles that control movement or breathing. Some forms of MD develop in infancy or childhood, while others may not appear until middle age or later. The disorders differ in terms of the distribution and extent of muscle weakness (some forms of MD also affect cardiac muscle), the age of onset, the rate of progression, and the pattern of inheritance.

Facioscapulohumeral muscular dystrophy (FSHD) is a complex autosomal dominant disorder characterized by progressive and asymmetric weakness of facial, shoulder and limb muscles. Symptoms typically arise in adulthood with most patients showing clinical features before age thirty. About five percent of patients develop symptoms as infants or juveniles and these are generally more severely affected. Clinical presentation can vary from mild (some limited muscle weakness) to severe (wheelchair dependence). Historically, FSHD was classified as the third most common MD, affecting one in 20,000 individuals worldwide. However, recent data indicate FSHD is the most common MD in Europe, suggesting its worldwide incidence could be as high as 1 in 8,333.

Typical FSHD cases (FSHD1A, heretofore referred to as FSHD) are linked to heterozygous chromosomal deletions that decrease the copy number of 3.3 kilobase (kb) D4Z4 repeats on human chromosome 4q35. Simplistically, normal individuals have 11-100 tandemly-repeated D4Z4 copies on both 4q35 alleles, while patients with FSHD have one normal and one contracted allele containing 1-10 repeats. In addition, FSHD-associated D4Z4 contractions must occur on specific disease-permissive chromosome 4q35 backgrounds (called 4qA). Importantly, no genes are completely lost or structurally mutated as a result of FSHD-associated deletions. Instead, genetic changes associated with FSHD give rise to expression of the toxic DUX4 gene, which is damaging to muscle. FSHD2 (also known as FSHD1B) is phenotypically identical to FSHD1, is associated with DUX4 expression, and requires the 4qA chromosomal background. FSHD2 is not associated with D4Z4 repeat contraction, but is instead caused by mutation in the SMCHD1 gene, which is a chromatin regulator normally involved in repressing the DUX4 locus at 4qA. Mutated SMCHD1 proteins fail to participate in adding heterochromatin to the 4qA DUX4 allele, thereby allowing DUX4 gene expression.

In the leading FSHD pathogenesis model, D4Z4 contractions are proposed to cause epigenetic changes that permit expression of the DUX4 gene. As a result, the aberrant over-expression of otherwise silent or near-silent DUX4 gene, and the genes it regulates, may ultimately cause FSHD. This model is consistent with data showing normal 4q35 D4Z4 repeats have heterochromatin characteristics, while FSHD-linked D4Z4 repeats contain marks more indicative of actively transcribed euchromatin. These transcription-permissive epigenetic changes, coupled with the observation that complete monosomic D4Z4 deletions (i.e., zero repeats) do not cause FSHD, support the hypothesis that D4Z4 repeats harbor potentially myopathic open reading frames (ORFs), which are abnormally expressed in FSHD muscles. This notion was initially considered in 1994, when a D4Z4-localized ORF, called DUX4, was first identified. However, the locus had some characteristics of an unexpressed pseudogene and DUX4 was therefore summarily dismissed as an FSHD candidate. For many years thereafter, the search for FSHD-related genes was mainly focused outside the D4Z4 repeats, and although some intriguing candidates emerged from these studies, no single gene had been conclusively linked to FSHD development. This slow progress led to the re-emergence of DUX4 as an FSHD candidate in 2007. Even as of 2010 though, researchers continued to highlight other genes as candidates. See, for example, Wuebbles et al., *Int. J. Clin. Exp. Pathol.*, 3(4): 386-400 (2010) highlighting the FSHD region gene 1 (frg1). In contrast, Wallace et al., *Mol. Ther.*, 17(Suppl. 1): S151 (2009); Wei et al., *Mol. Ther.*, 17(Suppl. 1): S200 (2009); and the Lemmers et al. report from the *Sciencexpress issue of Aug.* 19, 2010 highlight DUX4. Neguembor and Gabellini, *Epigenomics*, 2(2): 271-287 (2010) is a recent review article regarding FSHD.

The role of DUX4 in FSHD pathogenesis can be explained as follows. First, D4Z4 repeats contain identical DUX4 coding regions, and D4Z4 repeats also harbor smaller sense and antisense transcripts, including some resembling microRNAs. Over-expressed DUX4 transcripts and a ~50 kDa full-length DUX4 protein are found in biopsies and cell lines from FSHD patients. These data are consistent with a transcriptional de-repression model of FSHD pathogenesis. In addition, unlike pseudogenes, D4Z4 repeats and DUX4 likely have functional importance, since tandemly-arrayed D4Z4 repeats are conserved in at least eleven different placental mammalian species (non-placental animals lack D4Z4 repeats), with the greatest sequence conservation occurring within the DUX4 ORF. Second, over-expressed DUX4 is toxic to tissue culture cells and embryonic progenitors of developing lower organisms in vivo. This toxicity occurs at least partly through a pro-apoptotic mechanism, indicated by Caspase-3 activation in DUX4 transfected cells, and presence of TUNEL-positive nuclei in developmentally arrested *Xenopus* embryos injected with DUX4 mRNA at the two-cell stage. These findings are consistent with studies showing some pro-apoptotic proteins, including Caspase-3, are present in FSHD patient muscles. In addition to stimulating apoptosis, DUX4 may negatively regulate myogenesis. Human DUX4 inhibits differentiation of mouse C2C12 myoblasts in vitro, potentially by interfering with PAX3 and/or PAX7, and causes developmental arrest and reduced staining of some muscle markers when delivered to progenitor cells of zebrafish or *Xenopus* embryos. Finally, aberrant DUX4 function is directly associated with potentially important molecular changes seen in FSHD patient muscles. Specifically, full-length human DUX4 encodes an approximately 50 kDa double homeodomain transcription factor, and DUX4 targets can be found at elevated levels in FSHD patient muscles. These data support that DUX4 catalyzes numerous downstream molecular changes that are incompatible with maintaining normal muscle integrity.

BRIEF DESCRIPTION OF THE DRAWING

FIG. 1 shows the wild type U6-1 promoter (SEQ ID NO: 3)

Figure 4:
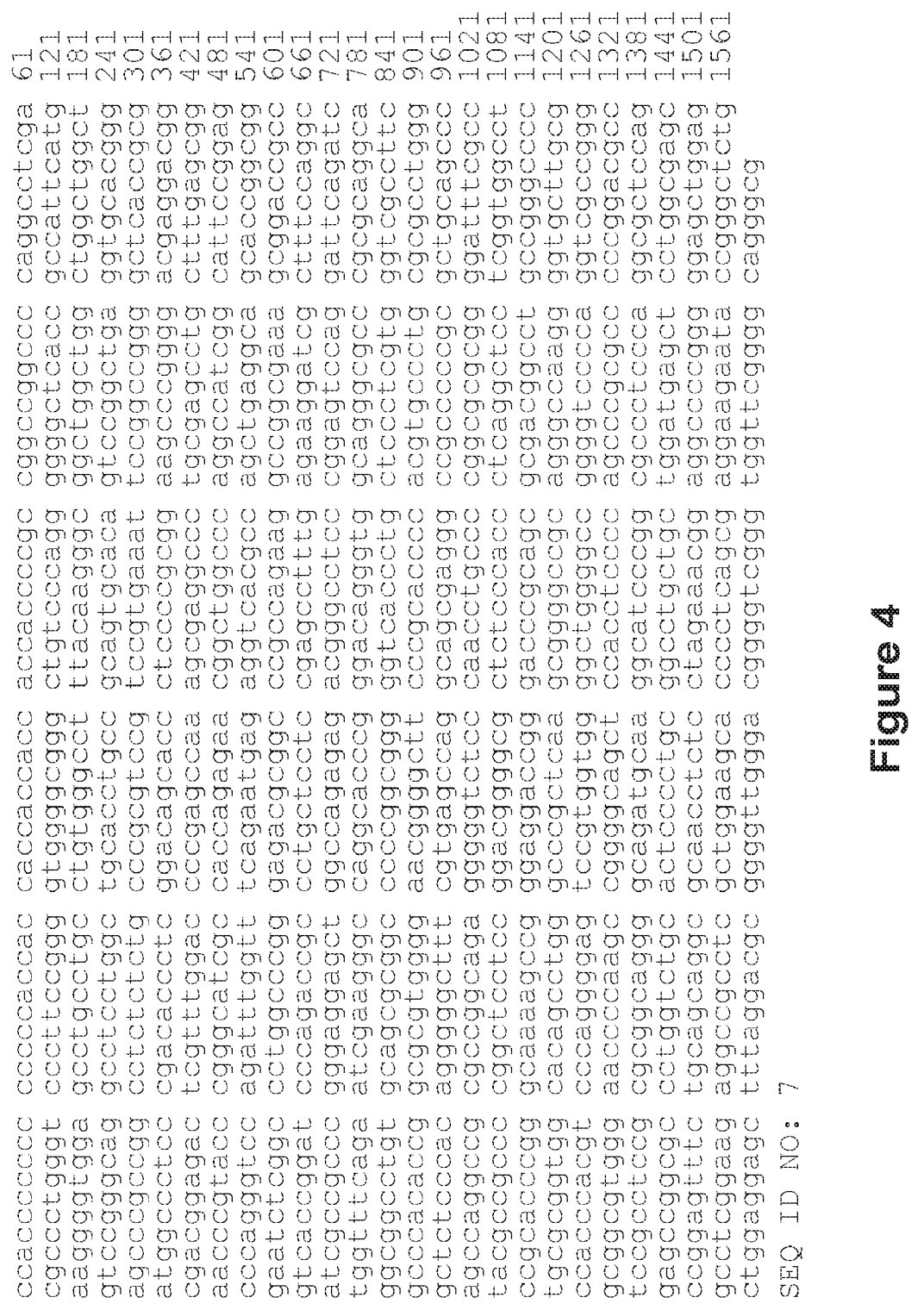

FIG. 4 shows the human DUX4 DNA sequence (SEQ ID NO: 7).

SEQUENCES

SEQ ID NO: 1 (miDUX4.405 or miDUX4-1)
SEQ ID NO: 2 (miDUX4.1155 or miDUX4-2)

SEQ ID NOS: 10-10912, 10971, 10972: Exemplary miRNA mature guide strand nucleotide sequences SEQ ID NO: 3 wild type U6-1 promoter SEQ ID NO: 4 weakened U6-1 promoter with mutations within the PSE region.

SEQ ID NO: 5 Binding site for miR-122 (5' TATT-TAGTGTGAT AATGGTGTTT 3')

SEQ ID NO: 6—Binding site for miRNA-208 (5' ACGAGCcTTTT GCTCGTCTTAT 3')

SEQ ID NO: 8—miDUX4.405 (miDUX4-1) folded miRNA

SEQ ID NO: 9—miDUX4.1155 (miDUX4-2) folded miRNA

SEQ ID NO: 7—DUX4 gene sequence

SEQ ID NOS: 10913-10968 Exemplary nucleic acid sequences comprising the mature guide strand of miDUX4 and a binding site for miR-122 or miR-208 (also shown in Table 1)

SEQ ID NO: 10969—Binding site for miR-122 (5' UAUUUAGU GUGAUAAUGGUGUUU 3')

SEQ ID NO: 10970—Binding site for miR-208 (5' ACGAGCcUUUU GCUCGUCUUAU 3')

SEQ ID NO: 10973—miDUX4.405 (miDUX4-1) mature guide strand nucleotide sequence

SEQ ID NO: 10974—miDUX4.1155 (miDUX4-2) mature guide strand nucleotide sequence

When mature guide stand sequences are presented as DNA sequences herein, one of skill in the art understands that this DNA sequence serves as a template for transcription to RNA wherein the thymidine bases are converted to uridine bases.

Thus, aspects and embodiments of the disclosure are illustrated by the following examples. Example 1 describes the liver and heart detargeted, U6 promoter system. Example 2 describes the luciferase assay for determining the effect of the miRNAs expression of DUX4 miRNAs. Example 3 describes rAAV vectors encoding DUX4 miRNAs.

EXAMPLE 1

Liver and Heart De-Targeted, U6 Promoter System

AAV vectors expressing the miDUX4.405 sequence (SEQ ID NO: 1) from the wild-type U6 promoter were generated. Muscles were co-injected with AAV.DUX4. The wild-type U6 system protected muscles from damage resulting from high DUX4 expression.

Figures 2A, 2B:
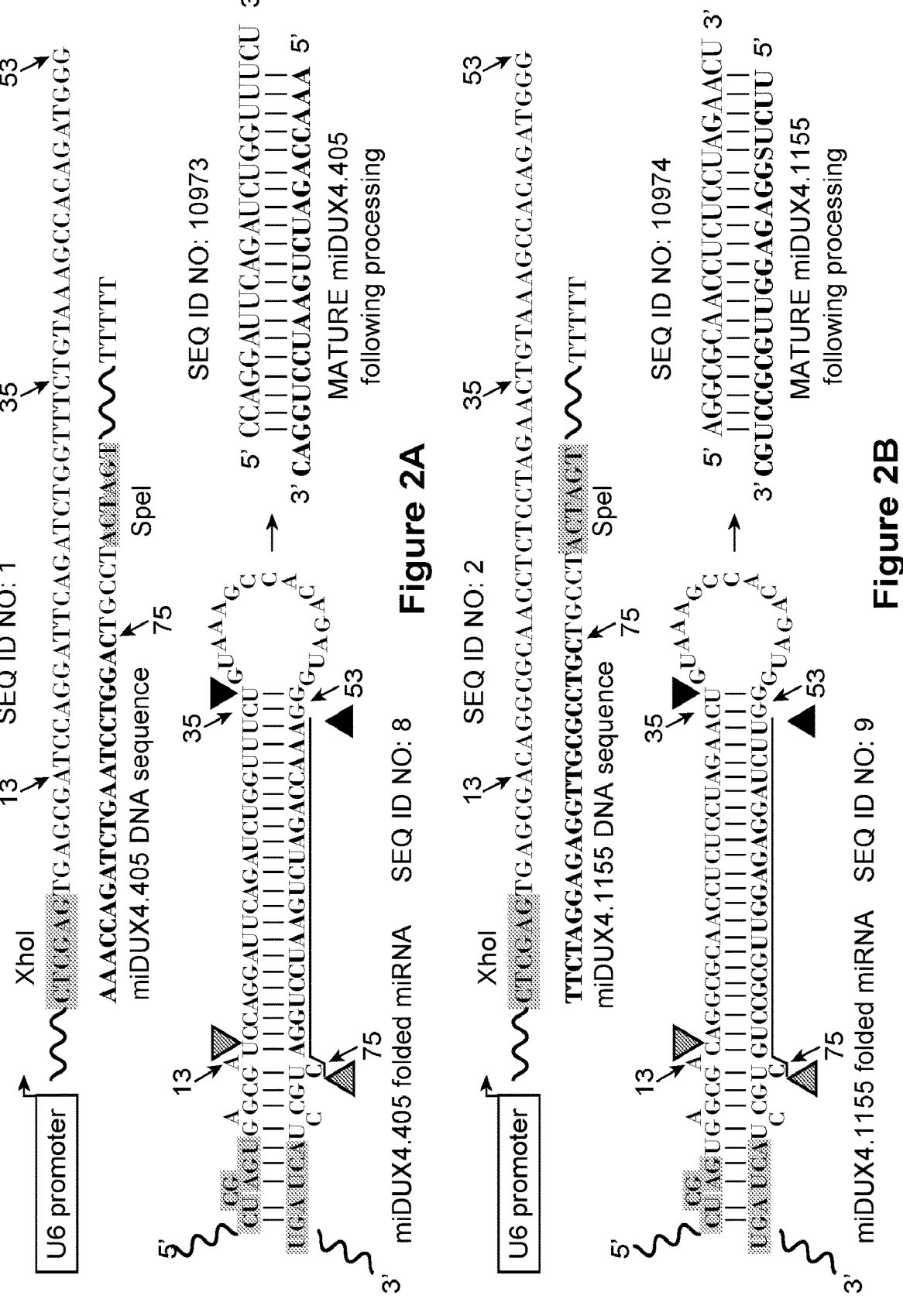
FIGS. 2A and 2B set out sequences of DUX4 targeted miRNAs. In each panel, the top sequences indicate the DNA templates from which each respective miRNA is transcribed. In the top panel, the DNA template miDUX4.405 (miDUX4-1 or mi405) is SEQ ID NO: 1. In the bottom panel, the DNA template miDUX4.1155 (miDUX4-2; or mi1155) is SEQ ID NO: 2. The folded miRNA transcripts are shown as hairpin structures. The miDUX4.405 folded miRNAs is SEQ ID NO: 8. The miDUX4.1155 folded miRNA is SEQ ID NO: 9. The mature miDUX4.405 and miDUX4.1155 sequences arise following processing in target cells by host miRNA processing machinery (including Drosha, DGCR8, Dicer, and Exportin-5). Sequences shaded in gray indicate restriction sites used for cloning each miRNA into the U6T6 vector. CTCGAG is an XhoI site and ACTAGT is a SpeI site (CUCGAG and ACUAGU in RNA, where the U is a uracil base). The red sequence indicates the mature miRNA antisense guide strand that ultimately helps catalyze cleavage of the DUX4 target mRNA. This sequence is also underlined in the miRNA hairpin portions of this diagram. The gray and black arrowheads indicate Drosha- and Dicer- catalyzed cleavage sites, respectively. The numbers 13, 35, 53, and 75 are provided for orientation. The sequences between (and including) positions 35-53 are derived from the natural human mir-30a sequence, except the A at position 39, which is a G is the normal mir-30a sequence. This nucleotide was changed to an A to facilitate folding of the miRNA loop, based on in silico RNA folding models. The base of the stem (5' of position 13 and 3' of position 75) is also derived from mir-30a structure and sequence with some modifications depending on the primary sequence of the guide strand. Specifically, the nucleotide at position 13 can vary to help facilitate a required mismatched between the position 13 and 75 nucleotides. This bulged structure is hypothesized to facilitate proper Drosha cleavage.
Figure 3:
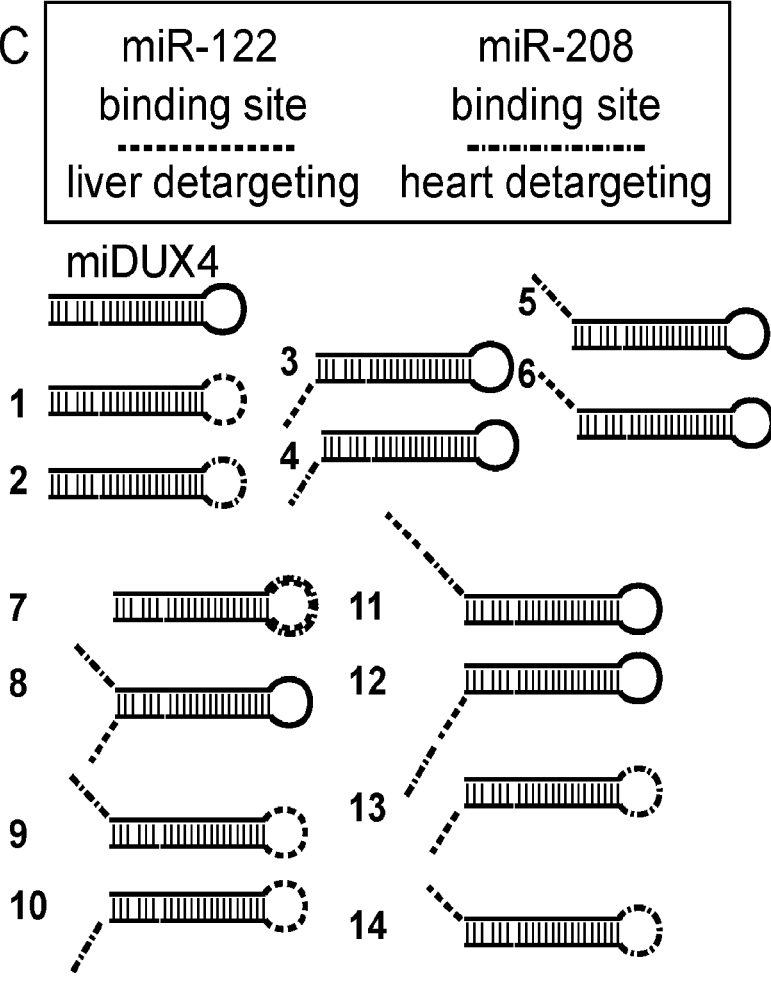
FIG. 3 shows the strategy for de-targeting miDUX4 in heart and liver. The perfect binding sites for mir-122 (liver) and mir-208 (heart) are indicated in the figure. Evidence that mir-122-modified miDUX4 is functional against a DUX4-luciferase target, and that liver cells expressing mir-122 can inhibit miDUX4 silencing when mir-122 binding sites are included in the miDUX4 sequence.

One option for skeletal muscle specific expression is to use the AAV6 vector, as it primarily transduces skeletal muscle, liver, and heart following vascular delivery, and significantly less in other tissues. To avoid expression in liver and heart, the U6 promoter system detargets miDUX4 in those tissues. To do this, binding sites for mir-122 and mir-208) (liver- and heart-specific natural microRNAs) are incorporated at various locations within the miDUX4 transcript as shown in FIG. 3. The de-targeted miDUX4 transcripts expression are measured, using the DUX4-luciferase target described below in Example 2.

EXAMPLE 2

Luciferase Assay for Effect of Expression of DUX4 miRNAs

Expression of the DUX4 target sequence in the presence of the DUX4 miRNAs is assayed. A lipofectamine 2000 transfection is done in 293 cells in a 96-well, white-walled assay plate. 140,000 cells are transfected with 20 ng of a Renilla-firefly plasmid containing the DUX4 target sequence and 180 ng of various DUX4 miRNA-encoding vectors, including U6T6-driven miDux4.405 or miDux4.1155 vectors from Example 1. A luciferase assay is performed 24 hours later.

The media is removed from the cells and 20 μl of lysis buffer was added per well. The plate is put on a shaker for 15 minutes at room temperature before adding 50 μl of luciferase substrate. The first reading is taken 10 minutes later. Next, 50 μl of Stop and Glo luciferase substrate is added and the second reading is taken 10 minutes later. The Renilla expression is divided by the firefly expression to calculate the relative expression. The relative expression is then normalized to the expression of cells that were transfected with a control miRNA that targets eGFP. The DUX4 miRNAs miDUX4.405 and miDUX4.1155 are the most effective at reducing luciferase protein expression in transfected cells. The de-targeted miDUX4 transcripts are destroyed by mir-122 and mir-208 RISC complexes in the liver and heart, respectively, using the DUX4-luciferase target described below in Example 1.

EXAMPLE 3

Production of rAAV Encoding DUX4 MicroRNAs

Vector is produced by co-transfection in HEK293 cells of three plasmids (pAdhelper, AAV helper, and the rAAV genome containing miDUX4; described in detail below), followed by cell-harvesting, vector purification, titration, and quality control assays.

Plasmids: pAdhelper contains the adenovirus genes E2A, E4 ORF6, and VA I/II; AAV helper plasmids contain AAV rep2 and cap6 (for example, for an AAV serotype 6 preparation, the capsid gene would be called cap6); the rAAV plasmid contains AAV inverted terminal repeat (ITRs) sequences flanking the genetic elements to be packaged into the vector. For the AAV.miDUX4, this includes the U6.miDUX4 cloned upstream of the CMV.eGFP reporter gene.

Transfection: Plasmids are transfected into 293 cells (Corning 10-Stack) using $CaPO_4$ at a 4:4:1 ratio (20 μg pAd helper: 20 μg AAV helper: 5 ug rAAV vector plasmid per plate.

Cell harvesting: Forty-eight hr post-transfection, cells are harvested and resuspended in 20 mM Tris (pH 8.0), 1 mM $MgCl_2$ and 150 mM NaCl (T20M1N150) at a density of $5 \times 10^6$ cells/ml. Cells are lysed by four sequential freeze/thaw cycles and Benzonase nuclease (AIC, Stock: 250 U/μl) added to a final concentration of 90 U/ml before cell lysate clarification.

Vector Purification and Titration: Clarified lysates are subjected to iodixanol step gradient purification as previously described (Xiao, X, et al. J. Virol 72:2224-32). The 40% iodixanol layer (containing rAAV) is diluted 5-fold with a no-salt dilution buffer (pH varying depending on serotype) and applied to a Hi-Trap HP-Q/S column. Upon elution with a NaCl salt gradient, peak 1 ml fractions (typically 3-5) are pooled, dialyzed with T20M1N200 (pH 8.0), then sterile filtered and supplemented with 0.001% Pluronic F68. Vectors are stored at −80° C. Purified virus was titered for vg using Q-PCR as previously described (Schnepp and Clark, *Methods Mol. Med.*, 69:427-443 (2002)).

SEQUENCE LISTING

The patent contains a lengthy sequence listing. A copy of the sequence listing is available in electronic form from the USPTO web site (https://seqdata.uspto.gov/docdetail?docId=US12618065B2). An electronic copy of the sequence listing will also be available from the USPTO upon request and payment of the fee set forth in 37 CFR 1.19(b)(3).

I claim:

1. A method of inhibiting expression of the double homeo-box 4 (DUX4) gene in a cell comprising contacting the cell with a recombinant adeno-associated virus comprising a nucleic acid comprising (a) a nucleotide sequence encoding a U6 promoter;

(b) a nucleotide sequence encoding a mature guide strand of a miRNA targeting DUX4 mRNA, wherein the mature guide strand of the miRNA comprises the nucleotide sequence of SEQ ID NO: 7397 or 8147;

(c) a nucleotide sequence comprising at least one copy of a detargeting sequence comprising the mir-122 binding site having the nucleotide sequence of SEQ ID NO: 5 or 66, and/or at least one copy of a detargeting sequence comprising the miR-208 binding site having the nucleotide sequence of SEQ ID NO: 6 or 67; and (d) 5-6 thymidines at the 5' end.

2. A method of delivering double homeobox 4 (DUX4) miRNA-encoding DNA to the skeletal muscle of an animal in need thereof, comprising contacting the skeletal muscle with a recombinant adeno-associated virus comprising a nucleic acid comprising (a) a nucleotide sequence encoding a U6 promoter;

(b) a nucleotide sequence encoding a mature guide strand of a miRNA targeting DUX4 mRNA, wherein the mature guide strand of the miRNA comprises the nucleotide sequence of SEQ ID NO: 7397 or 8147;

(c) a nucleotide sequence comprising at least one copy of a detargeting sequence comprising the mir-122 binding site having the nucleotide sequence of SEQ ID NO: 5 or 66, and/or at least one copy of a detargeting sequence comprising the miR-208 binding site having the nucleotide sequence of SEQ ID NO: 6 or 67; and (d) 5-6 thymidines at the 5' end.

3. A method of treating facioscapulohumeral muscular dystrophy in a subject comprising administering to the subject an effective amount of a recombinant adeno-associated virus comprising (a) a nucleotide sequence encoding a U6 promoter;

(b) a nucleotide sequence encoding a mature guide strand of a miRNA targeting DUX4 mRNA, wherein the mature guide strand of the miRNA comprises the nucleotide sequence of SEQ ID NO: 7397 or 8147;

(c) a nucleotide sequence comprising at least one copy of a detargeting sequence comprising the mir-122 binding site having the nucleotide sequence of SEQ ID NO: 5 or 66, and/or at least one copy of a detargeting sequence comprising the miR-208 binding site having the nucleotide sequence of SEQ ID NO: 6 or 67; and (d) 5-6 thymidines at the 5' end.

4. The method of claim 2, wherein the recombinant adeno-associated virus is administered by intramuscular injection, transdermal transport, injection into the blood stream or injection into the liver.

5. The method of claim 3, wherein the recombinant adeno- associated virus is administered by intramuscular injection, transdermal transport, injection into the blood stream or injection into the liver.

6. The method of claim 1, wherein the U6 promoter comprises the nucleotide sequence of SEQ ID NO: 3.

7. The method of claim 1, wherein the nucleic acid comprises the polynucleotide sequence of any one of SEQ ID NOS: 1, 2, and 10913-10968.

8. The method of claim 1, wherein the adeno-associated virus (AAV) is AAV1, AAV2, AAV3, AAV4, AAV5, AAV6, AAV7, AAV8, AAV9, AAV10, AAV11, AAV12, AAV13, AAV rh.74 or AAV-B1.

9. The method of claim 1, wherein the adeno-associated virus (AAV) is AAV6, AAV rh.74 or AAV-B1.

10. The method of claim 2, wherein the U6 promoter comprises the nucleotide sequence of SEQ ID NO: 3.

11. The method of claim 2, wherein the nucleic acid comprises the polynucleotide sequence of any one of SEQ ID NOS: 1, 2, and 10913-10968.

12. The method of claim 2, wherein the adeno-associated virus (AAV) is AAV1, AAV2, AAV3, AAV4, AAV5, AAV6, AAV7, AAV8, AAV9, AAV10, AAV11, AAV12, AAV13, AAV rh.74 or AAV-B1.

13. The method of claim 2, wherein the adeno-associated virus (AAV) is AAV6, AAV rh.74 or AAV-B1.

14. The method of claim 3, wherein the U6 promoter comprises the nucleotide sequence of SEQ ID NO: 3.

15. The method of claim 3, wherein the nucleic acid comprises the polynucleotide sequence of any one of SEQ ID NOS: 1, 2, and 10913-10968.

16. The method of claim 3, wherein the adeno-associated virus (AAV) is AAV1, AAV2, AAV3, AAV4, AAV5, AAV6, AAV7, AAV8, AAV9, AAV10, AAV11, AAV12, AAV13, AAV rh.74 or AAV-B1.

17. The method of claim 3, wherein the adeno-associated virus (AAV) is AAV6, AAV rh.74 or AAV-B1.

18. The method of claim 1, wherein the U6 promoter comprises the nucleotide sequence of SEQ ID NO: 4.

19. The method of claim 2, wherein the U6 promoter comprises the nucleotide sequence of SEQ ID NO: 4.

20. The method of claim 3, wherein the U6 promoter comprises the nucleotide sequence of SEQ ID NO: 4.

* * * * *